(12) United States Patent
Adams

(10) Patent No.: US 6,180,338 B1
(45) Date of Patent: Jan. 30, 2001

(54) METHOD, REAGENT AND KIT FOR THE DETECTION AND AMPLIFICATION OF NUCLEIC ACID SEQUENCES

(75) Inventor: Craig W. Adams, Corona, CA (US)

(73) Assignee: Beckman Coulter, Inc., Fullerton, CA (US)

( * ) Notice: Under 35 U.S.C. 154(b), the term of this patent shall be extended for 0 days.

(21) Appl. No.: 08/068,393

(22) Filed: May 27, 1993

Related U.S. Application Data

(63) Continuation-in-part of application No. 07/925,059, filed on Aug. 4, 1992, now abandoned.

(51) Int. Cl.⁷ ........................................... C12Q 1/68
(52) U.S. Cl. ............................................ 435/6; 435/91.2
(58) Field of Search ................................ 435/6, 91.2

(56) References Cited

U.S. PATENT DOCUMENTS

| 4,683,195 | 7/1987 | Mullis et al. | 435/6 |
|---|---|---|---|
| 4,683,202 | 7/1987 | Mullis et al. | 435/91 |
| 4,883,750 | 11/1989 | Whiteley et al. | 435/6 |
| 4,988,617 | 1/1991 | Landegren et al. | 435/6 |
| 4,994,370 | 2/1991 | Silver et al. | 435/6 |
| 5,185,243 | 2/1993 | Ullman et al. | |

FOREIGN PATENT DOCUMENTS

| 0 258 017 A2 | 3/1988 | (EP) . | |
|---|---|---|---|
| 0 292 128 A1 | 11/1988 | (EP) . | |
| 0 327 429 A2 | 1/1989 | (EP) . | |
| 0 332 435 | 9/1989 | (EP) | C12Q/1/68 |
| 0 373 962 A2 | 12/1989 | (EP) . | |
| 0 357 336 A3 | 3/1990 | (EP) | C12Q/1/68 |
| 0 439 182 A2 | 7/1991 | (EP) . | |
| 0 450 594 A2 | 10/1991 | (EP) . | |
| 0 473 155 A2 | 3/1992 | (EP) . | |
| 0 477 972 A2 | 4/1992 | (EP) . | |
| 2 225 112A | 5/1990 | (GB) | G01N/33/53 |
| WO 89/09835 | 10/1989 | (WO) . | |
| WO 89/12696 | 12/1989 | (WO) . | |
| WO 91/17239 | 11/1991 | (WO) . | |
| WO 91/17270 | 11/1991 | (WO) . | |
| 93/00447 * | 1/1993 | (WO) | C12Q/1/68 |

OTHER PUBLICATIONS

The Ligase Chain Reaction in a PCR World, pp. 5–16:1991; PCR Methods and Applications, F. Barany.

Amplification of Nucleic Acid Sequences: The Choices Multiply, The Journal of NIH Research (Methods and Materials), pp. 81–86; Feb. 1991 (vol.3); Author Unknown.

Formation of Covalent Circles of Lamdba DNA by E. coli Extracts, Biochemistry, pp. 148–155:1967 (vol. 57); M. Gellert.

Genetic Disease Detection and DNA Amplification Using Cloned Thermostable Ligase, pp. 189–193:Jan. 1991 (vol. 88); Proc. Natl. Acad. Sci. F. Barany.

The Enzymatic Repair of DNA,I. Formation of Circular λDNA, Biochemistry, pp. 240–247:Apr. 19, 1967 (vol.58) Gefter et al.

Specific Enzymatic Amplification of DNA in Vitro: The Polymerase Chain Reaction; pp. 263–273:1986, Cold Spring Harbor Symposia on Quantitative Biology (vol. L1) K. Mullis, F. Faloona, S. Scharf, R. Saiki, G. Horn, and H. Erlich.

(List continued on next page.)

Primary Examiner—Scott W. Houtteman
(74) Attorney, Agent, or Firm—William H. May; Margaret A. Kivinski; Jeffrey I. Auerbach

(57) ABSTRACT

Methods and reagents for the detection and exponential amplification of target nucleic acid molecules are disclosed. The method generally employs a Primer Oligonucleotide which hybridizes in concert with a Blocker Oligonucleotide on a strand of the target molecule, and an End-Run Oligonucleotide which can hybridize to the Blocker Oligonucleotide.

36 Claims, 22 Drawing Sheets

OTHER PUBLICATIONS

Specific Synthesis DNA in Vitro via a Polymerase–Catalyzed Chain Reaction, pp. 335–350:1987 Methods in Enzymology, (vol. 155) K. Mullis, Fred A. Faloona.

Cystic Fibrosis: Molecular Biology and Therapeutic Implications, pp. 774–779:May 8, 1992 Science (vol. 256) Francis S. Collins.

Hot Prospect for New Gene Amplifier, pp. 254–257:Nov. 29, 1992, Science (vol. 254) Rick Weiss.

Triplet Repeat Mutations in Human Disease, pp. 784–789:May 8, 1992, Science (vol. 256) C. Thomas Caskey et al.

Malignant Hyperthermia, pp. 789–794:May 8, 1992, Science (vol. 256) D.H. MacLennan et al.

DNA Ligase: Structure. Mechanism, and Function, pp. 790–797:Nov. 29, 1974, Science (vol. 186) I.R. Lehman.

Gaucher Disease: New Molecular Approaches to Diagnosis and Treatment, pp. 794–799:May 8, 1992 Science (vol 256); E. Beutler.

Molecular Genetics of Epidermolysis Bullosa, pp. 799–804:May 8, 1992, Science (vol. 256) E. Epstein, Jr.

On the Molecular Genetics of Reinitis Pigmentos, pp. 804–808:May 8, 1992 Science (vol. 256); P. Humphries et al.

Human Gene Therapy, pp. 808–813:May 8, 1992; Science (vol. 256); W. French Anderson.

Enzymatic Breakage and Joining of Deoxyribonucleic Acid, I Repair of Single–Strand Breaks in DNA by an Enzyme System from *Escherichi coli* Infected with T4 Bacteriophage, Biochemistry; pp. 1021–1028:Feb. 13, 1967; Weiss and Richardson.

A Ligase–Medicated Gene Detection Technique, pp. 1077–1080:Aug. 26, 1988; Science (vol. 241) Landegren, Kaiser, Sanders, Hood.

Linkage of Polynucleotides Through Phosphodiester Bonds By An Enzyme From *Escherichia coli*, Biochemistry (vol. 57) pp. 1426–1433:1967; Olivera and Lehman.

Sequence–Selective Recognition of DNA by Strand Displacement with a Thymine–Substituted Polyamide, pp. 1497–1500:Dec. 6, 1991; Science (vol. 254); P.E. Nielson.

Peptide Nucleic Acids (PNA). Oligonucleotide Analogues with an Achiral Peptide Backbone, pp. 1895–1897:1986; J. Am. Chem. Soc., vol. 114, No. 5; M. Egholm.

Automated DNA Diagnostics Using an ELISA–based Oligonucleotide Ligation Assay, pp. 8923–8927:Jun. 16, 1990; Proc. Natl. Acad. Sci., vol. 87, D. Nickerson.

Alzheimer's Disease: A Cell Biological Perspective, pp. 780–783:May 8, 1992; Science (vol. 256); K. Kosik.

Wright, Pat A. & Wynford–Thomas, David, The Polymerase Chain Reaction: MIracle or Mirage? A Critical Review of its Uses and Limitations in Diagnosis and Research; Journey of Pathology, vol. 162:99–117 (1990).

Wu, Dan Y. & Wallace, R. Bruce, "The Ligation Amplification reaction (LAR)—Amplification of Specific DNA Sequential Rounds of Template–Dependent Ligation"; Genomics 4, 500–569 (1989).

* cited by examiner

↓ Elongation of A
Denaturation
Ligation of B/C
Additional Moiety Hybridization

↓ Repeat As Desired

Elongation of C to B
Ligation of B/C
Denaturation
Additional Moiety Hybridization Repeat As Desired Elongation of A
Denaturation
Extension of C and Ligation of B/C
Additional Moiety Hybridization Repeat As Desired Stage 1

Repeat as Desired

Elongation of C
Ligation of B/C
Denaturation
Elongation of A

Stage 2

Repeat as Desired

Ligation of B'/C'
Elongation of A'
Denaturation

5' - Target - 3'
GCC CTT CCC AAC AGT TGC GCA GCC TGA ATG GCG AAT GGC GCT GCT TTG C Blocker' 3' G TTG TCA ACG CGT ·0GG ACT TAC C•GC TTA CCG CG 5'
                                                        Primer End Run    5' GT TGC GCA GCC TGA ATG G 3'

Fig. 10

METHOD, REAGENT AND KIT FOR THE DETECTION AND AMPLIFICATION OF NUCLEIC ACID SEQUENCES

This application is a continuation-in-part of application Ser. No. 07/925,059 filed Aug. 4, 1992 abandoned.

FIELD OF THE INVENTION

The invention relates to the analysis of deoxyribonucleic acid ("DNA") and ribonucleic acid ("RNA"), the determination of the presence of a predetermined specific DNA and/or RNA nucleotide sequence, and the exponential amplification of such a sequence.

BACKGROUND OF THE INVENTION

An ability to detect the presence of a nucleic acid molecule having a particular predetermined sequence is of substantial importance in a variety of fields, such as forensics, medicine, epidemiology and public health, and in the prediction and diagnosis of disease. Such an ability can aid criminal investigations, by excluding wrongly accused individuals or by implicating culpable parties. It can be exploited to permit the identification of the causal agent of infectious disease, or the characterization of tumors and tissue samples, or ensure the wholesomeness of blood products.

An ability to detect the presence of a particular nucleic acid sequence in a sample is important in predicting the likelihood that two individuals are related to one another, or that an individual will suffer from a genetic disease. Such an ability can also be used in assays to determine the purity of drinking water, milk, or other foods.

In many cases of interest, the desired nucleic acid sequence is present at a very low concentration in the sample. In such cases, unless assay sensitivity can be increased through the use of sophisticated labels, the presence of the desired molecule may escape detection. Assay sensitivity may be increased by altering the manner in which detection is reported or signaled to the observer. Thus, for example, assay sensitivity can be increased through the use of detectably labeled reagents. A wide variety of such labels have been used for this purpose: enzyme labels (Kourilsky et al.; U.S. Pat. No. 4,581,333); radioisotopic labels (Falkow et al., U.S. Pat. No. 4,358,535; Berninger, U.S. Pat. No. 4,446,237); fluorescent labels (Albarella et al., EP 144914); chemical labels (Sheldon III et al., U.S. Pat. No. 4,582,789; Albarella et al., U.S. Pat. No. 4,563,417), modified bases (Miyoshi et al., EP 119448), etc.

Although the use of highly detectable labeled reagents can improve the sensitivity of nucleic acid detection assays, the sensitivity of such assays remains limited by practical problems which are largely related to non-specific reactions that increase the background signal produced in the absence of the nucleic acid the assay is designed to detect. Thus, for some applications, the anticipated concentration of the desired nucleic acid molecule will be too low to permit its detection by any of the above-described methods.

One method for overcoming the sensitivity limitation of nucleic acid concentration is to selectively amplify the nucleic acid molecule whose detection is desired prior to performing the assay. In vivo recombinant DNA methodologies capable of amplifying purified nucleic acid fragments have long been recognized (Cohen et al., U.S. Pat. No. 4,237,224; Sambrook, J. et al., In: *Molecular Cloning: A Laboratory Manual*, Cold Spring Harbor Laboratory Press, Cold Spring Harbor, N.Y. (1989)). Typically, such methodologies involve the introduction of the nucleic acid fragment into a DNA or RNA vector, the clonal amplification of the vector, and the recovery of the amplified nucleic acid fragment.

Recently, in vitro amplification methods have been developed. The impact of such methods has been phenomenal—without such amplification, most of the foregoing exemplary fields would not be possible. Thus, as the areas in which DNA amplification has expanded, the requirements placed upon various amplification techniques have changed. Accordingly, a very real and ongoing need exists for highly specific amplification techniques.

Perhaps the most widely practiced of these methods is the "polymerase chain reaction" ("PCR") (Mullis, K. et al., *Cold Spring Harbor Symp. Quant. Biol.* 51:263–273 (1986); Erlich H. et al., EP 50,424; EP 84,796, EP 258,017, EP 237,362; Mullis, K., EP 201,184; Mullis K. et al., U.S. Pat. No. 4,683,202; Erlich, H., U.S. Pat. No. 4,582,788; and Saiki, R. et al., U.S. Pat. No. 4,683,194), which references are incorporated herein by reference).

PCR achieves the amplification of a specific nucleic acid sequence using two oligonucleotide primers complementary to regions of the sequence to be amplified. Extension products incorporating the primers then become templates for subsequent replication steps. The method selectively increases the concentration of a desired nucleic acid molecule even when that molecule has not been previously purified and is present only in a single copy in a particular sample. The method can be used to amplify either single or double stranded DNA.

The method involves the use of a DNA polymerase to direct the template-dependent, extension of a pair of oligonucleotide primers. The primer extension products then become templates for subsequent replication steps.

The precise nature of the two oligonucleotide primers of the PCR method is critical to the success of the method. As is well known, a molecule of DNA or RNA possesses directionality, which is conferred through the 5'→3' linkage of the sugar-phosphate backbone of the molecule. Two DNA or RNA molecules may be linked together through the formation of a phosphodiester bond between the terminal 5' phosphate group of one molecule and the terminal 3' hydroxyl group of the second molecule. Polymerase dependent amplification of a nucleic acid molecule proceeds by the addition of a 5' nucleoside triphosphate to the 3' hydroxyl end of a nucleic acid molecule. Thus, the action of a polymerase extends the 3' terminus of a nucleic acid molecule. The oligonucleotide sequences of the two PCR primers are selected such that they contain sequences identical to, or complementary to, sequences which flank the sequence of the particular nucleic acid molecule whose amplification is desired. More specifically, the nucleotide sequence of the "first" primer is selected such that it is capable of hybridizing to an oligonucleotide sequence located 3' to the sequence of the desired nucleic acid molecule, whereas the nucleotide sequence of the "second" primer is selected such that it contains a nucleotide sequence identical to one present 5' to the sequence of the desired nucleic acid molecule. Both primers possess the 3' hydroxyl groups which are necessary for enzyme mediated nucleic acid synthesis.

The PCR reaction is capable of exponential amplification of specific nucleic acid sequences because the extension product of the "first" primer contains a sequence which is complementary to a sequence of the "second" primer, and thus will serve as a template for the production of an extension product of the "second" primer. Similarly, the extension product of the "second" primer, of necessity, contain a sequence which is complementary to a sequence of the "first" primer, and thus will serve as a template for the production of an extension product of the "first" primer. Thus, by permitting cycles of hybridization, polymerization, and denaturation, a geometric increase in the concentration of the desired nucleic acid molecule can be achieved.

PCR technology is useful in that it can achieve the rapid and extensive amplification of a polynucleotide molecule (Mullis, K. B., Cold Spring Harbor Symp. Quant. Biol. 51:263–273 (1986); Saiki, R. K., et al., Bio/Technology 3:1008–1012 (1985); Mullis, K. B., et al., Met. Enzymol. 155:335–350 (1987), which references are incorporated herein by reference). Nevertheless, several practical problems exist with PCR. First extraneous sequences along the two templates can hybridize with the primers; this results in co-amplification due to such non-specific hybridization. As the level of amplification increases, the severity of such co-amplification also increases. Second, because of the ability of PCR to readily generate millions of copies for each initial template, accidental introduction of the end-product of a previous reaction into other samples easily leads to false-positive results. Third, PCR, does not, in and of itself, allow for detection of single-base changes, i.e. the protocol does not intrinsically discriminate between a "normal" sequence and an allelic variant sequence.

The advent of PCR led to the development of additional amplification methods. One such alternative method is the "Ligase Chain Reaction" ("LCR") (Barany, F., Proc. Natl. Acad. Sci. (U.S.A.) 88:189–193 (1991). LCR uses two pairs of oligonucleotide probes to exponentially amplify a specific target. The sequences of each pair of oligonucleotides is selected to permit the pair to hybridize to abutting sequences of the same strand of the target. Such hybridization forms a substrate for a template-dependent ligase. Thus, the hybridization of the first pair of oligonucleotides to a "first" strand of the target, permits the oligonucleotides to be ligated together. The sequence of the second pair of oligonucleotides is selected such that the oligonucleotides can hybridize to abutting sequences of this ligation product, thereby forming a second substrate for ligation. The ligation product of the second strand thus possesses a sequence that is substantially identical to that of the "first" strand of the target.

As with PCR, the resulting products thus serve as templates in subsequent cycles and an exponential amplification of the desired sequence is obtained. Beneficially, LCR can be utilized to detect mutations, and in particular, single nucleotide mutations. Thus, the primers can be designed such that they can be ligated together only if the target molecule either contains or lacks a predetermined mutational site.

One problem associated with LCR is that, by definition, the procedure requires four oligonucleotides and a ligase, and may result in the non-specific "blunt-end ligation" of the oligonucleotides. Such non-specific "blunt-end ligation," if it occurs, will cause a target-independent exponential amplification of the oligonucleotides. This can lead to high background signal or false-positive results.

This deficiency can, in some respects, be addressed using oligonucleotides that hybridize to adjacent, but non-abutting sequences (PCT Appl. WO 90/01069). As in LCR, such a method involves the use of two sets of primers. However, since the primers are designed to hybridize to non-abutting sequences of the target molecule, the hybridization product contains a "gap" separating the hybridized oligonucleotides. These gaps are then "filled" with complementary dNTPs (as mediated by DNA polymerase), or by an additional pair of oligonucleotides. Thus, at the end of each cycle, each single strand has a complement capable of serving as a target during the next cycle and exponential amplification of the desired sequence is obtained.

While this protocol avoids the LCR problem of non-specific blunt end ligation in the absence of target, it does so at the expense of LCR's capacity to detect single base mutational changes, and requires that the sequence of the entire "gap" be known in advance. In addition, a critical difficulty in using this technique is the need to design the oligonucleotide primers such that the "gap" can be "repaired" with only a subset of the dNTPs. I.e., the gap cannot comprise all four of the bases such that only a maximum of three of the four dNTPs can be added to the reaction vessel.

The "Oligonucleotide Ligation Assay" ("OLA") (Landegren, U. et al., Science 241:1077–1080 (1988)) shares certain similarities with LCR. The OLA protocol uses two oligonucleotides which are designed to be capable of hybridizing to abutting sequences of a single strand of a target. OLA, like LCR, is particularly suited for the detection of point mutations. Unlike LCR, however, OLA results in "linear" rather than exponential amplification of the target sequence. A problem associated with OLA, then, is the lack of exponential amplification.

Nickerson, D. A. et al. have described a nucleic acid detection assay that combines attributes of PCR and OLA (Nickerson, D. A. et al., Proc. Natl. Acad. Sci. (U.S.A.) 87:8923–8927 (1990). In this method, PCR is used to achieve the exponential amplification of target DNA, which is then detected using OLA. In addition to requiring multiple, and separate, processing steps, one problem associated with such combinations is that they inherit all of the problems associated with PCR and OLA.

Other known nucleic acid amplification procedures include transcription-based amplification systems (Kwoh D et al., Proc. Natl. Acad. Sci. (U.S.A.) 86:1173 (1989); Gingeras, T. R. et al., PCT appl. WO 88/10315 (priority: U.S. patent applications Ser. Nos. 064,141 and 202,978)). Schemes based on ligation of two (or more) oligonucleotides in the presence of nucleic acid having the sequence of the resulting "di-oligonucleotide", thereby amplifying the di-oligonucleotide, are also known (Wu, D. Y. et al., Genomics 4:560 (1989)).

Miller, H. I. et al., PCT appl. WO 89/06700 (priority: U.S. patent application Ser. No. 146,462, filed Jan. 21, 1988), disclose a nucleic acid sequence amplification scheme based on the hybridization of a promoter/primer sequence to a target single-stranded DNA ("ssDNA") followed by transcription of many RNA copies of the sequence. This scheme was not cyclic; i.e. new templates were not produced from the resultant RNA transcripts.

Malek, L. T. et al., U.S. Pat. No. 5,130,238, and Davey, C. et al. (European Patent Application Publication no. 329,822) disclose a nucleic acid amplification process involving cyclically synthesizing single-stranded RNA ("ssRNA"), ssDNA, and double-stranded DNA (dsDNA). The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5'-to its homology to its template. This primer is then extended by DNA polymerase (exemplified by the large "Klenow" fragment of *E. coli* DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA. An improvement of this method was developed by Schuster et al. (U.S. Pat. No. 5,169,766) who show that the primer extension taught by Malek (U.S. Pat. No. 5,130,238) is not necessary.

All of the above amplification procedures depend on the principle that an end product of a cycle is functionally identical to a starting material. Thus, by repeating cycles, the nucleic acid is amplified exponentially.

An isothermal amplification method has been described in which restriction endonucleases and ligases are used to achieve the amplification of target molecules that contain nucleotide 5'-[α-thio]triphosphates in one strand of a restriction site (Walker, G. T. et al., *Proc. Natl. Acad. Sci. (U.S.A.)* 89:392–396 (1992)).

Methods that use thermo-cycling, e.g. PCR or Wu, D. Y. et al., *Genomics* 4:560 (1989)), have a theoretical maximum increase of product of 2-fold per cycle, because in each cycle a single product is made from each template. In practice, the increase is always lower than 2-fold. Further slowing the amplification is the time spent in changing the temperature. Also adding delay is the need to allow enough time in a cycle for all molecules to have finished a step. Molecules that finish a step quickly must "wait" for their slower counterparts to finish before proceeding to the next step in the cycle; to shorten the cycle time would lead to skipping of one cycle by the "slower" molecules, leading to a lower exponent of amplification.

Methods that include a transcription step, e.g. that of the present invention or of Malek, L. T. et al. (U.S. Pat. No. 5,130,238) or Davey, C. et al. (European Patent Application Publication no. 329,822), can increase product by more than a factor of 2 at each cycle. Indeed, as 100 or more transcripts can be made from a single template, factors of increase of 100 or more are theoretically readily attainable. Furthermore, if all steps are performed under identical conditions, no molecule which has finished a particular step need "wait" before proceeding to the next step. Thus amplifications that are based on transcription and that do not require thermo-cycling are potentially much faster than thermo-cycling amplifications such as PCR.

In sum, although a variety of amplification methods have been developed, a strictly target-dependent method that is capable of mediating the exponential amplification of a target molecule, and which possesses the ability to detect single nucleotide allelic variation would be highly desirable. The present invention provides such a method.

SUMMARY OF THE INVENTION

The present invention thus provides an improved method for amplifying a desired sequence present in a target molecule. The methodology generally relies upon the hybridization of a Blocker Oligonucleotide to a target molecule. The hybridization positions the Blocker Oligonucleotide such that it abuts a Primer Oligonucleotide, or an extension product of the Primer Oligonucleotide, that is also hybridized to the target. As a result of such positioning, the Primer Oligonucleotide (or extension product thereof) and the Blocker Oligonucleotide can be ligated to one another. Such ligation provides a substrate for the polymerase-mediated, template-dependent extension of an End-Run Oligonucleotide that is capable of hybridizing to the Blocker Oligonucleotide. Since the extension product of the End-Run Oligonucleotide is complementary to the Primer Oligonucleotide and Blocker Oligonucleotide sequences, the reaction is capable of mediating the exponential amplification of the target molecule. Significantly, the method is capable of distinguishing between allelic variants that differ by as little as a single nucleotide.

In detail, the invention provides a method of amplifying the concentration of a target nucleic acid molecule comprising the steps:

(A) hybridizing a Blocker Oligonucleotide to the target nucleic acid molecule to thereby form a double-stranded nucleic acid molecule;

(B) hybridizing a Primer Oligonucleotide to the target nucleic acid molecule of the double-stranded nucleic acid molecule such that the 3' terminus of the Primer Oligonucleotide abuts, or can be extended in a polymerase-mediated, template-dependent primer extension reaction to abut, the 5' terminus of the hybridized Blocker Oligonucleotide;

(C) (1) where the 3' terminus of the hybridized Primer Oligonucleotide abuts the 5' terminus of the hybridized Blocker Oligonucleotide, conducting step (D); or (2) where the 3' terminus of the hybridized Primer Oligonucleotide does not abut the 5' terminus of the hybridized Blocker Oligonucleotide, causing the 3' terminus of the hybridized Primer Oligonucleotide to be extended in a polymerase-mediated, template-dependent primer extension reaction, to thereby form a Primer extension product whose 3' terminus abuts the 5' terminus of the hybridized Blocker Oligonucleotide; then conducting step (D);

(D) ligating the abutting 3' terminus of the hybridized Primer Oligonucleotide of step (C) (1) or the abutting 3' terminus of the hybridized Primer extension product of step (C) (2) to the 5' terminus of the hybridized Blocker Oligonucleotide to thereby form a ligation product having the sequence of the Primer Oligonucleotide or the Primer extension product, and the sequence of the Blocker Oligonucleotide;

(E) hybridizing an End-Run Oligonucleotide to the sequence of the Blocker Oligonucleotide of the ligation product; and (F) extending the 3' terminus of the hybridized End-Run Oligonucleotide in a polymerase-mediated, template-dependent primer extension reaction to form an End-Run extension product and thereby amplify the concentration of the target molecule;;

wherein said step (A), said group of steps (B), (C) and (D), and said group of steps (E) and (F), can be conducted in any order with respect to one another.

The invention also provides the embodiment of the above method which additionally includes the steps:

(G) hybridizing a Blocker Oligonucleotide to the End-Run extension product to thereby form a double-stranded nucleic acid molecule;

(H) hybridizing a Primer Oligonucleotide to the End-Run extension product of the double-stranded nucleic acid molecule of step (G) to thereby form a double-stranded nucleic acid molecule wherein the 3' terminus of the Primer Oligonucleotide abuts, or can be extended in a polymerase-mediated, template-dependent primer extension reaction to abut, the 5' terminus of the hybridized Blocker Oligonucleotide;

(I) (1) where the 3' terminus of the hybridized Primer Oligonucleotide of step (H) abuts the 5' terminus of the hybridized Blocker Oligonucleotide, conducting step (J); or (2) where the 3' terminus of the hybridized Primer Oligonucleotide of step (H) does not abut the 5' terminus of the hybridized Blocker Oligonucleotide, causing the 3' terminus of the hybridized Primer Oligonucleotide to be extended in a polymerase-mediated, template-dependent primer extension reaction, to thereby form a Primer extension product whose 3' terminus abuts the 5' terminus of the hybridized Blocker Oligonucleotide; then conducting step (J);

(J) ligating the abutting 3' terminus of the hybridized Primer Oligonucleotide of step (I) (1) or the abutting 3' terminus of the hybridized Primer extension product of step (I) (2) to the 5' terminus of the hybridized Blocker Oligonucleotide to thereby form and amplify the ligation product;

(K) hybridizing an End-Run Oligonucleotide to the sequence of the Blocker Oligonucleotide of the ligation product of step (J); and (L) extending the 3' terminus of the hybridized End-Run Oligonucleotide in a polymerase-mediated, template-dependent primer extension reaction to thereby form and amplify an End-Run extension product.

The invention is also directed to the embodiment wherein of the above methods wherein after step (F), the following additional steps are included:

(G) hybridizing a second Blocker Oligonucleotide to the End-Run extension product to thereby form a double-stranded nucleic acid molecule, wherein the second Blocker Oligonucleotide hybridizes to the End-Run extension product at a site to which the Blocker Oligonucleotide of step (A) or the Primer Oligonucleotide of step (B) cannot hybridize;

(H) hybridizing a second Primer Oligonucleotide to the End-Run extension product of the double-stranded nucleic acid molecule such that the 3' terminus of the second Primer Oligonucleotide abuts, or can be extended in a polymerase-mediated, template-dependent primer extension reaction to abut, the 5' terminus of the hybridized second Blocker Oligonucleotide;

(I) (1) where the 3' terminus of the hybridized second Primer Oligonucleotide abuts the 5' terminus of the hybridized second Blocker Oligonucleotide, conducting step (J); or (2) where the 3' terminus of the hybridized second Primer Oligonucleotide does not abut the 5' terminus of the hybridized second Blocker Oligonucleotide, causing the 3' terminus of the hybridized second Primer Oligonucleotide to be extended in a polymerase-mediated, template-dependent primer extension reaction, to thereby form a second Primer extension product whose 3' terminus abuts the 5' terminus of the hybridized second Blocker Oligonucleotide; then conducting step (J);

(J) ligating the abutting 3' terminus of the hybridized second Primer Oligonucleotide of step (I) (1) or the abutting 3' terminus of the hybridized second Primer extension product of step (I) (2) to the 5' terminus of the hybridized Blocker Oligonucleotide to thereby form a second ligation product having the sequence of the second Primer Oligonucleotide or the second Primer extension product, and the sequence of the second Blocker Oligonucleotide;

(K) hybridizing a second End-Run Oligonucleotide to the sequence of the second Blocker Oligonucleotide of the second ligation product; and (L) extending the 3' terminus of the hybridized second End-Run Oligonucleotide in a polymerase-mediated, template-dependent primer extension reaction to form a second End-Run extension product and thereby amplify the concentration of the sequence of the target molecule.

As an alternative to steps (G) through (H) described above, the present invention can include the embodiment wherein after step (F), the following additional steps are included:

(G) hybridizing a second Blocker Oligonucleotide to the ligation product to thereby form a double-stranded nucleic acid molecule, wherein the second Blocker Oligonucleotide hybridizes to the ligation product at a site to which the Blocker of step (A) or the Primer Oligonucleotide of step (B) cannot hybridize;

(H) hybridizing a second Primer Oligonucleotide to the ligation product of the double-stranded nucleic acid molecule such that the 3' terminus of said second Primer Oligonucleotide abuts, or can be extended in a polymerase-mediated, template-dependent primer extension reaction to abut, the 5' terminus of the hybridized second Blocker Oligonucleotide;

(I) (1) where the 3' terminus of the hybridized second Primer Oligonucleotide abuts the 5' terminus of the hybridized second Blocker Oligonucleotide, conducting step (J); or (2) where the 3' terminus of the hybridized second Primer Oligonucleotide does not abut the 5' terminus of the hybridized second Blocker Oligonucleotide, causing the 3' terminus of the hybridized second Primer Oligonucleotide to be extended in a polymerase-mediated, template-dependent primer extension reaction, to thereby form a second Primer extension product whose 3' terminus abuts said 5' terminus of the hybridized second Blocker Oligonucleotide; then conducting step (J);

(J) ligating the abutting 3' terminus of the hybridized second Primer Oligonucleotide of step (I) (1) or the abutting 3' terminus of the hybridized second Primer extension product of step (I) (2) to the 5' terminus of the hybridized Blocker Oligonucleotide to thereby form a second ligation product having the sequence of the second Primer Oligonucleotide or the second Primer extension product, and the sequence of the second Blocker Oligonucleotide;

(K) hybridizing a second End-Run Oligonucleotide to the sequence of the second Blocker Oligonucleotide of the second ligation product; and (L) extending the 3' terminus of the hybridized second End-Run Oligonucleotide in a polymerase-mediated, template-dependent primer extension reaction to form a second End-Run extension product and thereby amplify the concentration of the sequence of the target molecule.

The invention also provides methods of determining whether a selected nucleotide is present at a predetermined site of a target nucleic acid molecule. Such detection methods can depend upon the ability of Blocker Oligonucleotides and Primer Oligonucleotides to ligate and form ligation products, Primer Oligonucleotides to form extension products, End-Run Oligonucleotides to form extension products, and any of the Oligonucleotides to hybridize to portions of the target nucleic acid molecule. Predetermined sites of target nucleic acid molecules include sites positioned adjacent or abutting the 5' end of Block Oligonucleotide, sites positioned adjacent or abutting the 3' end of Primer Oligonucleotide, and positions adjacent or abutting the 3' end of End-Run Oligonucleotides.

An exemplary embodiment for determining whether a selected nucleotide is present includes the steps:

(A) providing conditions for hybridizing a Blocker Oligonucleotide to the target nucleic acid molecule to thereby form a partially double-stranded nucleic acid molecule, wherein the 5' terminus of the hybridized Blocker Oligonucleotide is positioned such that its 5' terminal nucleotide opposes the predetermined site of the target molecule, and is complementary to the selected nucleotide;

(B) providing conditions for hybridizing a Primer Oligonucleotide to the target nucleic acid molecule of the partially double-stranded nucleic acid molecule such that the 3' terminus of the Primer Oligonucleotide abuts, or can be extended in a polymerase-mediated, template-dependent primer extension reaction to abut, the 5' terminus of the hybridized Blocker Oligonucleotide;

(C) (1) where if the 3' terminus of the Primer Oligonucleotide abuts the 5' terminus of the Blocker Oligonucleotide, conducting step (D); or (2) where if the 3' terminus of the Primer Oligonucleotide does not abut the 5' terminus of the Blocker Oligonucleotide, causing the 3' terminus of the hybridized Primer Oligonucleotide to be extended in a polymerase-mediated, template-dependent primer extension reaction, to thereby form a Primer extension product whose 3' terminus abuts the 5' terminus of the Blocker Oligonucleotide; then conducting step (D);

(D) incubating the abutting 3' terminus of the hybridized Primer Oligonucleotide of step (C) (1) or the abutting 3' terminus of the hybridized Primer extension product of step (C) (2) and the 5' terminus of the hybridized Blocker Oligonucleotide in the presence of a ligase, under conditions conducive to nucleic acid ligation;

(E) determining whether the selected nucleotide is present at the predetermined site by detecting whether step (D) results in the formation of a ligation product having the sequence of the Primer Oligonucleotide or the Primer extension product and the Blocker Oligonucleotide, the detection being accomplished by the sub-steps:

(1) providing an End-Run Oligonucleotide to the incubation, and maintaining the incubation under conditions sufficient to permit nucleic acid hybridization and polymerase-mediated, template-dependent primer extension to occur; and (2) determining whether the End-Run Oligonucleotide is extended to contain a sequence complementary to a sequence of the Primer Oligonucleotide.

In accordance with the present invention, another method of determining whether a selected nucleotide is present at a predetermined site of a target nucleic acid molecule includes the steps:

(A) providing conditions for hybridizing a Blocker Oligonucleotide to the target nucleic acid molecule to thereby form a double-stranded nucleic acid molecule, wherein the 5' terminus of the hybridized Blocker Oligonucleotide is positioned such that its 5' terminal nucleotide is hybridized to the nucleotide located immediately 3' of the predetermined site of the target molecule;

(B) providing conditions for hybridizing a Primer Oligonucleotide to the target nucleic acid molecule of the partially double-stranded nucleic acid molecule such that the 3' terminus of the Primer Oligonucleotide abuts the 5' terminus of the hybridized Blocker Oligonucleotide; wherein the 3' terminal nucleotide is complementary to the selected nucleotide;

(C) incubating the abutting 3' terminus of the hybridized Primer Oligonucleotide and the 5' terminus of the hybridized Blocker Oligonucleotide in the presence of a ligase, under conditions conducive to nucleic acid ligation;

(D) determining whether the selected nucleotide is present at the predetermined site by detecting whether step (C) results in the formation of a ligation product having the sequence of the Primer Oligonucleotide and the Blocker Oligonucleotide, the detection being accomplished by the sub-steps:

(1) providing an End-Run Oligonucleotide to the incubation, and maintaining the incubation under conditions sufficient to permit nucleic acid hybridization and polymerase-mediated, template-dependent primer extension to occur; and (2) determining whether the End-Run Oligonucleotide is extended to contain a sequence complementary to a sequence of the Primer Oligonucleotide.

The invention also includes the embodiment of the above method wherein the determination of whether the End-Run Oligonucleotide is extended to contain a sequence complementary to a sequence of the Primer Oligonucleotide is conducted by amplifying any End-Run extension product using a method comprising the sub-steps:

(a) hybridizing the Blocker Oligonucleotide to any of the End-Run extension products present in the incubation to thereby form double-stranded nucleic acid molecules;

(b) hybridizing the Primer Oligonucleotide to the End-Run extension product of any of the double-stranded nucleic acid molecules such that the 3' terminus of the Primer Oligonucleotide abuts, or can be extended in a polymerase-mediated, template-dependent primer extension reaction to abut, the 5' terminus of the hybridized Blocker Oligonucleotide;

(c) (1) where the 3' terminus of the hybridized Primer Oligonucleotide abuts the 5' terminus of the hybridized Blocker Oligonucleotide, conducting step (d); or (2) where the 3' terminus of the hybridized Primer Oligonucleotide does not abut the 5' terminus of the hybridized Blocker Oligonucleotide, causing the 3' terminus of the hybridized Primer Oligonucleotide to be extended in a polymerase-mediated, template-dependent primer extension reaction, to thereby form a Primer extension product whose 3' terminus abuts the 5' terminus of the hybridized Blocker Oligonucleotide; then conducting step (d);

(d) ligating the abutting 3' terminus of any of the hybridized Primer Oligonucleotide of step (c) (1) or the abutting 3' terminus of any of the hybridized Primer extension product of step (c) (2) to the 5' terminus of any of the hybridized Blocker Oligonucleotide to thereby form a ligation product having the sequence of the Primer Oligonucleotide or the Primer extension product, and the sequence of the Blocker Oligonucleotide;

(e) hybridizing the End-Run Oligonucleotide to the sequence of the Blocker Oligonucleotide of any of the ligation product; and (f) extending the 3' terminus of the hybridized End-Run Oligonucleotide in a polymerase-mediated, template-dependent primer extension reaction to form and amplify the End-Run extension product.

Further, and in accordance with the present invention, another method of determining whether a selected nucleotide is present at a predetermined site of a target nucleic acid molecule is dependent upon the capacity of an End-Run Oligonucleotide to extend in a polymerase mediated template dependent reaction. This method includes the steps of:

(A) hybridizing a Blocker Oligonucleotide to a nucleic acid sequence complementary to the target nucleic acid molecule to thereby form a partially double-stranded nucleic acid molecule;

(B) hybridizing a Primer Oligonucleotide to the nucleic acid sequence complementary to the target nucleic acid molecule of the double-stranded nucleic acid molecule such that the 3' terminus of the Primer Oligonucleotide abuts, or can be extended in a polymerase-mediated, template-dependent primer extension reaction to abut, the 5' terminus of the hybridized Blocker Oligonucleotide;

(C) (1) where the 3' terminus of the hybridized Primer Oligonucleotide abuts the 5' terminus of the hybridized Blocker Oligonucleotide, conducting step (D); or (2) where the 3' terminus of said hybridized Primer Oligonucleotide does not abut the 5' terminus of the hybridized Blocker Oligonucleotide, then causing the 3' terminus of the hybridized Primer Oligonucleotide to be extended in a polymerase-mediated, template-dependent primer extension reaction, to thereby form a Primer extension product whose 3' terminus abuts the 5' terminus of the hybridized Blocker Oligonucleotide; then conducting step (D);

(D) ligating the abutting 3' terminus of the hybridized Primer Oligonucleotide of step (C) (1) or the abutting 3' terminus of the hybridized Primer extension product of step (C) (2) to the 5' terminus of the hybridized Blocker Oligonucleotide to thereby form a ligation product having the sequence of the Primer Oligonucleotide or the Primer extension product, and the sequence of the Blocker Oligonucleotide;

(E) hybridizing an End-Run Oligonucleotide to the sequence of the Blocker Oligonucleotide of the ligation product, wherein the 3' terminus of the End-Run Oligonucleotide is complementary to the selected nucleotide and the 3' terminal nucleotide of the End-Run Oligonucleotide is capable of opposing the predetermined site of the target molecule;

(F) providing conditions for extending the 3' terminus of the hybridized End-Run Oligonucleotide in a polymerase-mediated, template-dependent primer extension reaction to form an End-Run extension product;

(G) determining whether the selected nucleotide is present at the predetermined site by detecting whether step (F) results in the formation of an End-Run extension product.

The present invention also contemplates alternative methods of determining whether a selected nucleotide is present at a predetermined site of a target nucleic acid molecule. Such detection methods can depend upon the ability of a Primer Oligonucleotide to hybridize to the target nucleic acid molecule and form a Primer extension product. Such an embodiment includes the steps:

(A) providing conditions for hybridizing a Blocker Oligonucleotide to the target nucleic acid molecule to thereby form a partially double-stranded nucleic acid molecule;

(B) providing conditions for hybridizing a Primer Oligonucleotide to the target nucleic acid molecule of the partially double-stranded nucleic acid molecule, wherein the 3' terminus of the Primer Oligonucleotide opposes the predetermined site of the target molecule;

(C) providing conditions for extending the 3' terminus of the hybridized Primer Oligonucleotide in a polymerase-mediated, template-dependent primer extension reaction, to thereby form a Primer Extension product;

(D) determining whether the selected nucleotide is present at the predetermined site by detecting whether step (C) results in the formation of a Primer Extension product, the detection being accomplished by the sub-steps:

(1) incubating and Primer Extension product and the 5' terminus of the hybridized Blocker Oligonucleotide in the presence of a ligase, under conditons conducive to nucleic acid ligation;

(2) detecting whether step (1) results in the formation of a ligation product having the sequence of the Primer Oligonucleotide extension product and the Block Oligonucleotide, the detection being accomplished by the step:

(a) providing an End-Run Oligonucleotide to the incubation, and maintaining the incubation under conditions sufficient to permit nucleic acid hybridization and polymerase-mediated, template-dependent primer extension to occur; and (b) determining whether the End-Run Oligonucleotide is extended to contain a sequence complementary to a sequence of the Primer Oligonucleotide.

As a feature of the present invention, methods taught herein can be used for first amplifying the concentration of any nucleic acid followed by methods, also taught herein, for determining whether a selected nucleotide is present at a predetermined site of the amplified nucleic acid.

The invention is also directed to "kits," and in particular, to a kit comprising reagents for amplification of at least one target sequence comprising at least one region having a defined nucleic acid sequence, the kit comprising at least one container, the container comprising at least one Blocker moiety; at least one Primer moiety; and least one End-Run moiety, where the Blocker moiety is capable of hybridizing to a portion of the nucleic acid sequence, the Primer moiety is capable of hybridizing to a different portion of the nucleic acid sequence, and the End-Run moiety comprises a sequence which is complementary to at least a portion of the Blocker moiety.

Optionally, the kits may include reagents, enzymes and/or buffers designed to facilitate the End-Run Amplification.

BRIEF DESCRIPTION OF THE FIGURES

FIG. 9 provides a schematic representation of the "Loop" ERA embodiment ("LERA") of the present invention.

FIG. 10 provides a schematic alignment of the target, with the Blocker, Primer and End-Run Oligonucleotides used in Examples I and II.

DESCRIPTION OF THE PREFERRED EMBODIMENTS

I. Amplification of Nucleic Acid Molecules

Figure 1:
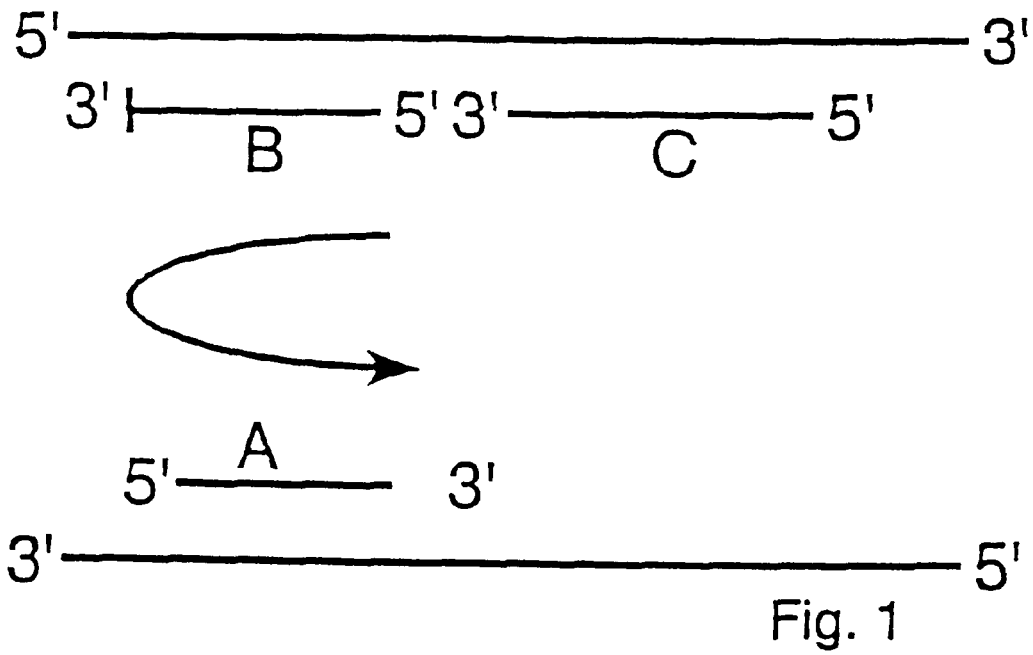
FIG. 1 provides a schematic representation of the positioning and characteristics of the "End-Run," "Blocker," and "Primer" oligonucleotides used to amplify a double-stranded target molecule in the "gapless" ERA embodiment of the present invention. In the Figure, the "End-Run," "Blocker," and "Primer" oligonucleotides are referred to as A, B and C, respectively.

The present invention provides a method—"End-Run Amplification" or "ERA"—for amplifying a desired nucleic acid molecule present in a sample. As such, it provides both a means for determining whether a particular desired molecule is present in a sample, and a means for obtaining sufficient amounts of the desired sequence to permit its sequence or structural analysis.

The molecules that can be generated through the use of the present method can have a length ranging from a few nucleotides to several kilobases. The "desired" molecules of the invention are said to have a sequence that is "complementary," or substantially complementary to the sequence of a "target" strand of a nucleic acid molecule.

As used herein, two sequences are said to be able to "hybridize" to one another if they are capable of forming an anti-parallel double-stranded nucleic acid structure. Two nucleic acid molecules are said to be "complementary" if they can hybridize to one another with sufficient stability to permit them to remain annealed to one another under at least conventional "low-stringency" conditions (see, Sambrook, J., et al., (In: *Molecular Cloning, a Laboratory Manual, 2nd Edition, Cold Spring Harbor Press*, Cold Spring Harbor, N.Y. (1989)), and Haymes, B. D., et al. (In: *Nucleic Acid*

*Hybridization, A Practical Approach*, IRL Press, Washington, D.C. (1985)), both herein incorporated by reference). Thus, two complementary molecules need not exhibit precise complementarity, but need only be sufficiently complementary in sequence to be able to form a stable double-stranded structure. Departures from complete complementarity are therefore permissible, so long as such departures are not sufficient to completely preclude hybridization to form a double-stranded structure.

The "amplification" that is achieved through the methods of the present invention denotes an increase in the amount of desired nucleic acid molecules present in a reaction vessel. "Substantial amplification" refers to greater than about 100-fold amplification.

The nucleic acid sequence that can be amplified by the methods of the present invention may DNA or RNA. Where the sequence is initially present as DNA, such DNA need not be either transcribed or translated. Thus, the present invention may be used to identify and/or amplify non-transcribed DNA or non-translated DNA, as well as DNA that is transcribed or translated. Likewise, where the desired sequence is initially present in an RNA molecule such RNA need not be translated.

Among the molecules which may be amplified include any naturally occurring procaryotic (for example, pathogenic or non-pathogenic bacteria, Escherichia, Salmonella, Clostridium, Agrobacter, Staphylococcus and Streptomyces, Streptococcus, Rickettsiae, Chlamydia, Mycoplasma, etc.), eukaryotic (for example, protozoans and parasites, fungi, yeast, higher plants, lower and higher animals, including mammals and humans) or viral (for example, Herpes viruses, HIV, influenza virus, Epstein-Barr virus, hepatitis virus, polio virus, etc.) or viroid nucleic acid. The nucleic acid molecule can also be any nucleic acid molecule which has been or can be chemically synthesized. Thus, the nucleic acid sequence may or may not be found in nature. In sum, the methods of the present invention are capable of identifying or amplifying any nucleic acid molecule, and do not require that the molecules to be amplified have any particular sequence or origin.

Although the nucleic acid molecule which is to be amplified may be in either a double-stranded or single-stranded form, if the nucleic acid is double-stranded at the start of the amplification reaction it is preferably first treated to render the two strands into a single-stranded, or partially single-stranded, form. Methods are known to render double-stranded nucleic acids into single-stranded, or partially single-stranded, forms, such as heating, or by alkali treatment, or by enzymatic methods (such a by helicase action, etc.), or by binding proteins, etc. General methods for accomplishing this treatment are provided by Sambrook, J. et al., In: *Molecular Cloning: A Laboratory Manual*, Cold Spring Harbor Laboratory Press, Cold Spring Harbor, N.Y. (1989)) and by Haymes, B. D., et al. (In: *Nucleic Acid Hybridization. A Practical Approach*, IRL Press, Washington, D.C. (1985)), which references are herein incorporated by reference.

Significantly, the invention places no restrictions on the nature of the sample being evaluated. Such samples may, for example be derived from an animal (such as a human or other mammal), or a plant, or may be synthetically derived.

In particular, the invention may be used to identify and amplify nucleic acid molecules present in blood (and blood products, such as serum, plasma, platelets), stool, sputum, mucus, serum, urine, saliva, teardrop, biopsy samples, histology tissue samples, PAP smears and other vaginal swabs, skin scrapes, semen, moles, warts, etc. Similarly, it may be used to identify and amplify nucleic acid molecules present in plant tissue.

The nucleic acids of such samples may be wholly unpurified, partially purified, or fully purified from any other component naturally associated with the sample. Typically, however, the sample will have been treated to a sufficient degree such that extraneous materials which might otherwise interfere with amplification of the nucleic acids are removed. For, e.g., a serum sample, preparation of the nucleic acids generally can comprise the following steps: incubate the serum for 1 hr. at 70° C. with proteinase K (Boehringer Mannheim) at 2.5 mg/ml in 25 mM MOPS (pH 6.5), 2.5 mM EDTA and 0.50 SDS. This is followed by the following extractions: phenol extraction and ether extraction. This is followed by ethanol precipitation. See, e.g., Larzul, et al. *J. Heptol.* 5:199–204 (1987). As noted, other protocols and techniques are readily available for such purification.

Since the invention places no constraints on the nature of the nucleic acid sequence that is to be identified and/or amplified, the invention is capable of identifying nucleic acid molecules that are naturally found in the sample (such as insulin mRNA sequences in pancreatic β-cell tissue), as well as sequences which though produced by the source animal or plant is indicative of disease (such as a gene sequence encoding a hemoglobin histopathy, or an oncogene product expressed exclusively or preferentially by neoplastic cells). Moreover, the invention may also be used to determine whether gene sequences of pathogenic bacteria, mold, fungi or viruses are present in a tissue sample.

The methods of the present invention may therefore be used to diagnose disease, or to establish pedigree and identity, as well as to assess the purity of agricultural products (milk, processed foodstuff, etc.), waste water, drinking water, air, etc.

Most preferably, the RNA or DNA sequence that is to be amplified will be amplified via a DNA polymerase or a reverse transcriptase to form a DNA amplification product, however, in embodiments in which an RNA amplification product is desired, an RNA polymerase may be employed. A "polymerase" is an enzyme that is capable of incorporating nucleotide triphosphates to extend a 3' hydroxyl group of a nucleic acid molecule, if that molecule has hybridized to a suitable template nucleic acid molecule. An oligonucleotide or polynucleotide whose 3' terminus can be extended by a polymerase is a "primer."

Since DNA polymerases polymerize nucleic acid molecules in a 5'→3' direction, they thus extend the 3' terminus of a complementary primer in a "template dependent manner." As used herein, the term "template dependent manner" refers to nucleic acid synthesis of RNA or DNA wherein the sequence of the newly synthesized strand of nucleic acid is dictated by complementary base pairing. In such a reaction, the target molecule serves as a "template," for the extension of the primer, such that the primer extension product has a sequence that is complementary to that of the template. Such polymerization typically requires the presence of nucleotide triphosphates ("dNTP"), i.e. deoxyadenosine 5'-triphosphate ("dATP"), deoxycytidine 5'-triphosphate ("dCTP"), deoxyguanosine 5'-triphosphate ("dGTP") and deoxythymidine 5'-triphosphate (typically abbreviated as "TTP" but for purposes of consistency, abbreviated herein as "dTTP"). Nucleoside triphosphate analogues, etc. (Piccirilli, J. A. et al., *Nature* 343:33–37 (1990) can be substituted or added to those specified above, provided that the base pairing, polymerase and strand displacing functions are not adversely affected to the point that the amplification does not proceed to the desired extent. In particular, deoxyinosine triphosphates (dI) and deoxyuridine triphosphate (dUTP) may be employed.

Polymerase enzymes are reviewed in Watson, J. D., In: *Molecular Biology of the Gene,* 4th Ed., W. A. Benjamin, Inc., Menlo Park, Calif. (1987), which reference is incorporated herein by reference, and similar texts. Examples of suitable DNA polymerases include the large proteolytic fragment of the DNA polymerase I of the bacterium *E. coli,* commonly known as "Klenow" polymerase, *E. coli* DNA polymerase I, the bacterio-phage T7 DNA polymerase.

Where desired, "thermostable enzymes" may be employed. as used herein, a "thermostable enzyme" is an enzyme which can catalyze a reaction at temperatures of between about 50° C. to about 100° C. Exemplary thermostable polymerases are described in European Patent Appln. 0258017, incorporated herein by reference. Thermostable "Taq" DNA polymerase is available from Cetus, Corp.

Examples of suitable RNA polymerases include *E. coli* RNA polymerase, T7 RNA polymerase, etc. Reverse transcriptases are discussed by Sambrook, J. et al. (In: *Molecular Cloning: A Laboratory Manual,* Cold Spring Harbor Laboratory Press, Cold Spring Harbor, N.Y. (1989)) and by Noonan, K. F. et al. (*Nucleic Acids Res.* 16:10366 (1988)).

The embodiments of the disclosed methods require a ligation event in order to achieve the amplification of the desired sequence. However, for purposes of identification of a particular nucleic acid sequence, non-amplification of the sample material is an equally important objective. I.e., for identification of, e.g., a specific, single-base mutation, two oligonucleotide moieties having a sequence complementary to the non-mutated version of the target sequence and designed to flank the mutation region will not be amenable to a ligation event if the target sequence includes the single-base mutation. Thus, in the foregoing non-limiting example, the absence of amplification can be viewed as an indicator of the presence of a mutation. As is evident, the disclosed invention can be used to, inter alia, amplify a target sequence and/or to identify the presence of a target sequence.

The ligation reaction needed for the amplification of the desired molecule will most preferably employ a "ligase" enzyme that is capable of covalently joining the 3' hydroxyl terminus of one oligonucleotide to the 5' $PO_4$ terminus of a second oligonucleotide. The kinetics of such ligation is greatly enhanced if the ligation substrate is double-stranded (as by having both oligonucleotides hybridized to the same target DNA or RNA molecule). Significantly, a ligase cannot join two oligonucleotides which do not have abutting termini when hybridized to their respective target molecule. Thus, although a ligase can "repair" a "nick" in a strand, it cannot "fill in" a "gap." In alternative embodiments, non-enzymatic ligation methods, such as chemical reactions, photochemical reactions (e.g. photocoupling; see, e.g. PCT Patent Appln. WO 90/01069, incorporated herein by reference), thermochemical, redox reactions, etc, can be used.

Beneficially for the purposes of the present invention, the kinetics with which a ligase can mediate the ligation of two oligonucleotides is greatly increased if the termini that are to be joined are correctly base paired to the target molecule. Thus, although ligation can occur at mismatched termini, the efficiency of such ligation is significantly less than that of oligonucleotides having properly base-paired termini. Preferred ligases include *E. coli* ligase, T4 ligase, and T7 ligase (Life Technologies, Inc. Gaithersburg, Md.). Where desired, thermostable ligases may be employed, such as that described in PCT Patent Appln. WO 91/17239, incorporated herein by reference.

All of the enzymes used in the amplification reactions of the present invention can be combined in the presence of a suitable buffer, such that the amplification process of the present invention can be done in a single reaction volume without any change of conditions such as addition of reactants.

Preferably, the ERA reaction takes place in a buffered aqueous solution, preferably having a pH of between about 6.0 and about 9.0. Preferably, the reaction buffer comprises various components which allow for the efficient and specific cycling of the ERA reaction. A particularly preferred buffering solution is 20 mM tris hydroxymethyl amino methane hydrochloric acid ("TRIS-HCl"), pH 7.8. Addition materials are preferably added to the reaction buffer; these materials are selected such that the cycling of the reaction is at high efficiency (e.g., the greatest amount of product per target template, preferably greater than 2x, more preferably $x^Y$, and most preferably about $x^2$, where x is the number of target templates available during each cycle, and Y is greater than 1.0 but less than about 2) and high specificity (i.e., the correctness of the fidelity of the ligase and polymerase enzymes, where "polymerase fidelity" is defined as the preference of the enzyme to catalytically incorporate the correct nucleotide and "ligase fidelity" is defined whereby ligase activity is limited to nick-closing activity, e.g., ligation of two complementary oligonucleotide moieties that are adjacent to each other when hybridized to a target sequence); processivity is maximized; catalytic stability of the enzyme (s) is maintained; and reaction stability (i.e. reaction components are maintained in solution; non-specific activity is decreased; adhesion of reaction components to the surface of the reaction vessel is minimized, etc.) is maintained. For the ERA protocol disclosed herein, the following components and amounts (final concentration) have been found to accomplish these goals: 20 mM potassium chloride; 2.0 mM magnesium chloride; 5.0 mM dithiothreitol ("DTT"); 50 $\mu$M nicotinamide adenine dinucleotide ("$NAD^+$"); 50 $\mu$g/ml bovine serum albumin; and 0.1% of a non-ionic detergent (e.g., Triton x 100™). These materials can be readily varied and adjusted depending upon the specific enzymes utilized; those skilled in the art are credited with readily selecting and optimizing such materials.

Other materials, such as preservatives and the like, can optionally be added to the reaction buffer. It is most preferred that double deionized water be utilized to achieve a desired final volume of the reaction buffer.

Typically, the temperature of the vessel is maintained at between about 30° C. and about 90° C., most preferably about 65° C. When heat denaturation is utilized, the temperature may increase above these values during the denaturation step. When heat denaturation is utilized (as is preferred), thermocyclers capable of providing a temperature controlled environment to the reaction vessel within a cyclical range of temperatures are preferably utilized. Exemplary is the Perkin Elmer 480™ thermal cycler.

Thus, though this process has several steps at a molecular level, operationally it may have a single step. Once the reactants are mixed together, one need not add anything or change conditions until the amplification reaction has exhausted one or more components. During this time, the nucleic acid sequence being amplified will have been increased many-fold. The level of increase will be sufficient for many purposes; however, for some purposes the reaction may have to be repeated with fresh components to achieve a higher desired level of amplification.

II. "ERA:" The "End-Run Amplification" Reaction

In its simplest embodiment, the method of the present invention uses three oligonucleotides to amplify the target sequence. The first and second of these oligonucleotides are designed such that their sequences are complementary to a portion of the target sequence. The third oligonucleotide is designed such that it is capable of hybridizing to a nucleic acid molecule having the sequence of the second oligonucleotide. The first oligonucleotide (designated "C" in the Figures) is termed the "Primer Oligonucleotide." The second oligonucleotide (designated "B" in the Figures) is termed the "Blocker Oligonucleotide." The third oligonucleotide (designated "A" in the Figures) is termed the "End-Run Oligonucleotide" primer. The nature and structures of these oligonucleotides is discussed in detail below. If desired, more than one set of Blocker Oligonucleotides, Primer Oligonucleotides and/or End-Run Oligonucleotides can be utilized as long as these are capable of amplifying different specific nucleic acid sequence(s).

In general, however, the oligonucleotides comprise any synthetic, semi-synthetic or natural nucleic acid fragment, or any chemical moiety capable of binding to a specific nucleic acid sequence in a specific manner and serving as a substrate for, e.g., an extension reaction or ligation event; exemplary chemical moieties are the so-called "Peptide Nucleic Acids" (see Egholm, M. et al., *J. Am. Chem. Soc.* 114:1895–1897 (1992), and Nielsen, P. E. et al., *Science* 254:1497–1500 (1991), which are incorporated herein by reference). An oligonucleotide typically comprises less than 150 nucleotides and/or chemical moieties. The nucleic acid can be deoxyribonucleic acid; derivatives of deoxyribonucleic acid; ribonucleic acid; or derivatives of ribonucleic acid.

Blocker, Primer and End-Run Oligonucleotides may be prepared using any suitable method using, e.g., the methods described in Beaucage, S. et al., *Tetrahedran Letters* 22:1859–1862 (1981). Commercially available instruments capable of generating oligonucleotide moieties are preferred, as these are widely utilized and typically time and cost effective. Exemplary instruments capable of generating defined oligonucleotides include, but are not limited to, the OLIGO 1000™ (Beckman Instruments, Inc., Fullerton, Calif.); Gene Assembler™ (Pharmacia, Uppsala, Sweden); Biosearch 8750™ (Milligen Biosearch, San Rafael, Calif.); and the ABI PCR Mate™ (ABE, Foster City, Calif.).

Any or all of the oligonucleotides can be labelled, and for many purposes, it is desirable that at least one of the oligonucleotides be labelled. Additionally, the dNTPs can be labelled. Beneficially, when the Blocker Oligonucleotide is labelled, the label can be conjugated to the 3' thereof such that the Blocker Oligonucleotide can hybridize with the target whereby elongation from the 3' end thereof is not possible; the rationale therefore will be delineated below. Alternatively, the 5' terminus of the End-Run Oligonucleotide may be labelled. Exemplary labelling protocols are well known; see, e.g., European Patent Appln. 292128, herein incorporated by reference.

Such labels can facilitate either the direct, proximal or indirect detection and/or capture of the amplified product. Additionally, two of the moieties can be part of a unitary structure such that only two oligonucleotide moieties are utilized in the amplification reaction. As used herein, a label that is directly detectable produces a signal which is capable of detection either directly or through its interaction with a substance such as a substrate (in the case of an enzyme), a light source (in the case of a fluorescent compound) or a photomultiplier tube (in the case of a radioactive or chemiluminescent compound).

Examples of preferred direct labels include radioisotopic labels, e.g., the use of oligonucleotides which have incorporated $^{32}P$, $^{35}S$, $^{125}I$, $^{3}H$, $^{14}C$. A particularly preferred approach for direct labelling of oligonucleotides is the "end-labelling" approach whereby T4 polynucleotide kinase is used to introduce a label into the 5' terminus of the oligonucleotide (See, e.g., Richardson, C. C., *The Enzymes*, Vol. XIV, Nucleic Acids Part A, Ed. Boyer, P. D., Acad. Press, p. 299 (1981)). Alternatively, terminal deoxynucleotidyl transferase can be utilized to add a series of supplied deoxynucleotides onto the 3' terminus of the oligonucleotide; single nucleotide labelling methods can also be used (See, e.g. Bollum, F. J. *The Enzymes*, Vol. X, Ed. Boyer, P. D. Acad. Press, (1974); Yousaf, S. I. et al., *Gene* 27:309 (1984); and Wahl, G. M. et al. *Proc. Natl. Acad. Sci. (U.S.A.)* 76:3683–3687 (1979). Labelled ddNTPs, e.g., [$\alpha^{32}P$] ddATP, can also be utilized.

In a research environment, where target amplification is not always performed on a continuing basis, utilization of radioactive labels may be preferred. In a non-research environment, e.g., in a clinical setting, such labels may not be preferred due to the disposal problem and allied risks associated with continued exposure to radioactive labels. Thus, indirect labels may be preferred in these settings. A label that is indirectly detectable does not in and of itself provide a detectable signal, however, it can be used to identify an oligonucleotide to which the indirectly detectable label is attached. Biotin, antibodies, enzymes, ferritin, antigens, haptens, etc. when conjugated to a dNTP or ddNTP comprise examples of indirectly detectable labels. Preferred non-radioactive direct labels include fluorescein-11-dUTP (see Simmonds, A. C. et al *Clin. Chem.* 37:1527–1528 (1991), incorporated herein by reference) and digoxigenin-11 dUTP (see Muhlegger, K. et al. *Nucleosides & Nucleotides* 8:1161–1163 (1989), incorporated herein by reference) can be utilized as labels. Additionally, non-radioactively labelled oligonucleotides, such as hapten labelled oligonucleotides may be used (See, e.g., Adams, C. W., PCT Patent Appln. WO 91/19729), which is incorporated herein by reference. A detection scheme involving such hapten-labels includes utilization of antibodies to the hapten, the antibodies being labelled.

Biotin is an especially preferred indirect label, whereby the detection of biotinylated nucleic acid molecules is accomplished using labelled or insolubilized avidin, streptavidin, anti-biotin antibodies, etc. Biotinylated molecules can also be readily separated from non-biotinylated molecules by contacting the molecules with insoluble or immobilized avidin.

In this regard, for example, biotin-11-dUTP can be utilized in lieu of dTTP, or biotin-14-dATP in lieu of DATP (See. generally, Langer, P. R. et al., *Proc. Natl. Acad. Sci. (U.S.A.)* 78:6633–6637 (1981), which is incorporated herein by reference). Biotinylated phosphoramidites can also be used (Misiura, K. et al. *Nucl. Acids. Res.* 18:4345–4354 (1990), which is incorporated herein by reference). Such phosphoramidites allows for precise incorporation thereof at desired locations along the growing oligonucleotide moiety during the synthesis thereof.

Chemiluminescent substrates can also be used as the indirect label. Enzymes, such as horseradish peroxidase ("HRP"), alkaline phosphatase ("AP"), etc. which can be directly cross-linked to nucleic acids may be employed (see, Renz, M. and Kurz, C. *Nucl. Acids Res.* 12:3435–3444 (1964), incorporated herein by reference). Luminal, a substrate for HRP, and substituted dioxetanes, substrates for AP, can be utilized as chemiluminescent substrates. Exemplary of the HRP labelling protocol is the ECL system available from Amersham (Arlington Heights, Ill., USA).

A further means for detection of amplified product includes utilization of nucleic acid probes which are complementary to the amplified product. For this type of detection, labelling of the oligonucleotide moieties is not necessary. If the target is present, amplification thereof will result in sufficient amounts of the target such that labelled nucleic acid probes can be used for detection. Single probes comprising directly or indirectly detectable labels can be utilized, or multiple probes comprising a directly or indirectly detectable label and capture moieties can be utilized. See, for example, U.S. Ser. No. 07/576,137 "Solution Phase Nucleic Acid Hybridization and Solid Phase Capture For Detection of Target Nucleic Acid, and Kit Therefore," which is incorporated herein by reference.

In lieu of direct or indirect labels, a proximity label may be employed. Such a label is a chemical moiety which produces a signal only in the presence of a second label which interacts with it. Typically, a first proximity label is used in combination with a corresponding second proximity label.

The reactant molecules are used in accordance with the methods described below to generate an amplification product. Typically, the amplification product will be double-stranded, and comprise both the desired sequence and its complement. Significantly, depending upon the sequences of the Blocker and the End-Run Oligonucleotides, it is possible to generate double-stranded molecules that are completely complementary to one another, or which have regions of non-complementarity. It is additionally possible to generate double-stranded molecules having either a protruding 3' terminus or a protruding 5' terminus.

Where it is desired to produce a nucleic acid that contains the desired sequence without producing any complementary nucleic acid molecule, the methods of the present invention may be adapted, as set forth below, to generate only such single-stranded molecules.

A. The "Primer Oligonucleotide" of the Present Invention

The first oligonucleotide of the invention, i.e. the "Primer Oligonucleotide" is a primer molecule, and thus must possess a 3' terminus which can be extended by a DNA polymerase. The oligonucleotide may be of any length ranging from about 5 nucleotides to several hundred. Preferably, the Primer Oligonucleotide will have a length of greater than 10 nucleotides, and more preferably, a length of from about 12–50 nucleotides. The length of the Primer Oligonucleotide must be sufficient to permit the Primer Oligonucleotide to be capable of hybridizing to the target molecule.

The sequence of the Primer Oligonucleotide is selected such that it is complementary to a predetermined sequence of the target molecule. This predetermined sequence may be a previously determined sequence (such as a gene, regulatory sequence, etc.) or may be a hypothetical sequence (such as a restriction endonuclease recognition site, a combination of such sites, etc.).

Preferably, the target sequence forms part of a coding region in a gene associated with a genetic disease, and the Primer Oligonucleotide's sequence is selected such that its extension will form a desired sequence that contains the genetic mutation that characterizes the disease. As described below, by suitably controlling the sequences of the oligonucleotides of the present invention, it is possible to diagnose or predict genetic disease in individuals whose gene sequences differ by as few one nucleotide from the corresponding sequences of these who do not have the disease.

In the more basic embodiments of the present invention, the sequence of the Primer Oligonucleotide of the invention determines the sequence of one terminus of the amplification product obtained by the invention. Thus, if the Primer Oligonucleotide is selected such that it is complementary to a desired gene sequence, the methods of the present invention permit the amplification of that gene sequence. Similarly, if the Primer Oligonucleotide sequence is complementary to a restriction site, a combination of restriction sites, a promoter site, or a regulatory protein binding site, then the methods of the invention permit the amplification of target sequences that contain these sites. Thus, in an alternate embodiment ("Blind ERA") the methods of the present invention permit one to amplify, for example, all promoter sequences which additionally contain thyroid hormone binding sites.

B. The "Blocker Oligonucleotide" of the Present Invention

The second oligonucleotide of the invention, i.e. the "Blocker Oligonucleotide," can be any length and is selected to be complementary to a portion of a target molecule. Although not essentail for carrying out the present invention, in one embodiment of the present invention, the Block Oligonucleotide is substantially incapable of serving as a primer. Thus, the 3' terminus of the Blocker Oligonucleotide is preferably modified to contain a "blocking group." Any compound which accomplishes this objective can serve as a "blocking group." Exemplary blocking groups are biotin, di-deoxynucleotide triphosphates ("ddNTPs"), also referred to as "chain terminating" ddNTPs. In several preferred embodiments, discussed below, the blocking group is detectably labelled. Additionally, it is possible to use a Blocker Oligonucleotide that "overhangs" the point of ligation with the Primer Oligonucleotide such that the, e.g., Blocker Oligonucleotide, is amenable to a "chew-back" reaction (see, for example, Holland et al., *Proc. Natl. Acad. Sci. (U.S.A.)* 88:7276–7280 (1991)).

The Blocker Oligonucleotide is preferably between about 10 to about 40 nucleotides; more preferably between about 15 and about 35 nucleotides, and most preferably about 23 nucleotides. However, the Blocker Oligonucleotide can be as small as two nucleotides in length (where the nucleotide at the 3' end comprises a blocking moiety); the length of the Blocker Oligonucleotide, therefore, can vary depending upon the experimental needs of the investigator and a recognition that the "$T_m$" decreases as the length decreases (i.e. preferential hybridization cannot be assured). "$T_m$" is the temperature at which 50% of the base pairing between two strands of a nucleic acid is disrupted. $T_m$ is a function of the length of single stranded DNA and the base composition thereof. Generally, for short oligonucleotide moieties (i.e. less than about 25 nucleotides) an approximate value of $T_m$ (in degrees Celsius) is equal to 4 times the number of G/C base pairs plus 2 times the number of A/T base pairs (i.e. 4(G/C)+2(A/T)).

Alternatively, the length and/or sequence of the Blocker Oligonucleotide can be adjusted such that the $T_m$ of the Blocker Oligonucleotide will be between about 37° C. and about 98° C.; more preferably between about 70° C. and about 90° C.; and most preferably about 85° C.

The Primer Oligonucleotide moiety is designed to hybridize upstream of the Blocker Oligonucleotide (i.e. in an orientation such that the 3' terminus of the Primer Oligonucleotide abuts, or can be extended to abut, the 5' terminus of the Blocker Oligonucleotide, when both molecules are hybridized to the (same strand of the) target molecule. In some embodiments of the invention, the 5' terminus of the Blocker Oligonucleotide is designed such that, when hybridized, the 5' terminal nucleotide of the Blocker Oligonucleotide will "oppose" a predetermined site in another nucleic acid molecule. As used herein, a nucleotide of a hybridized oligonucleotide is said to "oppose" another nucleotide if the two nucleotides are opposite one another in the hybridized product (i.e. positioned such that they would base pair with one another if they were complementary). A second function of the Blocker Oligonucleotide is to block the 3' terminus of the "Primer Oligonucleotide" from being extended past the 5' terminus of the Blocker Oligonucleotide.

The blocked 3' terminus of the Blocker Oligonucleotide defines the 3' terminus of the one strand of the amplification product. The 3' terminus of the Blocker Oligonucleotide will typically be capable of hybridizing to the target molecule. However, like the 5' terminus of the End-Run Oligonucleotide, the 3' terminus of the Blocker Oligonucleotide need not be capable of such hybridization. Thus, either or both of these termini may be designed to contain other desired nucleic acid sequences, such as restriction sites, binding sequences, etc.

Where the sequence of the target molecule has previously been determined, it is possible to design the Primer and Blocker Oligonucleotides such that, upon hybridizing to the target molecule, the 3' terminus of the Primer Oligonucleotide and the 5' terminus of the Blocker Oligonucleotide will abut. In this embodiment, a ligation event can occur between the Blocker and Primer Oligonucleotides without the need for primer extension.

Figure 2:
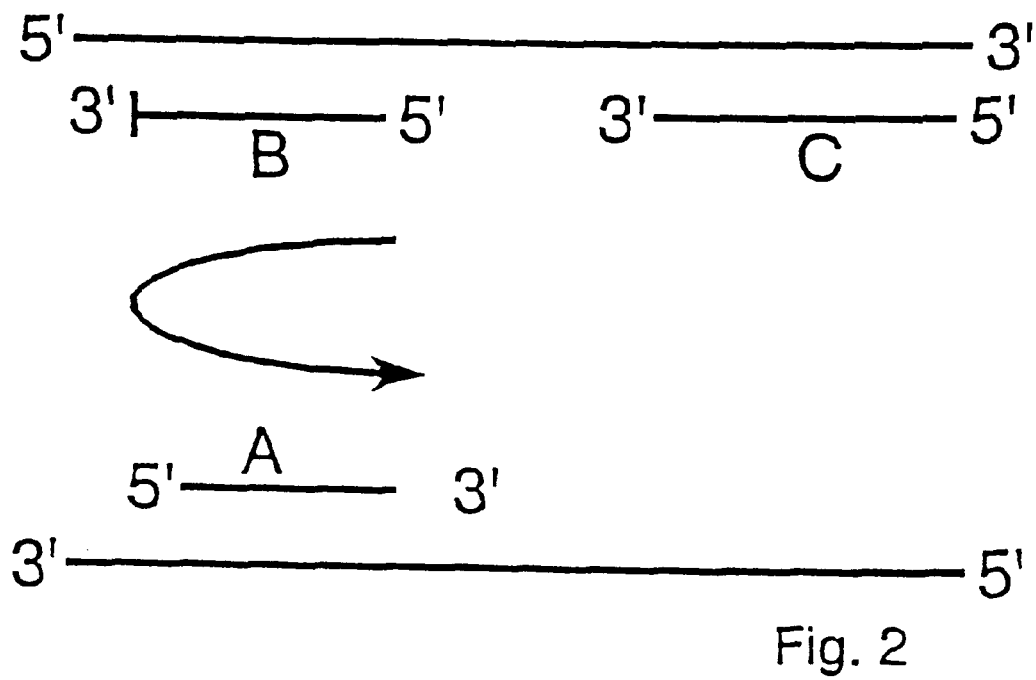
FIG. 2 provides a schematic representation of the positioning and characteristics of the "End-Run," "Blocker," and "Primer" oligonucleotides used to amplify a double-stranded target molecule in the "gap" ERA embodiment of the present invention.

Significantly, such a priori target sequence information is not required. Thus, the target sequence may be partially or fully undefined. In this embodiment, the Primer and Blocker Oligonucleotides are designed such that, upon hybridization to the target molecule, the 3' terminus of the Primer Oligonucleotide and the 5' terminus of the Blocker Oligonucleotide will be separated by a "gap" (which may contain either known or unknown sequences, or a combination of known and unknown sequences). Such a gap may be from 1 to about 10,000 nucleotides in length. In such an embodiment, ligation cannot occur unless the "gap" is "filled in," preferably by the polymerase-mediated, template-dependent extension of the 3' terminus of the Primer Oligonucleotide until such terminus reaches the 5' end of the Blocker Oligonucleotide; at that point, a ligation event between the Blocker Oligonucleotide and the elongated Primer Oligonucleotide can occur. FIG. 1 (double-stranded target) and FIG. 5 (single-stranded target) illustrate the relative locations of Blocker and Primer Oligonucleotides in the ERA embodiment in which the oligonucleotides abut. FIG. 2 (double-stranded target) and FIG. 6 (single-stranded target) illustrate the relative locations of Blocker and Primer Oligonucleotides in the ERA embodiment in which the oligonucleotides are separated by a gap.

In order to make the desired amplification dependent upon the ligation of the Blocker Oligonucleotide and the Primer Oligonucleotide (or its extension product), it is essential that the Blocker Oligonucleotide hybridize to a target sequence before the Primer Oligonucleotide, or before the primer extension product has been extended to a site beyond the site to which the 5' terminus of the Blocker Oligonucleotide can hybridize. If either of such events occurs first, the hybridized Primer Oligonucleotide can be extended along the region of the target to which the Blocker Oligonucleotide would otherwise hybridize, and even in the absence of a ligation event, a false-positive detection and amplification would result.

In order to avoid this scenario, it is preferred that the length of Primer Oligonucleotide be less than about 75% of the length of Blocker Oligonucleotide; more preferably less than about 60% of the length of Blocker Oligonucleotide; and most preferably less than about 50% of the length of Blocker Oligonucleotide. Alternatively, it is preferred that the $T_m$ of Primer Oligonucleotide be less than about 75% of the $T_m$ of Blocker Oligonucleotide; more preferably less than about 60% of the $T_m$ of Blocker Oligonucleotide; and most preferably less than about 50% of the $T_m$ of Blocker Oligonucleotide. By ensuring that the Primer Oligonucleotide is "shorter" than the Blocker Oligonucleotide, there is increased probability of Blocker Oligonucleotide hybridization occurring before Primer Oligonucleotide hybridization. An equivalent approach to satisfy the objective of hybridization of Blocker Oligonucleotide to the target before Primer Oligonucleotide is to add the moieties in a serial fashion with Blocker Oligonucleotide being added to the reaction mixture before Primer Oligonucleotide. Alternatively, it should be noted that the order of binding can also be controlled by altering the ratio and/or concentration of reactants. In "Loop ERA" (discussed below), preferential binding is addressed by using $T_m$ and proximity.

Those skilled in the art will appreciate that the length of an oligonucleotide moiety, which is important to the $T_m$ thereof vis-a-vis hybridization to a complementary sequence, can be manipulated in order to increase the "speed" of hybridization of the moiety to the complementary sequence. Thus, for example, given a target sequence having two regions of defined sequence, X and Y; a first oligonucleotide having a length X' complementary to region X; and a second oligonucleotide having a length Y' complementary to region Y, the first oligonucleotide will typically hybridize under more stringent conditions to the target "faster" than the second oligonucleotide when X'>Y'. This facet of oligonucleotide hybridization is amenable to efficient exploitation for the disclosed amplification procedure.

C. The "End-Run Oligonucleotide" of the Present Invention

The third oligonucleotide of the invention, i.e. the "end run" primer is a primer molecule, and thus must possess a 3' terminus which can be extended by a DNA polymerase.

The sequence of the End-Run Oligonucleotide is selected such that its 3' terminus is complementary to a predetermined sequence of the Blocker Oligonucleotide, or, less preferably, to a sequence that is created by the extension of the Primer Oligonucleotide. The predetermined complementary sequence of the Blocker Oligonucleotide most preferably includes the 5' terminal nucleotide of the Blocker Oligonucleotide; an internal sequence will, however, also be suitable.

The complementary 3' terminal sequence of the End-Run Oligonucleotide must be of sufficient length to permit hybridization between the 3' terminal sequence of the End-Run Oligonucleotide and a complementary sequence of the Blocker Oligonucleotide. The sole constraint of the End-Run Oligonucleotide is that its 3' terminus be substantially incapable of hybridizing with the Primer Oligonucleotide. Preferably, however, the 3' terminus of the End-Run Oligonucleotide does not extend beyond the 5' end of the Blocker Oligonucleotide when the two hybridize with each other. In the embodiment of the invention as depicted in FIG. 1, and in situations where a ligation event cannot occur, an End-Run Oligonucleotide whose 3' terminus extends past the 5' end of the Blocker Oligonucleotide could also hybridize with a region of the 3' end of the Primer Oligonucleotide (or its extension product), and thus extend along the Primer Oligonucleotide; in the case of an embodiment of the invention as depicted in FIG. 2, a spurious PCR reaction can occur even in the absence of the defined target, leading to false positive results. I.e., this event might allow the Primer Oligonucleotide to "prime" an extension reaction which results in the production of a product comprising a "copy" of the End-Run Oligonucleotide, if the 3' end of the End-Run Oligonucleotide overlaps and hybridizes with the 3' end of the Primer Oligonucleotide , ligation between Primer and Blocker Oligonucleotides could occur, independent of the presence of a specific target.

The length of the End-Run Oligonucleotide may thus be less than, equal to, or greater than the length of the Blocker Oligonucleotide. As such, it is preferred that the total length of the End-Run Oligonucleotide be between about 50 and about 100% of the length of the Blocker Oligonucleotide; more preferably between about 75% and about 95% of the length of the Blocker Oligonucleotide, and most preferably about 80% of length of Blocker Oligonucleotide. Alternatively, it is preferred that the $T_m$ of End-Run Oligonucleotide be between about 50% and about 100% of the $T_m$ of Blocker Oligonucleotide; more preferably between about 75% and about 95% of the $T_m$ of the Blocker Oligonucleotide; and most preferably about 80% of the $T_m$ of the Blocker Oligonucleotide. Additionally, it is most preferred that the 3' end of End-Run Oligonucleotide be flush with the 5'-end of Blocker Oligonucleotide so that the consequences of an End-Run "overhang", as described above, are effectively avoided. It is noted that the 5'-end of the End-Run Oligonucleotide need not be flush with the 3'-end of Blocker Oligonucleotide.

Although the 3' terminus of the End-Run Oligonucleotide must be capable of hybridizing to the Blocker Oligonucleotide, it is not necessary that the internal or 5'terminal sequences of the End-Run Oligonucleotide be similarly complementary to sequences of the Blocker Oligonucleotide. Thus, whereas in a preferred embodiment, the entire End-Run Oligonucleotide will be capable of hybridizing to the Blocker Oligonucleotide, in alternative embodiments the End-Run Oligonucleotide will be designed such that it contains internal or 5' terminal sequences that are substantially incapable of hybridizing with the Blocker Oligonucleotide. Such a capacity has great utility, since, as described in detail below, it provides a facile means for purifying one strand of the amplification product from another. Similarly, it permits one to simultaneously deduce the sequences of both strands of a double-stranded amplification product.

III. Overview of The "End-Run Amplification" Reaction

Although the following discussion is illustrated by reference to the amplification of double-stranded DNA (or DNA-RNA hybrids), it is to be understood that the discussion is equally applicable to the amplification of RNA, single-stranded DNA, or to mixtures of any of the foregoing types of nucleic acids.

The simplest embodiment of the "End-Run Amplification" ("ERA") reaction of the present invention comprises incubating the target molecule in the presence of the Blocker Oligonucleotide, such that the Blocker Oligonucleotide hybridizes to a complementary sequence of the target. After this has been accomplished, either the Primer Oligonucleotide or the End-Run Oligonucleotide can be added. The most preferred order of oligonucleotide hybridization to the target sequence strands are as follows: Blocker Oligonucleotide, then End-Run Oligonucleotide, then Primer Oligonucleotide. In preferred embodiments, the order can be Blocker, then Primer Oligonucleotide, then End-Run Oligonucleotide and Blocker Oligonucleotide or End-Run Oligonucleotide and Primer Oligonucleotide. As is evident, it is preferred that the Blocker Oligonucleotide be the first oligonucleotide to hybridize to the target. Such orders of addition are illustrative, and in no way limiting of the invention. As is evident, unless unused reactants are removed from the reaction, all will be immediately available at each stage of every subsequent round of amplification. If, however, sequential addition is desired in such subsequent amplification rounds, the unused Oligonucleotides may be removed or separated from the reaction at the conclusion of an amplification cycle, and then subsequently re-added in the desired sequence for a subsequent round of amplification.

Most preferably, the ratio of Blocker oligonucleotide to Primer Oligonucleotide to End-Run Oligonucleotide within the reaction vessel is $\geq 1:1:1$. However, variations are possible. Preferably, the Blocker Oligonucleotide should be present at a concentration which is equal to or greater than the concentration of the Primer Oligonucleotide , e.g., 1.5:1 or greater. Accordingly, it is most preferred that the amount of Primer Oligonucleotide not exceed the amount of Blocker Oligonucleotide; such a situation could increase the tendency of the Primer Oligonucleotide to hybridize with the target before the Blocker Oligonucleotide, a scenario which must be avoided, as will be set forth in detail below. The ratio of Blocker Oligonucleotide to End-Run Oligonucleotide can vary from the preferred 1:1 ratio without affecting the ERA protocol. The scenario to be avoided is the titration of the Blocker Oligonucleotide by the End-Run Oligonucleotide such that Blocker Oligonucleotide is not sufficiently available when the Primer Oligonucleotide hybridizes to the target sequence. This scenario can be avoided by adjusting cycle time, reaction temperature, $T_m$, oligonucleotide lengths, concentration of the target or by adjusting the ratio of Blocker Oligonucleotide to End-Run Oligonucleotide. It is preferred that of these factors, the Blocker Oligonucleotide to End-Run Oligonucleotide ratio be adjusted to avoid the foregoing scenario as this factor, relative to the others, is more readily controlled. Preferably this ratio is $\geq 1:1$.

Where there is a gap separating the hybridized Primer Oligonucleotide from the hybridized Blocker Oligonucleotide, a polymerase is added, along with dNTPs, and the reaction is maintained under conditions suitable for catalyzing the polymerase-mediated, template-dependent extension of the Primer Oligonucleotide. The "gap" between the hybridized Blocker Oligonucleotide and the hybridized Primer Oligonucleotide can be of any nucleotide length. Where the length is great, the timing of the amplification cycles is regulated to ensure that sufficient time is provided to allow for extension of the Primer Oligonucleotide and its ligation to Blocker Oligonucleotide. However, and because it is generally preferred to decrease the time of each amplification cycle in order to maximize the production of amplified product within a reasonable time period, the distance between the 5' end of the Blocker Oligonucleotide and the 3' end of the Primer Oligonucleotide when both are hybridized to the target is preferably between about 2 to about 10,000 bases, more preferably between about 2 to about 1,000 bases, and most preferably between about 2 to about 200 bases. It is, of course, evident that more than one Primer Oligonucleotide can be utilized, i.e. additional Primer oligonucleotide(s) can be utilized which hybridize to a region of defined sequence within the gap. As indicated, once the Primer Oligonucleotide has been extended such that its 3' terminus abuts the 5' terminus of the Blocker Oligonucleotide, the present invention contemplates the ligation of the two oligonucleotides to one another.

Where the Primer and Blocker Oligonucleotides are designed such that, upon hybridization to the target, their respective 3' and 5' termini abut, then the oligonucleotides can be ligated to one another without the primer extension step.

At this stage, the reaction conditions are altered, such that strand separation occurs. Strand separation can be accomplished using any suitable denaturing method; these include utilization of physical, chemical or enzymatic means. A physical method of strand separation involves heating the nucleic acid until it is completely denatured; heat denaturation typically involves utilization of temperatures ranging from about 80° C. to about 105° C. (preferably about 95° C.) for between about 1 to about 10 minutes (preferably about 4–5 minutes). An additional physical method of strand separation involves altering the pH of the medium in which the double strands are located; pH denaturation typically involves utilization of a pH range of from about pH 11 to about pH 14 for between about 1 second to about 10 minutes. An enzymatic method of strand separation can rely upon utilization of enzymes referred to as helicases or the enzyme RecA, which has helicase activity and in the presence of ATP has been reported to denature double stranded DNA. Reaction conditions suitable for separating the strands of nucleic acids with helicases are set forth in *Cold Spring Harbor Symposia on Ouantitative Biology*, Vol. XLIII, "DNA Replication and Recombination (New York: Cold Spring Harbor Laboratory, 1978), B. Kuhn et al., "DNA Helicases", pp. 63–67, which is incorporated herein by reference. When heat denaturation is utilized (as is preferred), enzymes utilized in the ERA protocol are most preferably thermostable enzymes.

If the ligation reaction has occurred, then the Blocker Oligonucleotide and the Primer Oligonucleotide (or its extension product) will have been covalently joined into a single molecule (i.e. the "desired molecule").

As indicated, the End-Run Oligonucleotide has a 3' terminus whose sequence is complementary to a sequence of the Blocker Oligonucleotide. Hence, the single molecule resulting from the ligation of the Primer Oligonucleotide (or its extension product) and Blocker Oligonucleotide can serve as the template for the polymerase-mediated, template-dependent extension of the End-Run Oligonucleotide. To accomplish this, reaction conditions are altered such that interstrand hybridization can occur.

The extension of the End-Run Oligonucleotide generates a molecule whose sequence comprises the target sequence. As such, the Blocker and Primer Oligonucleotides can hybridize to the End-Run extension product, and thereby form a new "desired molecule."

As will be appreciated the above described cycle may be repeated as often as desired in order to produce the chosen level of amplification of the desired molecule. Since a product of one step becomes a substrate of another, the amplification mediated by the reaction cycles results in an exponential amplification of the desired sequence.

Accordingly, the present invention is particularly useful for amplifying sequences, either known or unknown, which are, e.g., indicative of a genetic disorder; in particular, the present invention is directed to the determination of the presence of single base defects in a polynucleotide sequence. Additionally, the present invention can be utilized for amplification of polynucleotides having a known sequence or having a partially unknown sequence, which allows for analysis (e.g., sequencing) of the amplified product.

After an amplification reaction has been performed, any of a variety of techniques known to the art may be adapted to permit or facilitate such detection without undue experimentation. Particularly advantageous in some situations is the capture of RNA amplification products by a DNA oligonucleotide complementary to an RNA sequence determined by the target sequence, the oligonucleotide being bound to a solid support such as a magnetic micro-bead, or a resinous support. Preferably, this oligonucleotide's sequence does not overlap with that of any oligonucleotide used to purify the target before the amplification. RNA:DNA hybrids thus formed may then be detected by antibodies (or fragments thereof), preferably labelled, that bind RNA:DNA heteroduplexes. Detection of the binding of such antibodies can be done by a number of methods well known to the art.

Alternatively, amplified nucleic acid can be detected by gel electrophoresis, hybridization, or a combination of the two, as is well understood in the art. Those in the art will find that the present invention can be adapted to incorporate many detection schemes.

Sequences amplified according to the methods of the invention may be purified (for example, by gel electrophoresis, by column chromatography, by affinity chromatography, by hybridization, etc.) and the fractions containing the purified products may be subjected to further amplification in accordance with the methods of the invention.

IV. Preferred General Procedures for Conducting The "End-Run Amplification" Reaction In accordance with the above-described overview of the general method of the invention, certain procedures have been found to be particularly preferred.

General parameters regarding preferred lengths and $T_m$ of the Blocker, Primer and End-Run Oligonucleotides are disclosed in detail above. In a particularly preferred embodiment, lengths (in nucleotides) are as follows: Blocker Oligonucleotide—23; Primer Oligonucleotide—10; End-Run Oligonucleotide—18. In a particularly preferred embodiment, $T_m$ (in °C.) are as follows: Blocker Oligonucleotide—85; Primer Oligonucleotide—45; End-Run Oligonucleotide—75.

It is most preferable to simultaneously add the Blocker oligonucleotide, Primer Oligonucleotide and End-Run Oligonucleotide reactants of the method to the reaction vessel. However, the reactants may be added serially, or in groups. When the oligonucleotides are to be added serially, it is preferred that the following orders be used: Blocker, End-Run, Primer; Blocker, Primer, End-Run; Blocker, End-Run and Primer; Blocker and Primer, End-Run; or Blocker and End-Run, Primer. Alternatively, the moieties can be added in any order or as a single admixture when the reaction vessel (comprising the target sequence) is maintained at about 4° C.—as those in the art appreciate, at this temperature, hybridization, and enzymatic activity, is substantially, and typically completely, prevented.

Because the lengths (and/or $T_m$) of oligonucleotide moieties are designed to increase the probability that the target will hybridize first with the Blocker Oligonucleotide, then with the Primer Oligonucleotide and lastly with the End-Run Oligonucleotide, the oligonucleotides are typically added such that the concentration of Blocker Oligonucleotide is greater than or equal to that of either Primer Oligonucleotide or End-Run Oligonucletide. Each moiety is present in a concentration ranging from about 10 nM (nanomolar) to about 400 nM; preferably from about 50 nM to about 300 nM; and most preferably about 100 nM. The optimum quantity of probe used for each reaction also varies depending on the number of amplification cycles which are performed. Optimum concentrations can be readily determined by those of ordinary skill in the art.

Generally, as is appreciated by those in the art, the stringency of conditions is dependent upon temperature, buffer(s) and related parameters; however, the temperature parameter is typically easiest to control and therefore is a preferred stringency parameter which when varied, can be utilized to optimize the performance of ERA. As noted, directly related to stringency mediated by temperature is oligonucleotide length—thus, the stringency conditions can be readily optimized by those in the art in accordance with the objective of having the Blocker Oligonucleotide hybridize to the target before the Primer Oligonucleotide and target molecules hybridize to one another.

Unless the Primer and Blocker Oligonucleotides have been designed to abut one another, a polymerase is used to extend the primer in the direction of the Blocker Oligonucleotide, until a ligatable substrate is obtained. If needed to extend the Primer Oligonucleotide, it is preferable that the polymerase enzyme in conjunction with dNTPs will be present in the reaction vessel before, during or after the moieties are admixed with the target sequence. Most preferably, the polymerase enzyme is a thermostable polymerase enzyme. A most preferred additional step involves admixing the polymerase to the reaction vessel which already includes the target sequence, dNTPs, and the reactant oligonucleotides. In lieu of such sequential additions, all of the reagents may be admixed in a reaction vessel, the temperature of which is maintained at about 4° C. in order to substantially prevent hybridization and enzymatic activity.

Because the amplification stage of ERA is dependent upon a ligation event as well as an extension event, it is preferred that the next step in the procedure be the ligation of the Blocker and Primer Oligonucleotides hybridized to the target. Thus, the means for covalently coupling the two molecules, preferably a ligase enzyme and most preferably a thermostable ligase enzyme, is present in the reaction vessel before, during or after the molecules are admixed with the target sequence. Most preferably, the ligase is added to the reaction vessel after the oligonucleotide moieties have been added thereto.

The next preferred step in the reaction is the polymerase-mediated, template-dependent extension of the End-Run Oligonucleotide hybridized either to a target strand or to a ligated Blocker—Primer Oligonucleotide. If a polymerase has not been previously added to the reaction vessel, such a polymerase is preferably added, under the same considerations regarding the addition of polymerase as discussed above.

A most preferred order of adding the reactant components is as follows: reaction buffer; target sequence; dNTPs; oligonucleotides; thermostable ligase enzyme; thermostable polymerase enzyme. Most preferably, the thermostable polymerase enzyme is added after a "hot start", i.e., a first "denaturation cycle" is conducted before the polymerase enzyme is added to the reaction vessel. As stated, most preferably, these components are maintained at approximately 4° C. until initiation of the amplification process is desired. The reaction components can be added to the reaction vessel manually or by means of a robotic, automated laboratory workstation capable of automatically adding a variety of reaction components to a reaction vessel(s). A particularly preferred robotic, automated laboratory workstation is the BIOMEK® 1000 (Beckman Instruments, Inc., Fullerton, Calif.).

After the reaction components are admixed, if, as is most preferred, the reaction vessel has been maintained at 4° C., the reaction vessel is subjected to a "hot start", i.e., the temperature is increased to about 95° C. for about 5 min., in order to completely denature the target sequence prior to initiation of ERA by the addition of polymerase enzyme. This is preferably followed by the amplification cycles. In any particular cycle, it is desired that at least one ligation event occurs between a Blocker Oligonucleotide and a Primer Oligonucleotide hybridized to a target, and at least one elongation of an End-Run Oligonucleotide hybridized to a target and/or a Blocker Oligonucleotide—Primer Oligonucleotide ligation product—however, as the amplification is substantially exponential, the number of such events dramatically increases after each cycle.

A cycle requires annealing of the oligonucleotides to their respective targets, and denaturation therefrom. Thus, if denaturation is mediated by temperature (as is most preferred), the cycles are regulated by adjusting the temperature of the reaction vessel. If a non-thermostable enzymes are utilized, then as the temperature necessary to denature the strands is achieved, it is substantially possible for the enzymatic activity of the enzymes to be destroyed; thus, fresh enzyme may need to be added after each cycle. It is principally for this reason that thermostable enzymes are preferably utilized.

The temperature utilized within each cycle is principally dependent upon the $T_m$ of the oligonucleotide moieties. Oligonucleotides of about 6 to about 10 bases in length have a $T_m$ of about 40° C., at which temperature heat-sensitive (i.e. non-thermostable) enzymes are active. However, it longer oligonucleotides are used, the $T_m$ will increase, and necessitate the use of thermostable enzymes or the addition of heat-sensitive enzymes after each cycle. For the most preferred oligonucleotide lengths (Blocker Oligonucleotide—23 bases; Primer Oligonucleotide—10 bases; End-Run Oligonucleotide—18 bases), each cycle is most preferably defined by the following parameters: 95° C.—1 minute; 70° C.—4 minutes; 40° C.—4 minutes.

The number of cycles is principally dependent upon the needs of the investigator. Typically, detectable results can be achieved after as little as between about 10 to about 20 cycles. However, cycles in excess of 20 can be utilized if the reaction will not be limited by the concentration of oligonucleotides, dNTPs and enzyme present in the reaction vessel.

After the appropriate number of cycles is performed, the reaction may be stopped. This may efficiently be done by inactivating the enzyme and can, most preferably, be accomplished by lowering the temperature of the reaction vessel to 4° C. However, other approaches can be used, e.g., EDTA and a urea "stop" dye. Additionally, the enzymes can be chemically inactivated using methods known to those in the art, or the components can be separated: on, e.g., Sephadex™ columns; by filtration; by centrifugation; or by gel electrophoresis.

A potentially fatal problem associated with any amplification protocol is contamination; this problem is particularly acute when the amplification protocol is being used for diagnostic purposes. For example, even modest contamination from one reaction vessel can lead to erroneous positive results, i.e., a desired target, which is present in first vessel but not in a second vessel, may be accidently transferred from the first vessel to the second vessel—thus, the second vessel will evidence amplification of the desired target when, in fact, that target was not originally present in the second vessel. Various approaches for substantially reducing the possibility of such contamination have been proffered. One such approach involves utilization of the enzyme uracil-N-glycosylase ("UNG"). UNG degrades uracil such that oligonucleotides comprising uracil, in the presence of UNG, are effectively degraded. Additionally, UNG can be inactivated with heat (i.e., about 80° C.). Thus, when concerns regarding contamination are attenuated, a preferred solution is to replace dTTP with UTP in the reaction mixture, such that the amplified products incorporate uracil in lieu of thymidine. After amplification of the target in the first vessel, UNG is added to the second vessel; if any amplified product from the first vessel has contaminated the second, the UNG will effectively degrade the contaminant. Thereafter, the second vessel is "hot-started" by heating the vessel to about 80° C., thereby inactivating the UNG. Thereafter, the dNTPs and/or enzymes can be added to the second reaction vessel for initiation of the ERA protocol.

V. The Exemplary Embodiments of the Present Invention, and Their Preferred Uses As those in the art will readily appreciate, the principal differences between the various embodiments illustrated below is predicated upon the needs of the investigator.

1. "Gapless" ERA

Figure 3A:
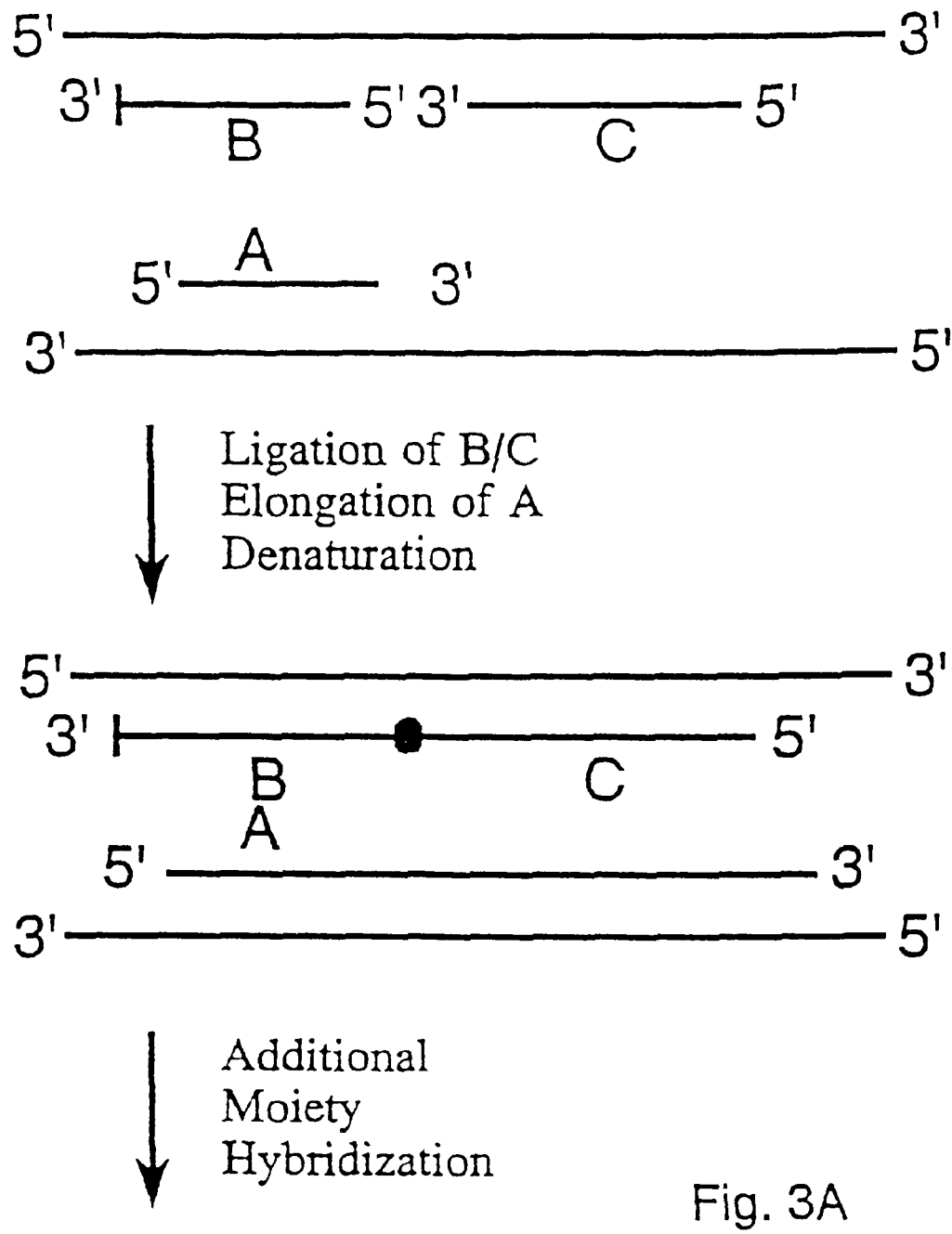
FIG. 3 illustrates the use of the "gapless" ERA embodiment of the End-Run Amplification method to amplify a desired double-stranded target molecule. The oligonucleotides are as defined in FIG. 1.
Figure 3B:
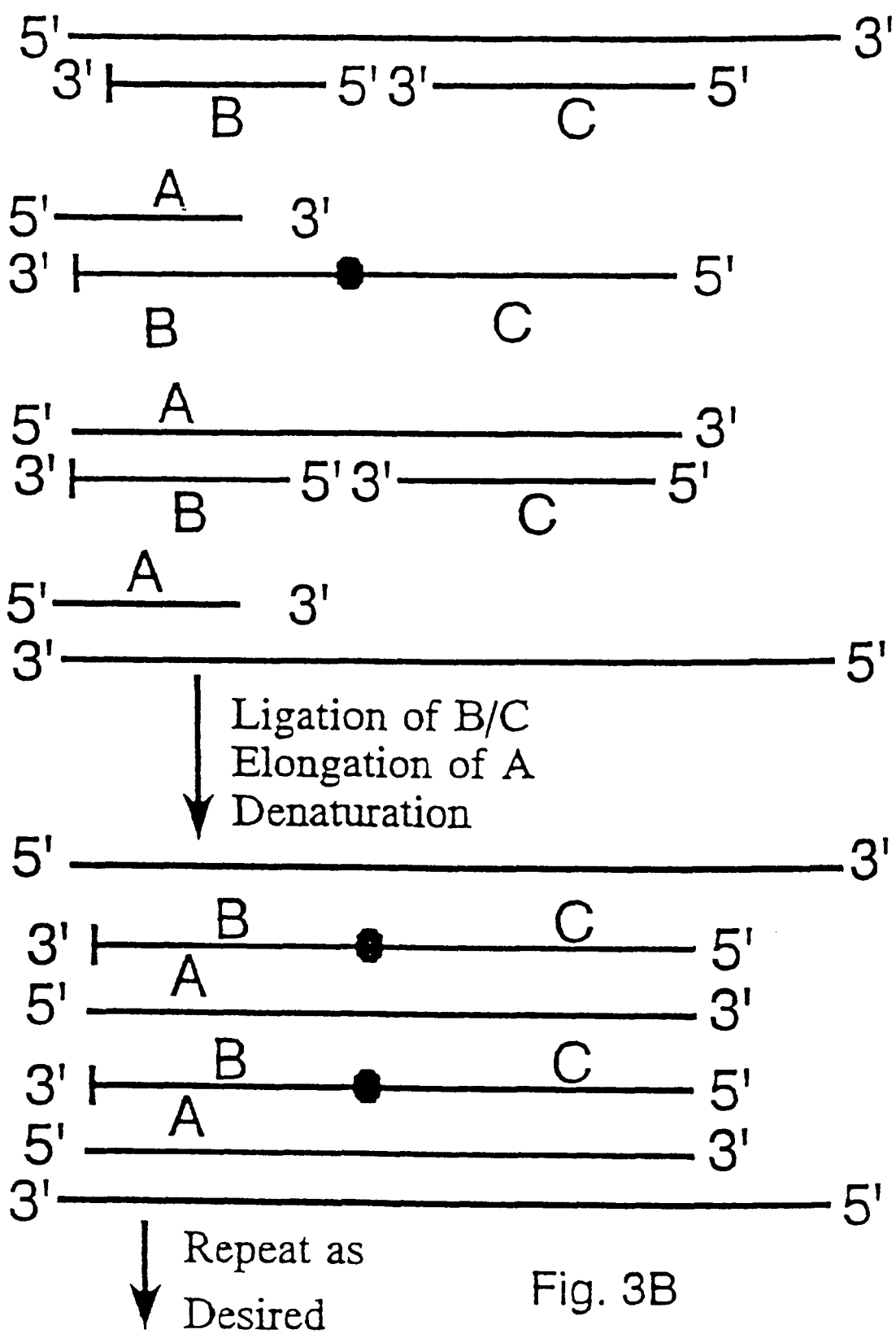

The "gapless" ERA embodiment is one in which the 3' terminus of the hybridized Primer Oligonucleotide is immediately adjacent to (i.e. abutting) the 5' terminus of the hybridized Blocker Oligonucleotide. In this embodiment, the template mediated extension of the Primer Oligonucleotide is not required. This aspect of the invention is conducted in accordance with the above-described general ERA procedures, and is illustrated in FIG. 1 and FIG. 3 (double stranded nucleic acid) and in FIG. 5 (single stranded nucleic acid).

Since the hybridized Primer and Blocker Oligonucleotides must abut in this embodiment, the practice of this embodiment requires the a priori determination of at least part of the target nucleic acid sequence. Such information is needed in order to define sequence of the Blocker and Primer Oligonucleotides. The Blocker and Primer Oligonucleotides need not necessarily be designed to hybridize completely along the target; rather, sufficient detail regarding the target sequence must be known such that the 5' terminus of the Blocker Oligonucleotide and the 3' terminus of the Primer Oligonucleotide can hybridize thereto under stringency conditions. Alternatively, the target sequence can be isolated in sufficient quantity to enable production of sufficient oligonucleotide complementary pairs for utilization in the disclosed process.

This embodiment of the invention is particularly suited for identifying genetic mutation or polymorphic sites. Most preferably, in this regard, the sequence of the Primer Oligonucleotide will be selected such that its 3' terminal nucleotide corresponds to either the "normal" or the "mutant" allele that is to be identified. As will be appreciated, if the Primer Oligonucleotide terminates with the "normal" base, that base will not hybridize to a target sequence derived from an individual having a mutation at that site. Accordingly, amplification by ERA will occur only if the sample was derived from a "normal" individual. Conversely, by using a primer that terminates in the "mutant" base, or in a "promiscuous" base such as inosine, it is possible to adapt the reaction such that amplification will occur only if the sample was derived from a "mutated" gene sequence.

2. "Gap" ERA

As indicated above, in a second preferred embodiment of the invention, Blocker and Primer Oligonucleotides are employed which, when hybridized to a target molecule are separated by a gap of between 1 and 10,000 bases. Significantly, the presence of this gap permits the use of this embodiment of the invention even in situations in which minimal sequence information is available. In particular, the sequence of the gap can be unknown; what is necessary is that sufficient detail regarding portion(s) on either side of the gap must be known such that complementary Blocker and Primer Oligonucleotides can be generated.

Figure 4A:
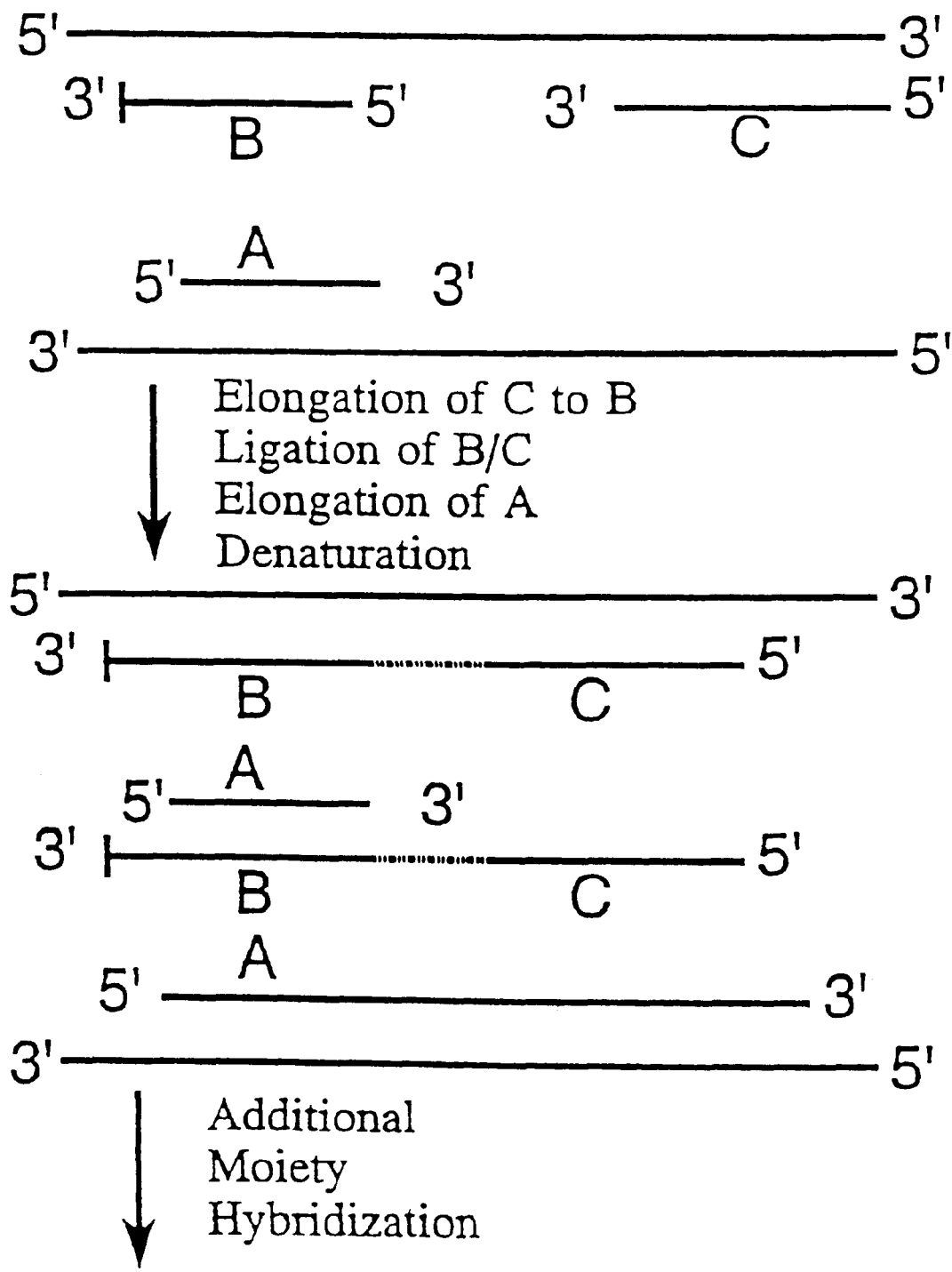
FIG. 4 illustrates the use of the "gap" ERA embodiment of the End-Run Amplification method to amplify a desired double-stranded target molecule. The oligonucleotides are as defined in FIG. 1.
Figure 4B:
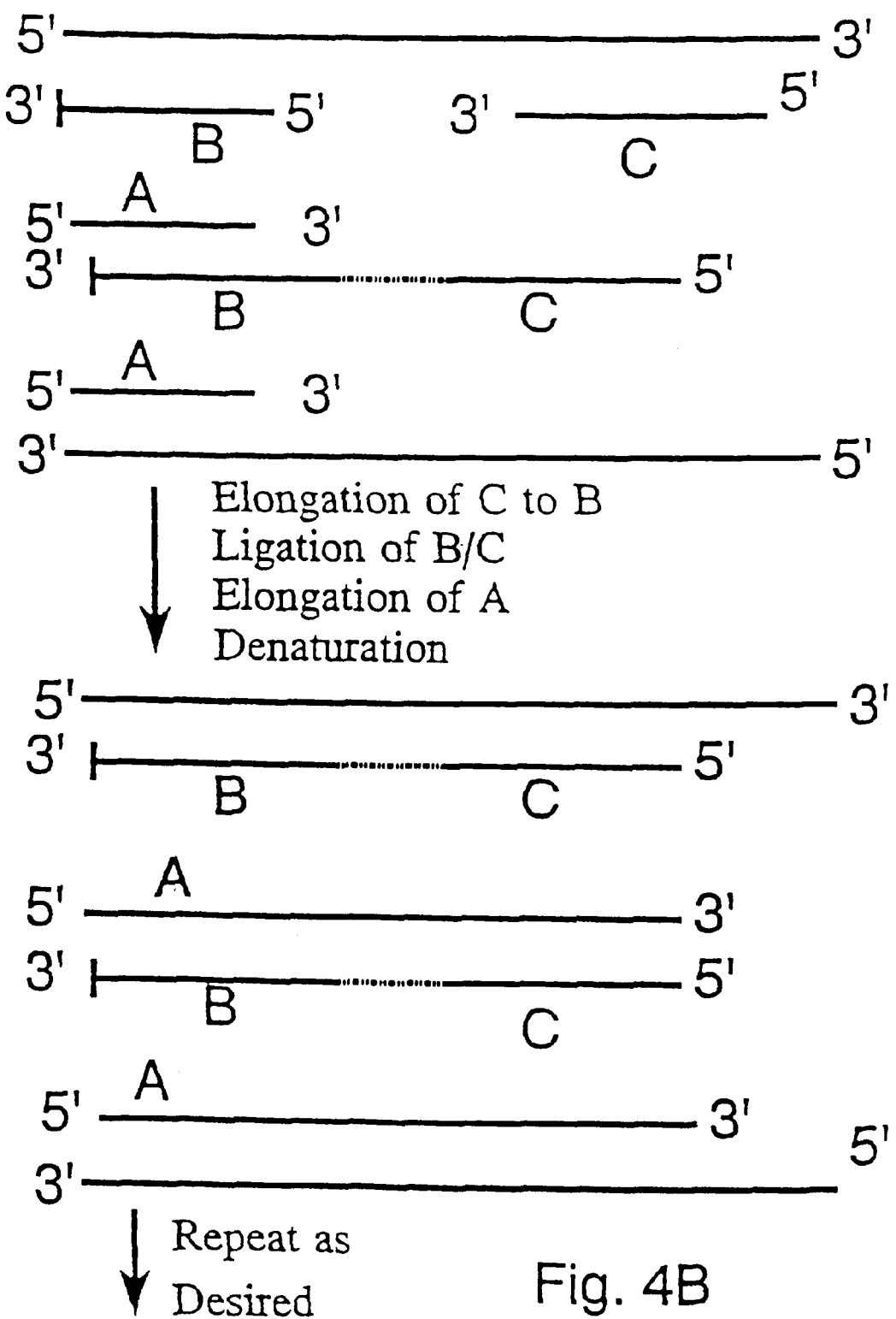
Figure 5A:
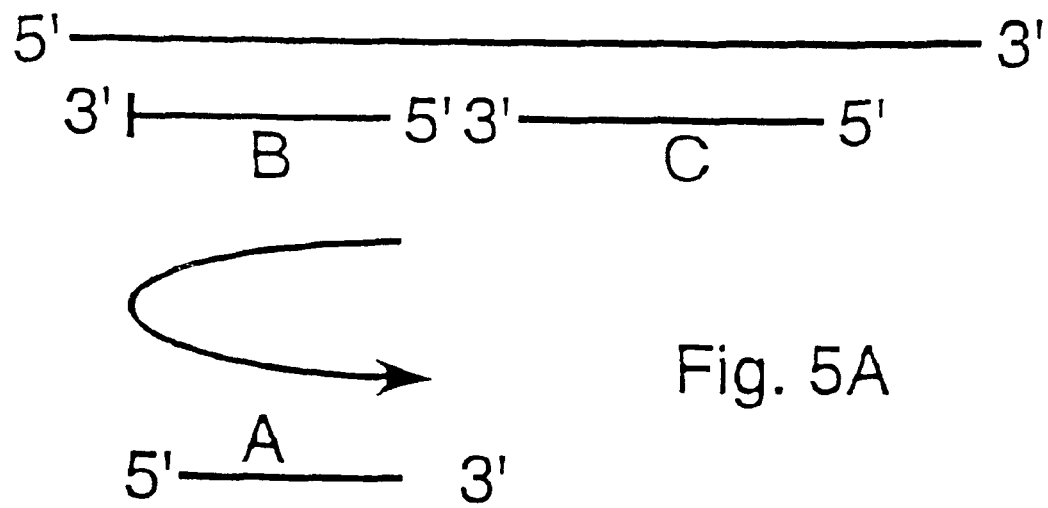
FIG. 5A provides a schematic representation of the positioning and characteristics of the "End-Run," "Blocker," and "Primer" Oligonucleotides used in the "gapless" ERA embodiment of the present invention with respect to a single-stranded target molecule.
Figure 5B:
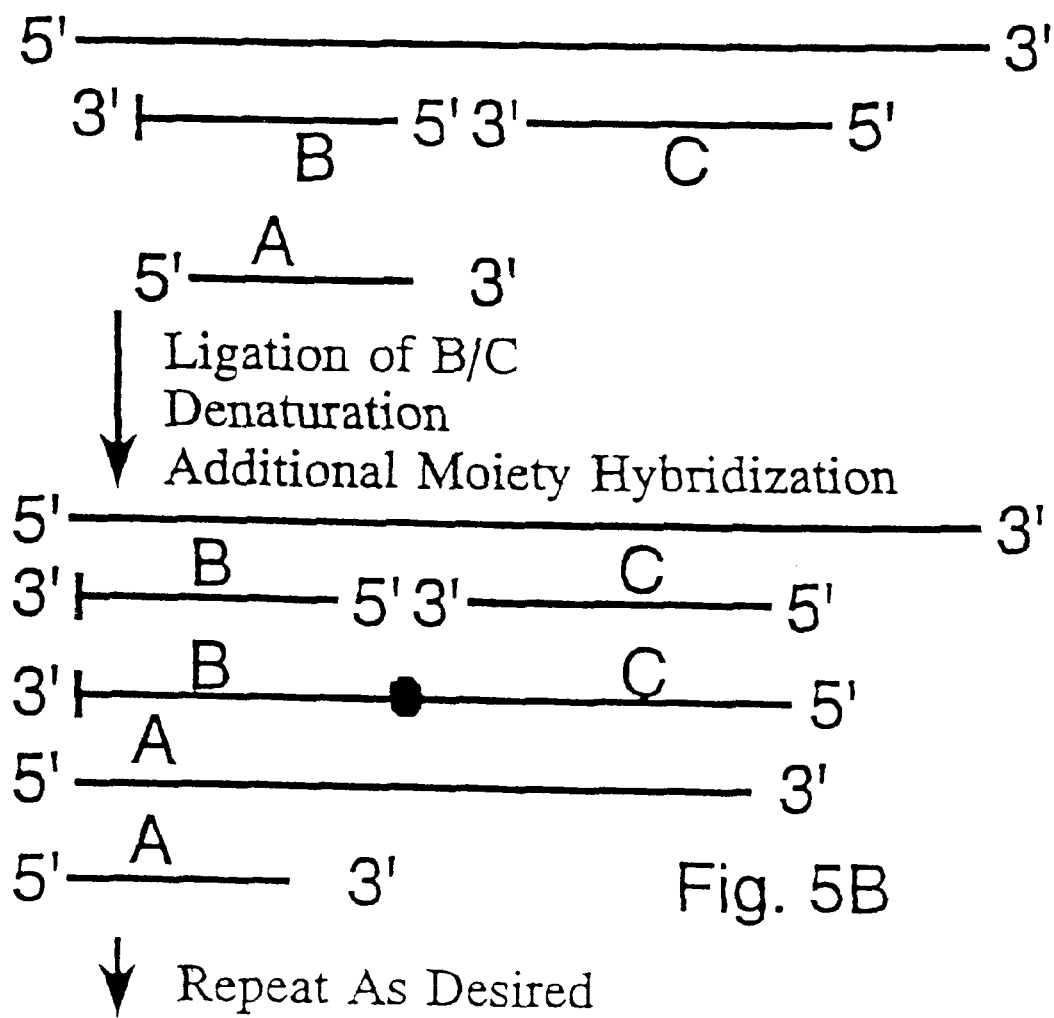
FIG. 5B illustrates the use of the "gapless" ERA embodiment to amplify a desired single-stranded target molecule.
Figure 5C:
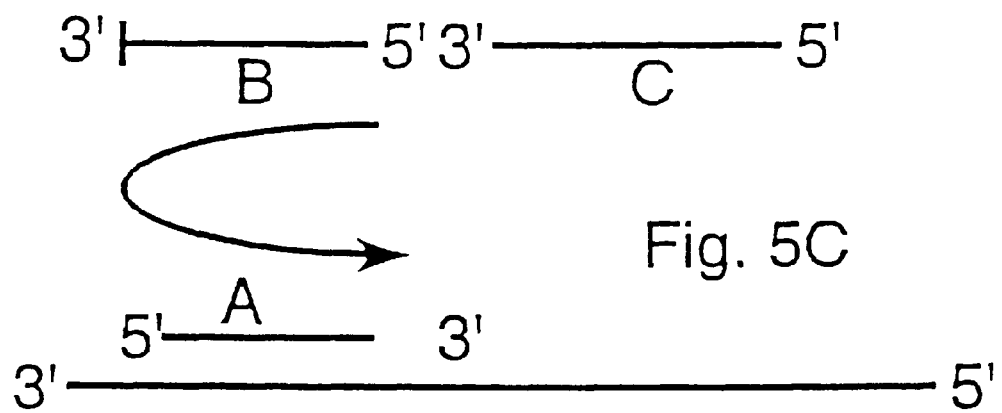
FIGS. 5C and 5D illustrate the amplification of a single-stranded target molecule when the End-Run Oligonucleotide is extended before the ligation of the Blocker and Primer Oligonucleotides. The molecules are as defined in FIG. 1.
Figure 5D:
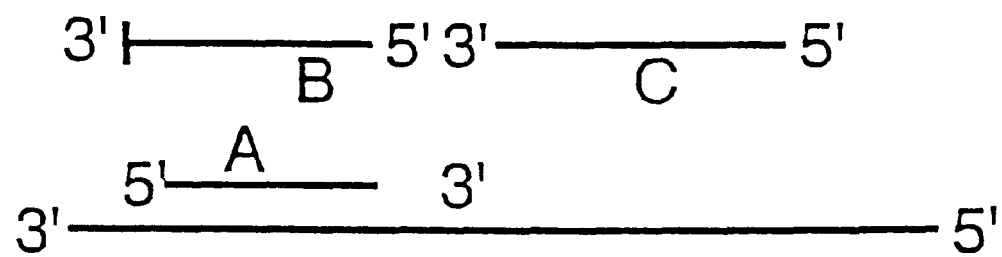
Figure 5D:
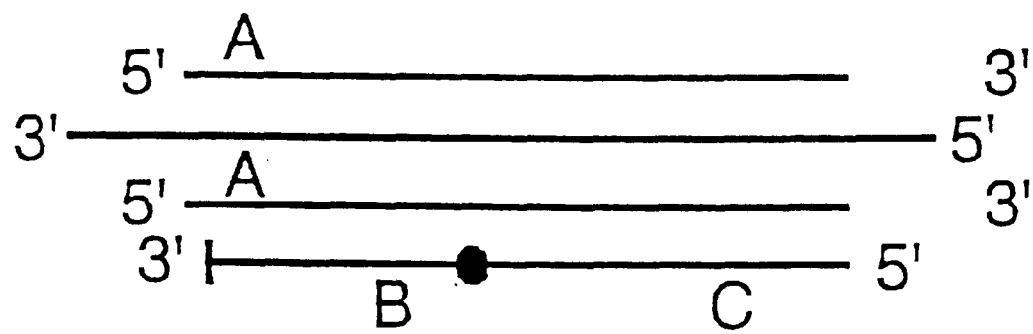
Figure 5D:
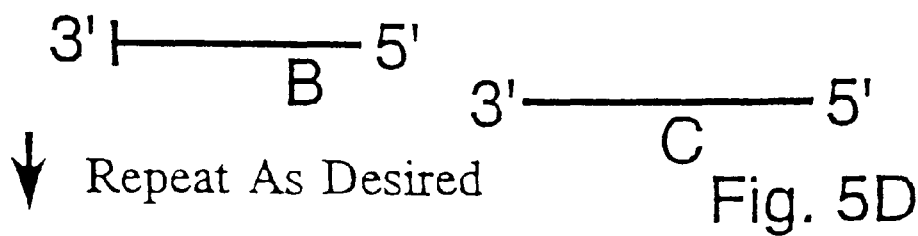
Figure 6A:
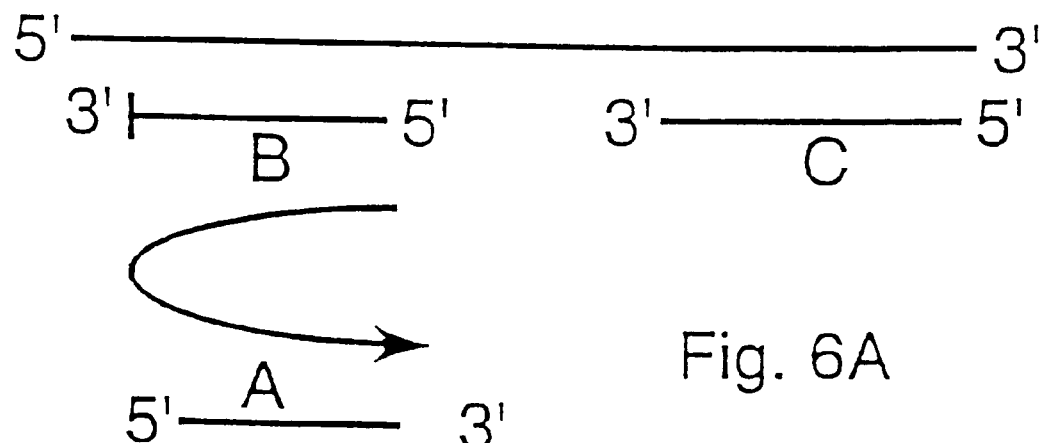
FIG. 6A provides a schematic representation of the positioning and characteristics of the End-Run, Blocker, and Primer Oligonucleotides used in the "gap" ERA embodiment of the present invention with respect to a single-stranded target molecule.
Figure 6B:
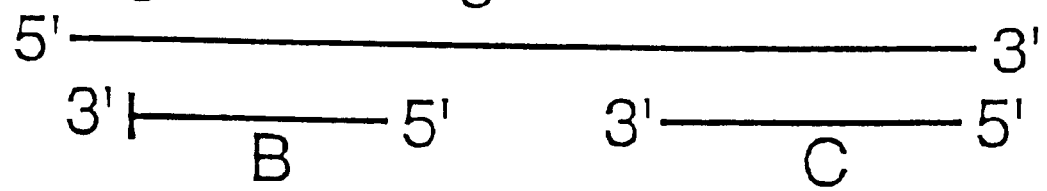
FIG. 6B illustrates the use of the "gap" ERA embodiment to amplify a desired single-stranded target molecule.
Figure 6B:
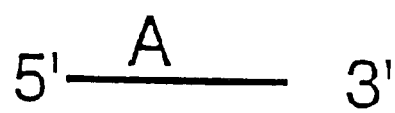
Figure 6B:
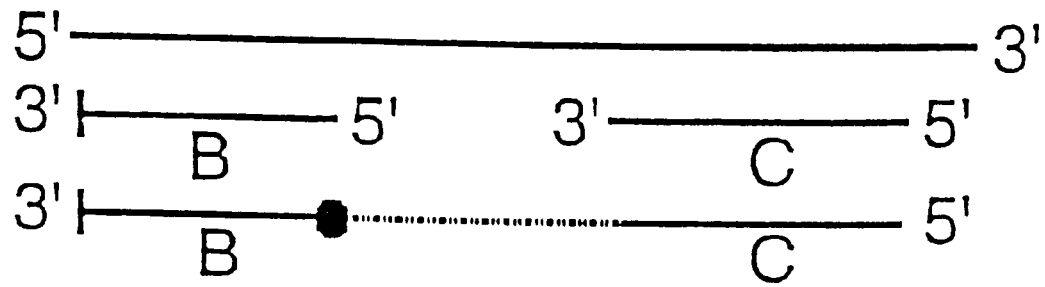
Figure 6B:
Figure 6C:
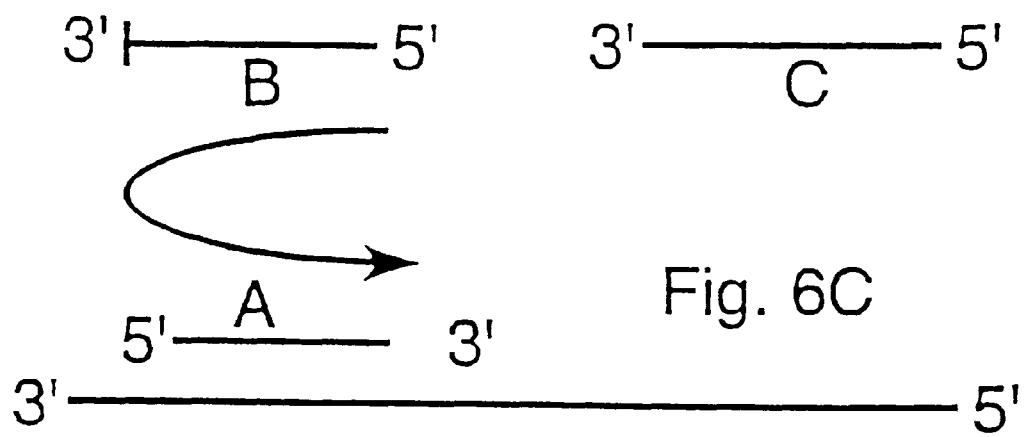
FIGS. 6C and 6D illustrate the amplification of a single-stranded target molecule when the End-Run Oligonucleotide is extended before the ligation of the Blocker and Primer Oligonucleotides. The molecules are as defined in FIG. 1.
Figure 6D:
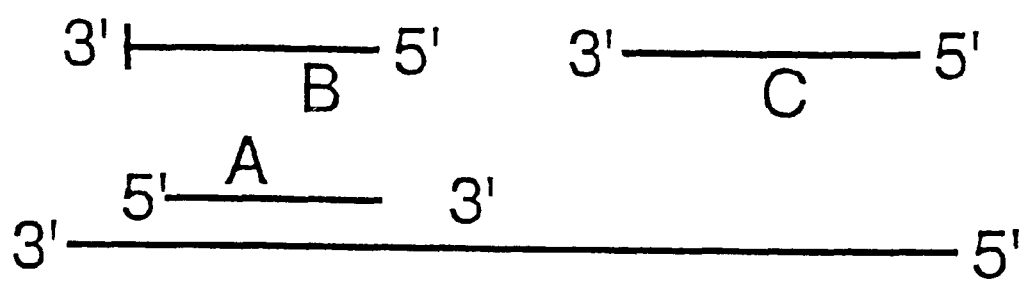
Figure 6D:
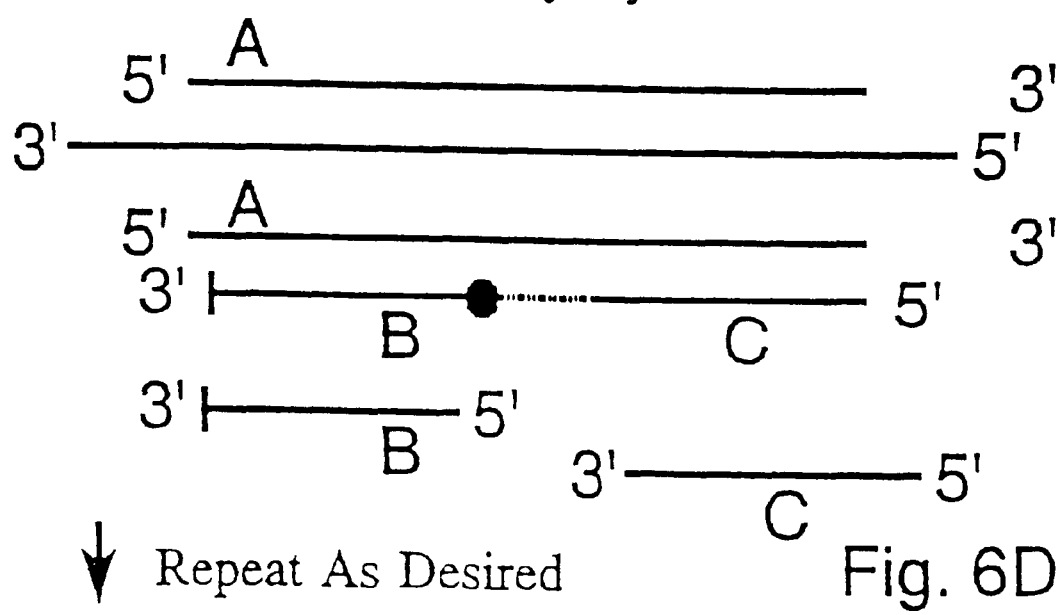

The "gap" ERA embodiment of the present invention is illustrated in FIG. 2 and FIG. 4 for double stranded nucleic acid molecules, and in FIG. 5 for single stranded nucleic acid molecules.

The "gap" ERA embodiment of the present invention is conducted in accordance with the above-described general ERA procedures, however, for gaps exceeding about 200 nucleotides in length, it is preferred that the reaction time for each cycle be increased; preferably, each cycle should be greater than about 10 minutes, i.e. greater than about 12–15 minutes. The intent of such increase is to increase cycling efficiency. The time course of the reaction is preferably minimized so as to increase the velocity of amplification as much as possible without affecting reaction efficiency.

For gaps of greater than 10,000 bases, one or more additional Primer Oligonucleotides may be used (such optional additional Primer Oligonucleotides are referred to as "Primer.A," "Primer.B," "Primer.C," etc.). Where a Primer.A is to be employed, such is designed such that it contains a sequence that can hybridize to a portion of the gap (whose sequence is known or partially known). Thus, if the gap is exceedingly large (i.e., greater than about 10,000 nucleotides), it may be desirable to use a Primer.A (or additional Primer Oligonucleotide species) to hybridize to a site, preferably at the approximate middle of the gap (or at a variety of sites if multiple primers are employed), in order to facilitate the elongation of the Primer Oligonucleotide, through Primer.A (and any other Primer Oligonucleotides) to the 5' terminus of the Blocker Oligonucleotide. Upon ligation, the Primer Oligonucleotide, Primer.A, and the Blocker Oligonucleotide become covalently linked to one another thereby forming the template for the End-Run Oligonucleotide in the reaction. The procedural steps of the "gapless" ERA embodiment are equally applicable to "gap" ERA. This embodiment of the invention is particularly suited for amplification of target sequence(s) comprising a region(s) of fully or partially unknown sequence, the ligation event occurs after elongation of the Primer Oligonucleotide(s) up to a point immediately adjacent to the Blocker Oligonucleotide, whereupon a ligation event can occur.

Although the above-described detection methods are equally applicable to this embodiment of the invention, it is preferable when practicing this embodiment of the invention to detect amplification using nucleic acid probes which are complementary to one (or more) of the oligonucleotides; this would allow for "pulling" amplicons from the reaction vessel, whereby sequencing thereof can be accomplished.

In diagnostic applications, this embodiment of the invention provides the opportunity to utilize a variety of labelled probes directed to specific mutations that lead to one or more alleles. I.e., for a variety of mutations known to exist within a particular region of a gene, the Blocker Oligonucleotide(s) and Primer Oligonucleotide(s) can be designed to flank this region; amplification of the target will then generate amplicons of undefined mutations. Specific probes directed to the known mutational sequences can then be utilized to screen the amplicons such that, depending on which probe hybridizes with the amplicons, identification of the mutation can be accomplished.

This embodiment of the invention can also be used to facilitate the detection and amplification of genes related to genetic diseases. Unlike the "gapless" embodiment of the invention, in this embodiment the Blocker and Primer Oligonucleotides need not be immediately adjacent to each other upon hybridization to the target. Thus, for example, the embodiment may be used in the case of a genetic disease that is characterized by a variety of alleles (such as deletions, insertions, rearrangements, as well as point mutations) caused by a variety of mutational changes in defined regions of the gene, the Blocker and Primer Oligonucleotides can be created such that they flank this region upon hybridization to the target. The extension of the Primer Oligonucleotide, and the ligation of the blocker to the Primer extension product, permits the End-Run Oligonucleotide to amplify the target sequence corresponding to the polymorphic site. Thereafter, the amplified product can be sequenced, or probes (directed, for example, to each of the various mutations that can occur in the "gap" region) can be used to screen the amplified product to determine which mutation is or is not present in a particular sample.

This embodiment of the invention is also ideally suited for amplifying genomic or cDNA sequences in which only fragmentary sequence information is available. One method for amplifying cDNA or DNA using this embodiment requires only a knowledge of the amino terminal sequence of the expressed protein. This information can be used to define a Blocker Oligonucleotide that is capable of hybridizing to (all or a subset of) the codons that encode such a sequence, and an End-Run Oligonucleotide that is capable of hybridizing to the Blocker Oligonucleotide. The Primer Oligonucleotide molecule in this embodiment could comprise a poly-T sequence, such that the molecules together would amplify any cDNA or DNA sequence that encodes a protein beginning with the specified codons.

3. "NERA"—"Nested" ERA

The "NERA" or "Nested ERA" embodiment of the ERA protocol is a hybrid of "gap" ERA and "gapless" ERA. NERA is preferably conducted as a two stage amplification reaction. The first stage is designed to amplify a target sequence including a "quasi-gap," i.e. wherein the "gap" includes a region whose sequence has been substantially identified. The second stage is designed to amplify the quasi-gap of the first stage using, most preferably, molecules which, in relation to the reactant molecules of the first stage comprise a "nested" Blocker Oligonucleotide and a "nested" Primer Oligonucleotide which hybridize adjacent to each other.

Figure 7:
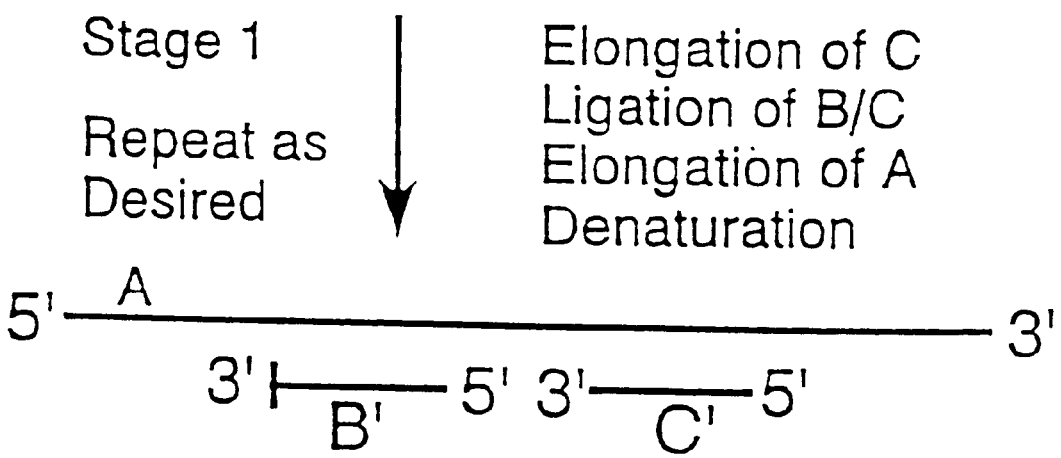
FIG. 7 illustrates the use of the "nested" ERA embodiment ("NERA") of the invention to amplify a double-stranded target molecule. The oligonucleotides are as defined in FIG. 1.
Figure 7:
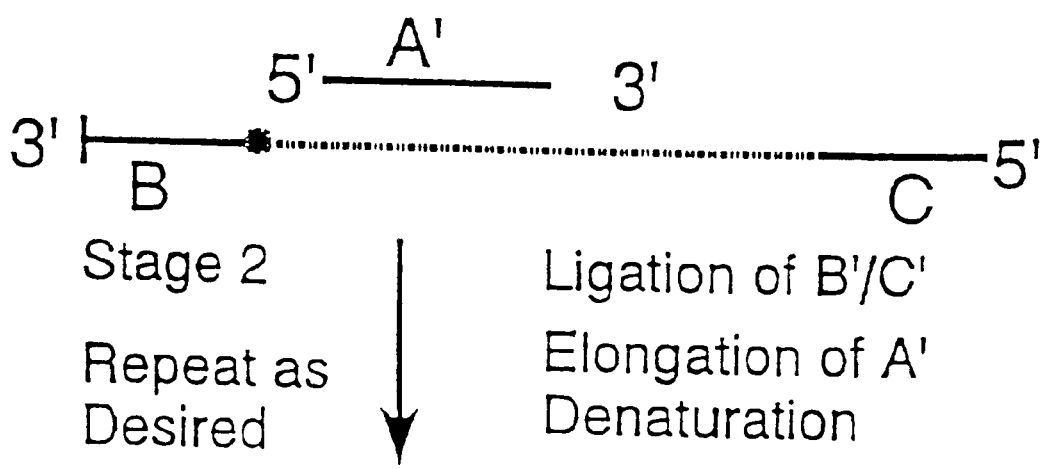
Figure 8A:
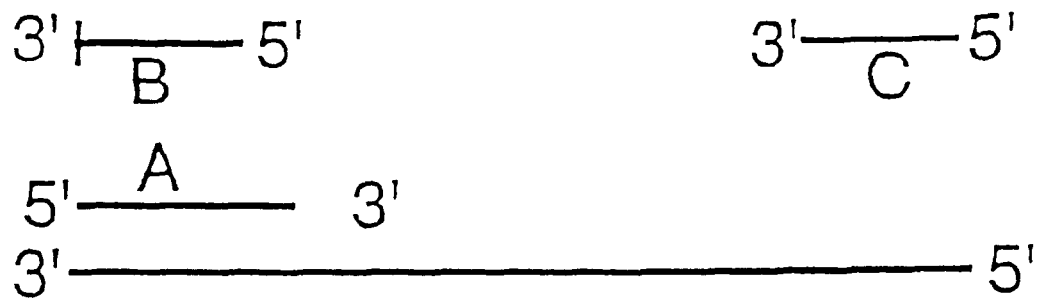
FIG. 8 illustrates the use of the "nested" ERA embodiment ("NERA") of the invention to amplify a single-stranded target molecule. The oligonucleotides are as defined in FIG. 1.
Figure 8A:
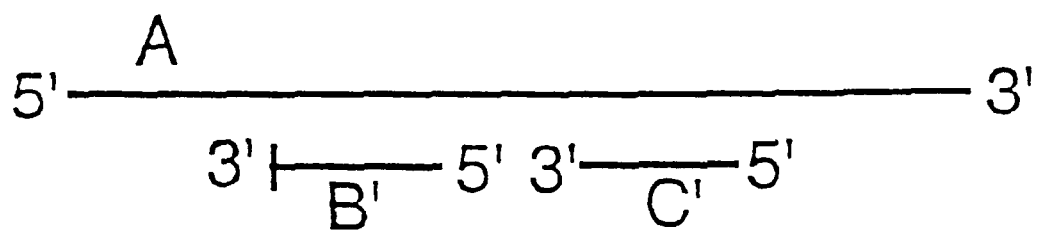
Figure 8A:
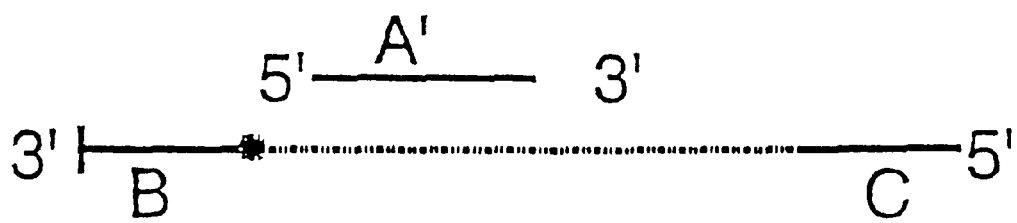
Figure 8B:
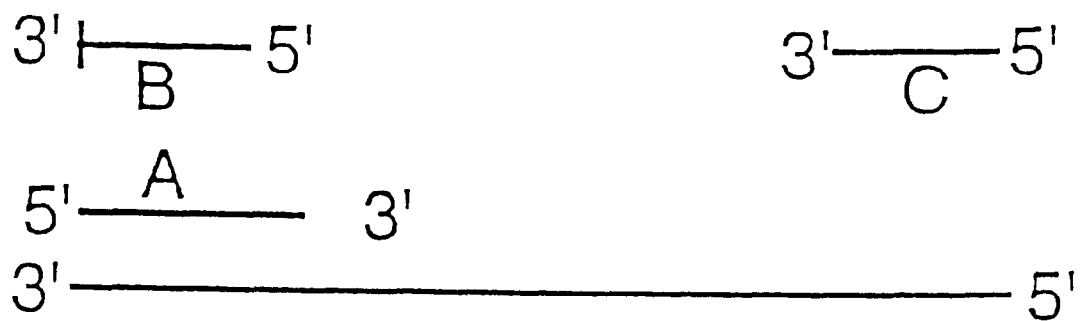
Figure 8B:
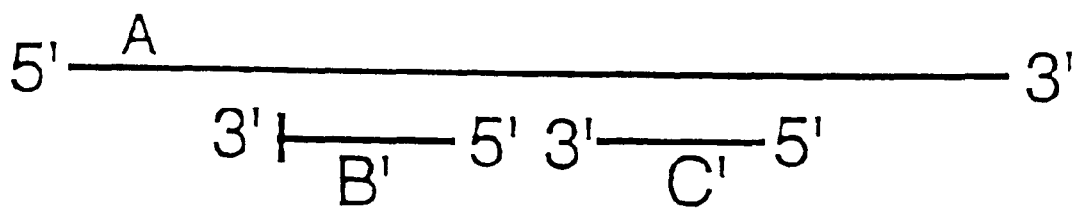
Figure 8B:
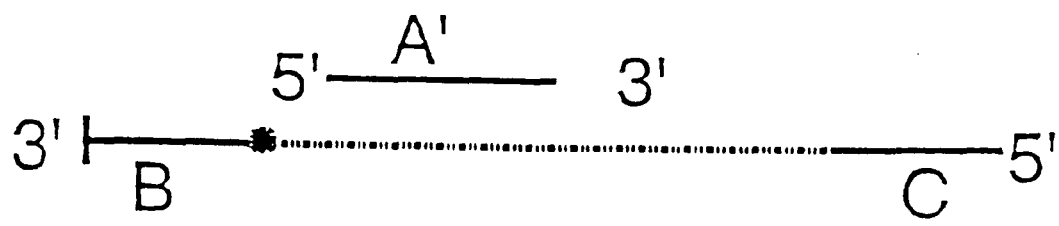

The NERA embodiment thus provides a protocol for determining whether or not spurious amplification has occurred (due to contamination, erroneous hybridization reactions or other causes). The NERA protocol is schematically set forth in FIG. 7 for double-stranded target molecules, and in FIG. 8 for single-stranded target molecules.

In the first stage of NERA, Blocker, Primer and End-Run Oligonucleotides are used in the same manner as described in "gap" ERA—i.e., the Blocker and Primer Oligonucleotides are designed to flank a gap section, the Primer Oligonucleotide is extended, such that it abuts the Blocker Oligonucleotide, and the molecules are ligated to one another via a ligase.

The amplification product of the first stage of the reaction is used as the target for the second stage of the reaction. Thus, in the second stage, the Blocker, Primer and End-Run Oligonucleotides may be considered to be "nested" with respect to their counterparts in the first stage. The second stage reactants are admixed with the amplified product from the first stage (along with, inter alia, ligase and polymerase enzymes and dNTPs). The nested Blocker and Primer Oligonucleotides are designed to hybridize with the "filled-in" portion of the gap of the original target. Such a design resolves any problem occasioned by spurious amplification from the first stage. Spurious amplification might occur in the first stage if, for example, the first stage Blocker and Primer Oligonucleotides had hybridized to non-specific "pseudo-target" regions during the first stage reaction. In such an occurrence, the filled-in gap would not correspond to the desired "target" gap, and hence could not be amplified by the nested Blocker and Primer Oligonucleotides of the second stage of the reaction. Thus, the NERA embodiment reduces the possibility of spurious amplification.

The NERA embodiment facilitates the detection of spurious amplification. If no such spurious amplification has occurred, i.e. if the Blocker and Primer Oligonucleotides of the first stage hybridized to the true target sequence, then the resulting amplified product can serve as a target sequence for the nested reactants of the second stage, and will accordingly be amplified by that reaction.

The general ERA procedures are also used in the NERA embodiment. The above-discussed considerations, features and characteristics of "gap" ERA are equally applicable to the first stage of NERA, except that, as noted, while a "gap" is utilized for NERA, the sequence within the gap must be of sufficient definition such that nested Blocker, Primer and End-Run Oligonucleotide can be generated which can hybridize to the filled-in portion of the amplified product of the first stage.

Because a preferred objective of the first stage is to generate sufficient target for the second stage, labelling is not required in the first stage—as is apparent, detection or capture is not per se necessary under these parameters. Labelling is preferred, however, for the second stage.

After sufficient cycling in the first stage (i.e. between about 5–80 cycles), the reaction can be stopped, preferably by temperature mediation (i.e. lowering the temperature to about 4° C.), and the second stage commenced. The amplified product of the first stage need not be separated from unused reactants which may be present in the reaction vessel. This is because to the degree that exponential amplification has occurred, the addition of the nested moieties to the reaction vessel will not compete with such unused reactants—the nested moieties, as defined, are designed to hybridize to regions along the amplified product and thus should not, under stringency conditions, hybridize with the unused reactants. However, the amplified products from the first stage can be separated from the unused reactants by, e.g. column chromatography, bio-specific affinity (biotin-avidin, e.g.), gel purification, etc.

The second stage of NERA is conducted in accordance with the above-discussed considerations, features and characteristics of "gapless" ERA. As noted, the amplification products of the first stage are preferably not labelled. In contrast, the amplification products of the second stage are preferably labelled, and detected, in the manner described above.

4. "LERA"—"Loop" ERA

In the "Loop ERA" or "LERA" embodiment of the invention, differs from previously described ERA embodiments in that in LERA the Blocker and Primer Oligonucleotides are tethered to one another, preferably via an oligonucleotide bridge. More specifically, the bridge connects the 3' terminus of the Blocker Oligonucleotide to the 5' terminus of the Primer Oligonucleotide, such that the resulting molecule can be described as a open circular, or "Loop" oligonucleotide The tethering of the Blocker Oligonucleotide to the Primer Oligonucleotide can be accomplished by any means which will not interfere with hybridization of the Blocker Oligonucleotide and Primer Oligonucleotide portions of the Loop to a designated target sequence under high stringency conditions, and which will not interfere with exponential amplification of the target sequence. Most preferably, tethering is accomplished using a sequence of "non-specific" nucleotides (i.e. a sequence not intended to be complementary to any section of the target sequence); beneficially, the use of such non-specific nucleotides allows for synthesis of the Loop during the preparation of the oligonucleotides, i.e. a single oligonucleotide is prepared comprising both the Blocker Oligonucleotide and Primer Oligonucleotide and a non-specific region.

The LERA embodiment is illustrated in FIG. 9. Most preferably, the Loop can most preferably be synthesized as a single strand; as schematically set forth in FIG. 9A, Blocker Oligonucleotide and Primer Oligonucleotide regions of the Loop are identified, the dashed lines representing the non-specific region (preferably nucleotides). The Blocker Oligonucleotide and Primer Oligonucleotide regions of the Loop are functionally equivalent to the Blocker and Primer Oligonucleotides discussed above.

Figure 9A:
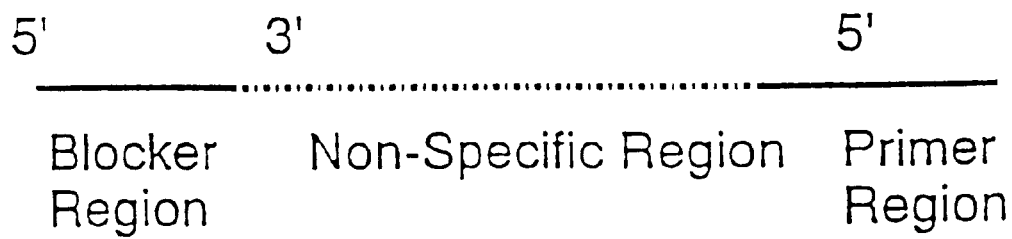
FIG. 9A illustrates the tethering of the Blocker and Primer Oligonucleotides.
Figure 9B:
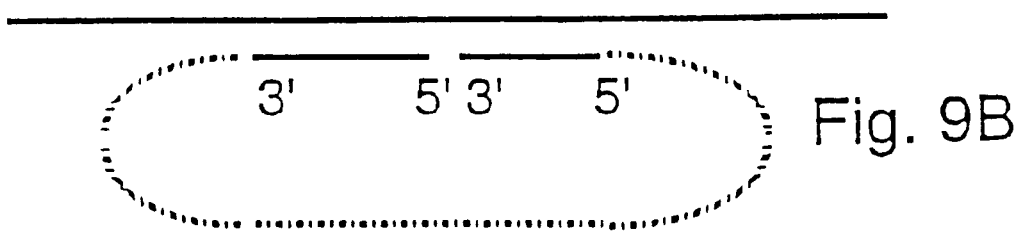
FIG. 9B provides a schematic representation of the Loop of 9A hybridized to a target sequence.

Because the Blocker Oligonucleotide and Primer Oligonucleotide regions of the Loop must be capable of hybridizing to the target such that the 5' end of the Blocker Oligonucleotide region abuts the 3' end of the Primer Oligonucleotide region or such that a gap is created between these regions, the non-specific region of the Loop must be of sufficient length to allow for hybridization of the Blocker Oligonucleotide and Primer Oligonucleotide regions to the target sequence in a manner consistent with this requirement. FIG. 9B schematically represents such hybridization, and as can be appreciated, when the Blocker Oligonucleotide and Primer Oligonucleotide regions hybridize to the target, a "Loop" comprising an opening is formed.

When the non-specific region is comprised of just nucleotides (as is most preferred), the length thereof is preferably greater than about 40 bases, more preferably greater than about 50 bases. When other linkers are utilized, such as, e.g., hydrophilic, linear or branched organic molecules such as a hydrophilic aliphatic linkers, the number of bases can correspondingly decrease. The functional intent of the non-specific region is to provide a sufficient tether that allows for (a) linkage of the Blocker Oligonucleotide region to the Primer Oligonucleotide region and (b) hybridization of the Blocker Oligonucleotide region and Primer Oligonucleotide region to their respective complementary regions on the target sequences(s).

Figure 9C:
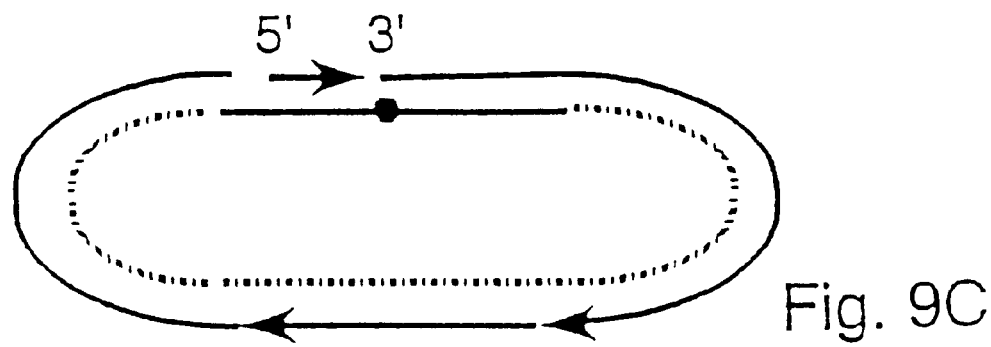
FIG. 9C provides a schematic representation of an End-Run extension reaction along the ligated Blocker Oligonucleotide and Primer Oligonucleotide regions of the Loop of 9A.

Upon hybridization of the Loop to the target sequence(s), in the case of a single stranded target, a ligation event or a Primer Oligonucleotide extension reaction followed by a ligation event, takes place (if appropriate vis-a-vis the target and the defined sequences of the Blocker Oligonucleotide and Primer Oligonucleotide regions of the Loop). This is followed by separation of the completed Loop from the target. The End-Run Oligonucleotide, which consistent with the general characteristics of ERA is most preferably complementary to a segment of the Blocker Oligonucleotide region, is then capable of hybridizing to the completed Loop, and extended along the Loop in a polymerase-mediated, template-dependent extension reaction. FIG. 9C provides a schematic representation of the hybridization of the End-Run Oligonucleotide to the completed Loop, and the elongation of the End-Run Oligonucleotide.

Figure 9D:
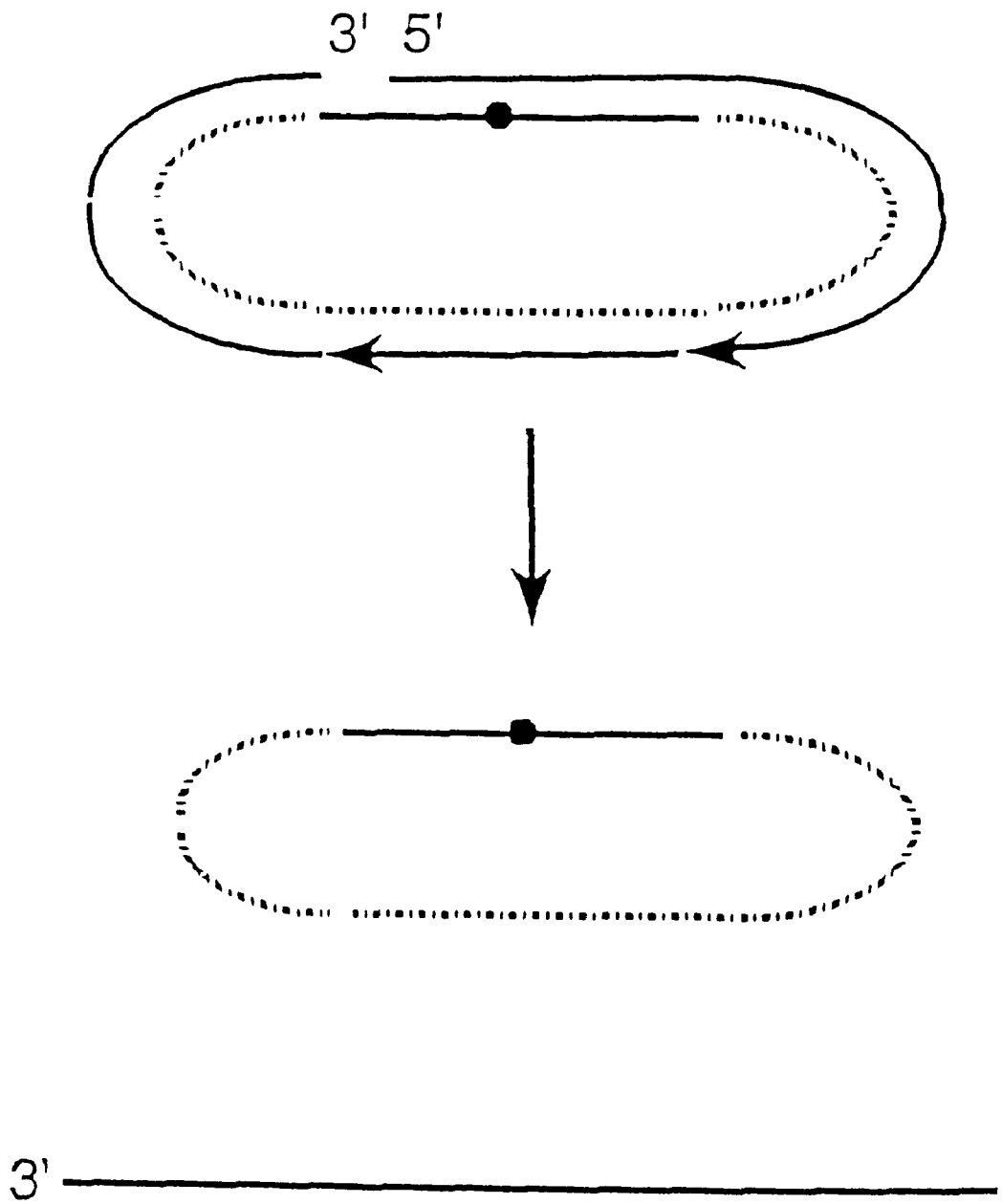
FIG. 9D provides a schematic representation of the resulting target derived from FIG. 9C.

Significantly, the presence of ligase enzyme within the reaction vessel can catalyze a ligation event between the 5' end of the End-Run Oligonucleotide, and the 3'-end of its extension product, and thereby generate a covalently closed double-stranded circular molecule. Since the strands of such a molecule may be difficult to separate, the formation of such a molecule may impair the exponential amplification of the target molecule. To avoid this possibility, it is preferable to incorporate a ligation blocking group at the 5' terminus of the End-Run Oligonucleotide. If such a group is present, then, under denaturing conditions the elongated End-Run Oligonucleotide will serve as a template comprising regions complementary to the Blocker Oligonucleotide and Primer Oligonucleotide regions of the Loop, thereby facilitating exponential amplification. FIG. 9D schematically represents the separation of the End-Run extension product from the completed Loop.

LERA can also be used where the target is a double-stranded molecule. Moreover, since the End-Run Oligonucleotide can also hybridize with a section of one of the target strands, elongation of the End-Run Oligonucleotide along the target strand occurs.

In some sub-embodiments of LERA, the non-specific bridge region of the Loop is modified to incorporate regions that possess desired features. For example, the bridge may contain one or more restriction sites, such that the cloning, or sequencing of the amplified molecule is facilitated. Significantly, such a restriction site may be used in lieu of adding the blocking group that is desirably added to the 5' terminus of the Blocker Oligonucleotide as an alternative means of ensuring against the formation of covalently closed double-stranded circular molecules. The bridge region may also contain modified bases, especially deoxyuridine, or ribonucleotides, such that the resulting molecule is amendable to degradation by, e.g., RNAse H, UDG and endonuclease IV, such that any ligation of the 3' and 5' termini of the End-Run extension product will "open" the enclosed Loop, thus forming a template for further amplification. Beneficially, thermostable RNAse H can be utilized. See, Itaya et al., *Nuc. Acids Res.* 19:4443–4449 (1991), which is incorporated herein by reference.

The non-specific bridge region can also be designed to incorporate a variety of different functional parameters. For example, hybridization capture regions can be incorporated into the region in order to facilitate the recovery of the amplified product.

Significantly, the bridge region may contain origin of replication sequences, such that the amplification product may be clonally replicated upon transformation into a suitable host. In such a sub-embodiment, blocking of the 5' terminus of the Blocker Oligonucleotide is unnecessary. The bridge region may also contain gene sequences, especially gene sequences that encode selectable markers.

In yet another sub-embodiment, the bridge sequence may contain promoter or proto-promoter sequences (i.e. a sequence whose complement is a promoter), such that upon the extension of the End-Run Oligonucleotide, a transcriptionally active site is created that is capable of transcribing the target sequences. Preferred such sites include the T7 and SP6 RNA polymerase binding sites, which allow for transcription (in the presence of, e.g., RNA polymerase and ribonucleotide triphosphates). In this sub-embodiment, no blocking group is required, since closure of the End-Run extension product is not important.

Beneficially, a strand that is formed via RNA polymerase-mediated transcription is displaced from the Loop without the need for, e.g., heat denaturation. Thus, with the addition of RNA polymerase and ribonucleotide triphosphates, multiple copies of template will be generated from even a single closed Loop. This leads even greater exponential amplification (i.e. amplification at a higher exponent). Furthermore, because the amplified strands mediated by RNA polymerase are displaced without the need for denaturation, the cycling reactions can be run at isothermal temperatures, i.e. about 37° C. As will be appreciated, this allows for the use of non-thermostable ligase and polymerase, and avoids the need for thermocycling.

In using RNA polymerase mediated LERA, it is preferred that the ratio of RNA polymerase to ligase and/or DNA polymerase be at least about 5:1 or greater. Additionally, the ratio of total ribonucleotide triphosphates to total deoxyribonucleotide triphosphates is preferably at least about 5:1 or greater.

The bridge region may also contain a site-specific recombinational site, such as att or loxP sites (Weisberg, R. et al., In: *Lambda II*, (Hendrix, R. et al., Eds.), Cold Spring Harbor Press, Cold Spring Harbor, N.Y., pp. 211–250 (1983); Hoess, R., et al., *Proc. Natl. Acad. Sci.* (U.S.A.) 79:3398–3402 (1982); Sauer, B. L., U.S. Pat. No. 4,959,317, herein incorporated by reference)), so as to facilitate the cloning or multiplex sequencing of the target (PCT Patent Appn. WO92/22650).

The LERA embodiment may be used in the same manner as "gap" ERA or "gapless" ERA, and thus may be used both to identify genetic mutations as well as to amplify nucleic acid molecules of partially unknown sequence. Significantly, however, the LERA embodiment is particularly preferred in amplification procedures that entail the eventual cloning of the amplified target molecule.

5. "Twin Ligation" ERA

"Twin Ligation" ERA is an ERA embodiment that is particularly adapted to permit the detection of multiple linked mutations in a target molecule.

The method differs from other ERA methods in that it employs an additional Blocker Oligonucleotide. This second Blocker Oligonucleotide is located and oriented such that it can block the extension of the End-Run Oligonucleotide at a particular site. Just as the ligation of the Primer Oligonucleotide and Blocker Oligonucleotide are necessary for amplification in ERA, so the ligation of the 5' terminus of the second Blocker Oligonucleotide to the 3' terminus of the End-Run extension product is additionally required in "Twin Ligation" ERA.

Since ligation reactions must occur on each strand in order to produce an amplification product, the method can be used to identify the nucleotides present at two positions in the target sequence. Thus, amplification is dependent on the capacity of the 5' terminal nucleotide of each Blocker Oligonucleotide to hybridize to the target.

In this embodiment, it is especially preferred to design the Blocker Oligonucleotide of the End-Run Oligonucleotide such that it is capable of hybridizing to a sequence within or near the Primer Oligonucleotide hybridization site.

The presence of blunt, double-stranded oligonucleotides may increase the level of spurious blunt end ligation. Thus, in practicing this embodiment, the use of blocking groups and overhangs is desirable.

As will be appreciated, the embodiment may be structured such that for either or both strands the Primer Oligonucleotide or End-Run Oligonucleotide and their respective blockers abut, or hybridize to the target to create a "gap." Similarly, either or both sets of primers and blockers may be tethered to one another, to form a "Loop" ERA reaction. In a like manner, the "twin ligation" embodiment can be combined with any other embodiment of ERA.

6. "Inverse" ERA

Most nucleic acid amplification methods mediate the amplification of a gene sequence only if flanking sequence information has been determined. In many instances, the requirement for sequence information on two regions of a target molecule poses an insurmountable impediment to amplification. "Inverse" ERA is a variation of ERA that can be used with double-stranded DNA in such circumstances to accomplish the exponential amplification of the target sequence. "Inverse" ERA is thus analogous to "inverse" PCR (U.S. Pat. No. 4,994,370).

In practicing "inverse" ERA, prior sequence information is thus available for only one region of the target molecule. Preferably, the available sequence information is reviewed to determine the identity of at least one restriction endonuclease that is incapable of cleaving within the sequenced region of the target. Once such a suitable enzyme has been identified, it is employed to cleave the target molecule. All of the fragments thereby generated will contain termini which are either blunt or cohesive. Significantly, the termini of each fragment can be ligated together to form covalently closed double-stranded circular molecules. Such ligation is the next step in the "inverse" ERA protocol. Most preferably, the resulting covalently closed double-stranded circular molecules will be nicked, such that strand displacement is facilitated. Most preferably, such strand displacement is effected, such that single-stranded closed covalent molecules are obtained.

The sequenced region of the target is used to define the sequence of the Primer, Blocker and End-Run Oligonucleotides. In "inverse" ERA, the Blocker Oligonucleotide hybridizes to a site located 5' to the Primer Oligonucleotide hybridizing site. Thus, with reference to the preceding embodiments, respective positions of the Blocker and Primer Oligonucleotides are reversed.

In "inverse" ERA, the Primer and Blocker Oligonucleotides are designed such that the 3' terminus of the hybridized Blocker Oligonucleotide abuts the 5' terminus of the Primer Oligonucleotide. In such an orientation, the polymerase-mediated, template-dependent extension of the Primer Oligonucleotide results in an extension product that "encircles" the circular target molecule.

The End-Run Oligonucleotide is designed such that it is capable of hybridizing to the Blocker Oligonucleotide. Hence, as in the ERA reactions, exponential amplification of the target is attained.

"Inverse" ERA thus has the capacity to amplify molecules in which only one region has been sequenced. Significantly, by locating the 5' terminal base of the Blocker Oligonucleotide at a polymorphic site, it is possible to use "inverse" ERA to determine whether an individual has a "normal" or "mutant" allele of a particular gene. Thus, "inverse" ERA may be used in the same manner as "gapless" ERA to diagnose genetic disease.

7. "Blind" ERA

"Blind" ERA is a variation of "gap" ERA, and is particularly suited for research and medical applications. "Blind" ERA uses the sequence of the Primer and Blocker Oligonucleotides to assay for the presence of a "hypothetical" target sequence in a sample. It is conducted in the same manner as "gap" ERA, except that, whereas in other ERA embodiments, one uses the target molecule to define the sequences of the Primer, Blocker and End-Run Oligonucleotides, in "blind" ERA, the reactants are used to define the "desired" target molecule. As will be appreciated, the method can be used to selectively amplify target molecules that possess any set of characteristics.

Thus, for example, where the Primer Oligonucleotide is capable of binding to a desired DNA binding site (such as a hormonal receptor binding site, a promoter site, etc.) and the Blocker Oligonucleotide is selected such that it is capable of binding to a restriction endonuclease recognition site, or combination of such sites, the method is capable of amplifying all sequences that satisfy the criteria of possessing a binding site and a restriction site.

8. "Solid Phase" ERA

The ERA reactions discussed above may be conducted in solution. Alternatively, however, the reaction may be conducted in a solid phase using a target molecule that has been immobilized to a solid support. Alternatively, the 5' terminus of the Primer Oligonucleotide, or the 3' terminus of the Blocker Oligonucleotide, may be immobilized.

Methods of immobilizing nucleic acids are discussed, for example by Ruth, J. L. (U.S. Pat. No. 4,948,882), Gilham et al. (*J. Amer. Chem. Soc.*, 86:4982 (1964)), Nickerson et al. (*Proc. Natl. Acad. Sci.* (*U.S.A.*) 87:8923–8927 (1990) and Kremsky et al. (*Nucleic Acids Research* 15:3131–3139 (1987)).

The support material to which the target molecule or reactant may be bound may comprise any solid support (such as glass, polystyrene, polypropylene, polyethylene, dextran, nylon, amylases, natural and modified celluloses, polyacrylamides, agaroses, and magnetite. The nature of the support can be either soluble or insoluble for the purposes of the present invention. The support material may have virtually any possible structural configuration. Thus, the support configuration may be spherical, as in a bead, or cylindrical, as in the inside surface of a test tube, or the external surface of a rod. Alternatively, the surface may be flat such as a sheet, test strip, etc.

9. "ERA Sequencing"

The ERA reactions are particularly suited for use in determining the sequence of target molecules. In particular, the invention facilitates the use of both the "Dideoxy-Mediated Chain Termination Method," also known as the "Sanger Method" of DNA sequencing (Sanger, F., et al., *J. Mol. Biol.* 94:441 (1975)) as well as the "Maxam-Gilbert Chemical Degradation Method" (Maxam, A. M., et al., *Proc. Natl. Acad. Sci.* (*U.S.A.*) 74:560 (1977)), both herein incorporated by reference).

A. Application to Dideoxy Sequencing

In the dideoxy-mediated or "Sanger" chain termination method of DNA sequencing, the sequence of a DNA molecule is obtained through the extension of an oligonucleotide primer which is hybridized to the nucleic acid molecule being sequenced (i.e. the "target"). In the simplest embodiments, four separate primer extension reactions are conducted. Each reaction is conducted in the presence of a DNA polymerase, dNTPs, and a 2',3' dideoxy derivative of the A, T, C, or G nucleotide triphosphate. The incorporation of a dideoxynucleotide results in the termination of the extension reaction. Since the dideoxy derivatives are present in lower concentrations than their corresponding, conventional nucleotide triphosphate analogs, the net result of each of the four reactions is to produce a set of nested oligonucleotides each of which is terminated by the particular dideoxy derivative used in the reaction. By subjecting the reaction products of each of the extension reactions to electrophoresis, it is possible to obtain a 5 series of four "ladders," which can be readily translated into the sequence of the extended primer.

Recently, improved methods of dideoxy sequencing have been developed that greatly enhance the rate of data recovery. In particular, through the use of differently labelled dideoxynucleotides, the need to perform the above-described separate sequencing reactions has been obviated. By using fluorescent labelled dideoxynucleotide derivatives, it is possible to fully automate the process of deducing the target's nucleotide sequencing. Such advances in sequencing technology are described, for example, by Prober, J. M. et al., *Science* 238:336–340 (1987), herein incorporated by reference).

The present invention facilitates dideoxy sequencing methods by simplifying the procedures that must be followed in order to separate the strands of the amplification products. In one embodiment, this is accomplished by denaturing the double-stranded amplification product and by then contacting the mixture of single-stranded molecules with an immobilized probe that is capable of specifically binding to one of the strands.

A substantial improvement in dideoxy DNA sequencing technology was recently developed, and designated "multiplex DNA sequencing" (Church, G. M., et al., *Science* 240:185–188 (1988); Church, G. M. et al., U.S. Pat. No. 4,942,124; both herein incorporated by reference). Multiplex DNA sequencing utilizes DNA libraries which are individually constructed in different vectors, such that the sequence to be determined is flanked by two different, predefined oligonucleotide "tags."

The pool of reaction products are then applied to a sequencing gel, and the oligonucleotides in the DNA sample are separated using gel electrophoresis. The DNA patterns, thus obtained, are then electro-transferred from the gels onto nylon membranes and crosslinked to the membranes using UV light.

Since each lane of the gel contains the reaction products of the sequencing of many different DNA molecules, each lane contains multiple overlaid ladders of sequence information. Each individual ladder may, however be separately visualized by hybridizing a labelled probe for a particular tag to the DNA bound to the membrane. Thus, by repeatedly probing the membrane with different probes, the sequence of each target molecule can be ascertained.

The present invention can be used to facilitate the application of multiplex sequencing. In this regard, the Primer and Blocker Oligonucleotides (or their complements) can function as "tags" to permit multiplex analysis methods to be used.

B. Application to Maxam-Gilbert Sequencing

The Maxam-Gilbert method of DNA sequencing is a degradative method. In this procedure, a fragment of DNA is labeled at one end and partially cleaved in four separate chemical reactions, each of which is specific for cleaving the DNA molecule at a particular base (G or C) at a particular type of base (A/G, C/T, or A>C). As in the above-described dideoxy method, the effect of such reactions is to create a set of nested molecules whose lengths are determined by the locations of a particular base along the length of the DNA molecule being sequenced. The nested reaction products are then resolved by electrophoresis, and the sequence is deduced.

10. Use of "ERA" in Amplifiable Detection Systems

ERA reactions described herein are well suited for use in amplifiable detection systems for detecting virtually anything to which DNA or RNA can be chemically or physically attached. ERA can be utilized to determine the presence or the absence of the DNA or RNA. In one embodiment, ERA is utilized in techniques involving the detection of antigens in diagnostic and forensic applications. In this embodiment of the present invention, a bi-specific linker molecule is used to link a target DNA molecule to an antigen-antibody complex. Thus, where the target molecule has been adapted to contain biotinylated nucleotides, the DNA binding portion of the linker can comprise, for example, avidin, streptavidin, or a biotin binding protein. The antigen-antibody binding portion of the linker can comprise an antibody (reactive with either the antigen or the antibody of the complex), or a binding protein. Such antibodies can be polyclonal, monoclonal, or synthetic (i.e. resulting from recombinant or synthetic methods). Antibody fragments (such as Fab or F(ab)$^2$ fragments, etc.) can alternatively be used.

In this embodiment, the invention facilitates the detection of the antigen-antibody complex. This is accomplished by incubating the antigen-antibody complex in the presence of the target DNA and linker molecule. Preferably, one of these molecular species will be immobilized to a solid support, such as a microtiter plate, dip stick, membrane, paper, etc., such that the separation of unbound target DNA from bound target DNA will be facilitated.

The methods of the present invention are then employed to amplify any target molecule that has become linked to or associated with the antigen-antibody complex. The detection of any amplified target molecule is thus indicative of the presence of the antigen-antibody complex. The use of PCR to detect antigen-antibody complexes has been reported by Sano et al. (*Science* 258:120–122 (1992), herein incorporated by reference.)

The present invention includes articles of manufacture, such as "kits." Such kits will, typically, be specially adapted to contain reagents (including oligonucleotides), enzymes, buffers, etc., for amplification of at least one target sequence comprising at least one region having a defined nucleic acid sequence. A preferred kit comprises at least one container that contains at least one Blocker Oligonucleotide; at least one Primer Oligonucleotide; and least one End-Run Oligonucleotide. These molecules will comprise one or more sets of Blocker, Primer and End-Run Oligonucleotides, where the Blocker Oligonucleotide of a set of oligonucleotides is capable of hybridizing to a portion (i.e. a region or oligonucleotide subset) of a target nucleic acid sequence, the Primer Oligonucleotide of that set is capable of hybridizing to a different portion of the same target nucleic acid sequence, and the End-Run Oligonucleotide of that set comprises a sequence which is complementary to at least a portion of the set's Blocker Oligonucleotide.

In one embodiment, the kit will include separate containers for each or some of its reagents, enzymes, or buffers. Preferably, some or all of the Oligonucleotides of the kit will be mixed together. Indeed, all of the Blocker, Primer and End-Run Oligonucleotides may be present within a single container.

An especially preferred kit comprising reagents for amplification of at least one target sequence comprising at least one region having a defined nucleic acid sequence, would be a kit comprising at least one container, the container comprising at least one Blocker moiety; at least one Primer moiety; and least one End-Run moiety, where the Blocker moiety is capable of hybridizing to a portion of the nucleic acid sequence, the Primer moiety is capable of hybridizing to a different portion of the nucleic acid sequence, and the End-Run moiety comprises a sequence which is complementary to at least a portion of the Blocker moiety.

The buffers that may optionally be included in the kit may be specialized, so as to optimize a particular reaction (such as ligation or polymerization) at the expense of other reactions. Alternatively, the buffers may be designed to as to optimize a set of enzymatic reactions (such as ligation and polymerization). Such buffers may be in concentrated form, such that upon dilution, a desired buffering capacity is obtained. In a preferred kit, the containers that contain the Oligonucleotides also contain buffers. In an alternative embodiment, the containers may contain such Oligonucleotides in a lyophilized form that can be reconstituted with water or a suitable buffer. In a sub-embodiment, such containers may also contain salts or lyophilized buffers, such that upon reconstitution with water, a buffered solution is obtained.

The kit may additionally contain polymerase and/or ligase enzymes, instructional brochures, and the like.

In another embodiment of the present invention, kits are provided which include at least one suitable buffer and optionally additives for optimizing the extending, hybridizing, and ligating reactions of the present invention. Such kits provide all or portions of suitable buffers, enzymes, and additives for one skilled in the art to practice ERA methods described herein and are particularly suitable for those skilled in the art who synthesize or otherwise obtain Blocker, Primer and End-Run Oligonucleotides. Buffer kits can include a single suitable buffer such as tris hydroxymethyl amino methane hydrochloric acid in concentrated, lyophilized, or diluted form. Optionally kits can include buffer and additives such as enzymes, potassium chloride, magnesium chloride, nicotinamide adenine dinucleotide, bovine serum albumin and non-ionic detergent.

Having now generally described the invention, the same will be more readily understood through reference to the following examples which are provided by way of illustration, and are not intended to be limiting of the present invention, unless specified.

EXAMPLE I

To illustrate the ERA, a "target" molecule, and Primer, Blocker and End-Run Oligonucleotides were prepared. A schematic alignment of the Blocker, Primer and End-Run Oligonucleotide moieties, vis-a-vis the Target, is presented in FIG. 10.

The synthesis of oligonucleotide moieties (Blocker, Primer, End-Run) and the single stranded target were performed on a Pharmacia LKB (Upsalla, Sweden) Gene Assembler® plus DNA synthesizer using Beckman Instruments, Inc. (Fullerton, Calif.) phosphoramidites (Product Nos. A:338231; C:338232; G:338233; T:338234). Manufacturer instructions were followed for synthesis, deprotection and cleavage. dNTPs were obtained from a GeneAmp® PCR Reagent Kit (Perkin Elmer, Cat. No. N801-0055). As in all of the following procedures, all chemicals were at least of ACS grade.

The sequences generated were as follows:

Target (SEQ ID NO:1)
    G C C C T T C C C A A C A G T T G C G C A G C C T-
    G A A T G G C G A A T G G C G C T T T G C C T G G Blocker (SEQ ID NO:2)
    CCATTCAGGCTGCGCAACTGTTGddG The 3' terminus of the Blocker Oligonucleotide was blocked by addition of ddGTP; thus the Blocker Oligonucleotide was a 24-mer during the ERA reaction.

Primer (SEQ ID NO:3)
GCGCCATTCG

End-Run (SEQ ID NO:4)
    GTTGCGCAGCCTGAATGG

The Primer and End-Run Oligonucleotides were labelled using T4 polynucleotide kinase and $\gamma^{32}P$ ATP (Amersham) following the protocol described in Sambrook, J. et al. (In: *Molecular Cloning: A Laboratory Manual,* Cold Spring Harbor Laboratory Press, Cold Spring Harbor, N.Y. (1989)). The reaction condition was modified whereby the labelling reaction was conducted at 37° C. for 1 hr., followed by the addition of 0.5 M "cold" ATP (i.e. non-radioactive) to ensure that all kinased ends that did not incorporate radioactive $PO_4$ incorporated the cold $PO_4$. The Blocker Oligonucleotide comprised a "cold" 5'-$PO_4$ terminus.

The various components were initially admixed in a reaction vessel on ice (4° C.) in order to prevent hybridization and enzymatic activity.

Initially, 5 μl of the 10x reaction buffer was added to a 500 μl vessel, followed by 1 μl target sequence (this provided a 50 nM final concentration in 20 μl total solution). Thereafter, each of the four dNTPs were added to achieve a final concentration of 200 μM for each of DATP, dTTP, dCTP, and dGTP in 20 μl total solution. To this admixture was added the labelled oligonucleotide moieties such that a final concentration of 200 nM Blocker Oligonucleotide, 200 nM Primer Oligonucleotide and 150 nM End-Run Oligonucleotide in 20 μl total solution was achieved. This was followed by the addition of 1 unit of AMPLIGASE™ thermostable DNA ligase (Epicentre Technologies, Madison, Wis. CAT. NO. A00101, 5000 units; as defined "one unit catalyzes ligation of 50% of the cos sites in one microgram of bacteriophage lambda DNA in 1 minute at 45° C. in standard 50 μl reaction." The enzyme has a stated half-life of 48 hrs. at 65° C., and 1 hr. at 95° C.), followed by the addition of 1 unit of AmpliTaq® DNA polymerase (Perkin Elmer, Norwalk, Conn., Cat. No. N801-0060). Sufficient double deionized water was then added to achieve a final volume of 20 μl. Concentrations of compounds in a 10x reaction buffer concentrate in a final volume of 1.0 ml (adjusted with double distilled water) were as follows: 100 mM tris hydroxymethyl aminomethane hydrochloric acid ("Tris-HCL"), pH 7.8; 500 mM potassium chloride; 150 mM magnesium chloride; 25 mM $NAD^+$; and 0.01% (w/v) gelatin (Sigma, St. Louis, Mo., Cat. No. G2500).

After the components were admixed, the reaction vessel was heated to 95° C. for 5 min. on a Perkin Elmer Thermal Cycler 480™ as per Manufacturer instructions. This was followed by 20 cycles, each cycle having the following parameters: 95° C.—1 min.; 75° C.—4 min.; 45° C.—4 min. After 20 cycles, 3 μl urea "stop" dye (50% urea, 1% xylene cyanol, 1% bromophenol blue, 0.2x TBE) was added to separate 10 μl aliquots obtained from each reaction vessel, and the reaction vessels were then maintained at 4° C. until analysis.

The reaction vessels were boiled for 10 min. followed by loading onto an electrophoresis slab gel (15% acrylamide gel, 19:1 acrylamide:bis-acrylamide in 7 M urea and 1xTBE). Electrophoresis was conducted using 250 volts (50 mA) for 2 hrs. Thereafter, the electrophoresed aliquots were exposed to Kodak X-OMAT™ AR x-ray film (Eastman Kodak, Rochester, N.Y. Cat. No. 165–1512) for 90 min.

Figure 11:
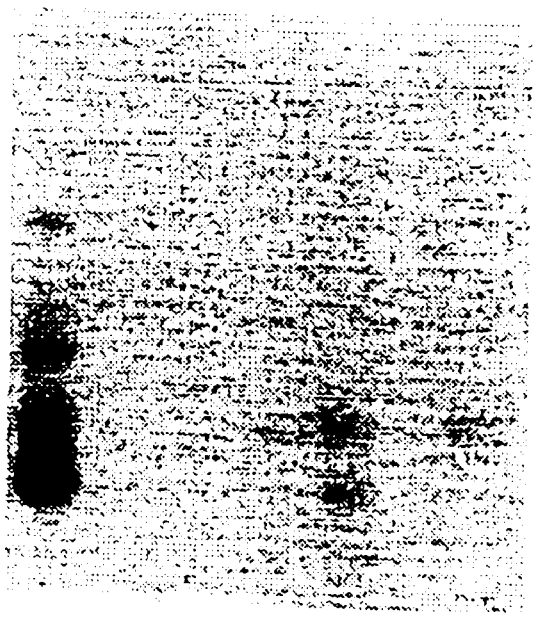
FIG. 11 provides a schematic reproduction of the results of the electrophoresis of amplification reactions conducted as described in Example I. Lane 1 shows the results of the ERA reaction in the presence of Primer Oligonucleotide (Pr), End-Run Oligonucleotide (ER), polymerase (P) and ligase (L), but in the absence of Blocker Oligonucleotide (B). Lane 2 shows the results of the ERA reaction in the presence of Blocker and Primer Oligonucleotides, polymerase and ligase, but in the absence of End-Run Oligonucleotide. Lane 3 shows the results of the ERA reaction when Blocker, Primer, End-Run Oligonucleotides, polymerase and ligase are all present. Lane 4 shows the results of the ERA reaction in the presence of Blocker, Primer, End-Run Oligonucleotides, and polymerase, but in the absence of ligase. Lane 5 shows the results of the ERA reaction in the presence of the Blocker, Primer, and End-Run Oligonucleotides, and ligase, but in the absence of polymerase.

FIG. 11 provides a photographic reproduction of the results of the electrophoresis of aliquots obtained from the above experiment. As is evident from the exposed dark bands of lane 3, of FIG. 11, the ERA protocol resulted in the amplification of the target sequence, and thus was found to provide a unique and viable approach to amplification of a target sequence. Significantly, two bands are found in lane 3, one resulting from amplification of a so-called "extension product" and one from amplification of a so-called "ligation product". Such bands are discernible from one another because the End-Run Oligonucleotide is "shorter" than the Blocker Oligonucleotide, and thus the End-Run extension product will result in amplified products which are "shorter" than amplified products resulting from the ligation of the Blocker and Primer Oligonucleotides.

To further assess the effectiveness of the ERA protocol, several control experiments were performed in concert with the above ERA reaction.

The first control employed the above-described target, Primer Oligonucleotide and End-Run Oligonucleotide reactants, but was performed in the absence of the Blocker Oligonucleotide. The reaction thus measures the extent to which the ligation of the Blocker Oligonucleotide and the Primer Oligonucleotide extension product influences the amplification protocol.

As a control, the above procedure was performed in the absence of the Blocker Oligonucleotide. Under such conditions, the amplification occurs via PCR rather than ERA. The results of this experiment is shown in lane 1, of FIG. 11. As is characteristic of PCR, the strands of the amplification products are of equal size. The fact that PCR amplification occurred demonstrates that the ERA amplification was mediated by a different method, and not by a spurious interference with PCR.

These results therefore indicate that the amplification mediated by ERA (in the presence of Primer, Blocker and End-Run Oligonucleotides) is not PCR.

As an additional control, the above-described ERA procedure was performed in the absence of ligase. The purpose of this control was to demonstrate that the amplification does not result from PCR that occurs through the displacement of the Blocker Oligonucleotide. Lane 4, of FIG. 11 provides the results of this experiment. The results confirm the expectation that, as expected, in the absence of ligase, the Blocker and Primer Oligonucleotides were unable to covalently bind to one another, and no amplification of the target sequence occurred. This is because without the ligation event (and because of the use of a single-stranded target), no template is amplified that is capable of supporting the extension of the End-Run Oligonucleotide.

As a further control, the ERA protocol was performed in the absence of the End-Run Oligonucleotide. This control investigates whether the End-Run Oligonucleotide is needed in order to obtain the exponential amplification of the target. Lane 2, of FIG. 11 shows that in the absence of the End-Run Oligonucleotide, only a linear amplification of the target sequence is obtained. In particular, only one strand (the Primer Oligonucleotide—Blocker Oligonucleotide strand) is amplified. This control demonstrates that in the absence of the End-Run Oligonucleotide a linear "oligonucleotide ligation assay" is obtained.

Lane 5 of FIG. 11 provides the results of an additional control in which the ERA reaction is conducted in the absence of DNA polymerase. As is evident, only linear amplification occurred.

Lanes 2 and 5 of FIG. 11 further evidence that the ERA protocol does not result in exponential amplification unless all of the moieties are utilized. Lane 2, which provided an OLA control, evidences linear amplification of the target sequence (based upon, e.g., the relative size and density of the autoradiograph band), as would be expected. OLA does not result in exponential amplification, in that only two "primers" and a ligase enzyme are utilized. However, even when the End-Run Oligonucleotide is added in the absence of polymerase to the reaction vessel (lane 5), the resulting band is essentially identical to that of lane 2.

EXAMPLE II

To further evaluate the capacity of ERA to amplify a target molecule, an additional series of experiments were performed using the target, Primer, Blocker and End-Run Oligonucleotides described in Example I.

In this series of experiments, the target concentration was lowered one thousand fold or one million fold from that used in Example I. In Example I, the target concentration was about $10^{-9}$ M (i.e. $10^{12}$ molecules per sample). In Example II, target concentrations of about $10^{-12}$ M (i.e. $10^9$ molecules per sample) and $10^{-15}$ M ($10^6$ molecules per sample) were employed. These concentrations were selected as being within the range necessary to detect a single gene within a human sample.

For Example II, target, Primer and End-Run Oligonucleotides were synthesized as in Example I. Blocker Oligonucleotide was synthesized using a Biosearch 8750™ oligonucleotide synthesizer (Milligen Biosearch, Sam Rafael, Calif.) to generate a Blocker Oligonucleotide as defined in Example I, but containing a biotin molecule at its 3'-end. A 3'-Biotin-ON CPG column (Clonetech Labs, Inc., Palo Alto, Calif. Cat. No. 5225-1) was used for Blocker Oligonucleotide synthesis.

ERA was conducted as in Example I, however, the polymerase enzyme was Amplitaq® DNA polymerase, Stoffel Fragment (exonuclease deficient version) (Perkin Elmer Cat. No. N808-0038). Concentrations of the components in a 10 x reaction buffer concentrate in a final volume of 1.0 ml (adjusted with double distilled water) were as follows: 200 mM TRIS-HCl, pH 7.8; 200 mM potassium chloride; 25 mM ammonium chloride; 20 mM magnesium chloride; 50 mM dithiothretiol; 500 $\mu$M NAD$^+$; 500$\mu$g/ml bovine serum albumin; and 1% Triton X-100™ (Sigma, Cat. No. T6878).

End-Run and Primer Oligonucleotides were labelled as in Example I, and Blocker Oligonucleotide was labelled as set forth for End-Run and Primer Oligonucleotides in Example I (i.e. a radioactive label was incorporated into the Blocker Oligonucleotide).

The various components were initially admixed in a reaction vessel on ice (4° C.) in order to substantially prevent hybridization and non-specific hybridization.

Initially, 5 $\mu$l of the 10 x reaction buffer was added to a 500 $\mu$l vessel, followed by addition of 1 $\mu$l of a 1.0 nM stock solution of target sequence (final target sequence concentration in 50 $\mu$l total solution: 20 picomolar) or 1 $\mu$l of a 1.0 pM stock solution of target sequence (final target sequence concentration in 50 $\mu$l total solution: 20 fentomolar. Thereafter, each of the four dNTPs were added to achieve a final concentration of 200 $\mu$M for each of DATP, dTTP, dCTP and dGTP in 50 $\mu$l total solution. To this admixture was added the labelled oligonucleotide moieties such that a final concentration of 120 nM Blocker Oligonucleotide, 40 nM Primer Oligonucleotide and 40 nM End-Run Oligonucleotide (3:1:1 of Blocker:Primer:End-Run) in 50 $\mu$l total solution was achieved. This was followed by the addition of 10 units of the aforementioned ligase enzyme, followed by sufficient double deionized water to achieve a volume of 49 $\mu$l.

After the components were admixed, the reaction vessel was heated to 95° C. for 5 min. on the aforementioned thermal cycler to achieve complete denaturation of target and oligonucleotide moieties. this was followed by the addition of 2 units (1 $\mu$l) of the aforementioned polymerase enzyme to the reaction vessel. This was followed by 40 cycles, each cycle having the following parameters: 95° C.—1 min.; 70° C.—4 min.; 40° C.—4 min.

After 40 cycles, 3 $\mu$l "stop" dye (as described in Example I.L.) was added to separate 10 $\mu$l aliquots obtained from each of the reaction vessels of Sections II.G–I. Thereafter, the aliquots were boiled for 10 min. followed by loading into an electrophoresis slab gel. Electrophoresis was conducted and exposure was obtained as in Example I.

Figure 12:
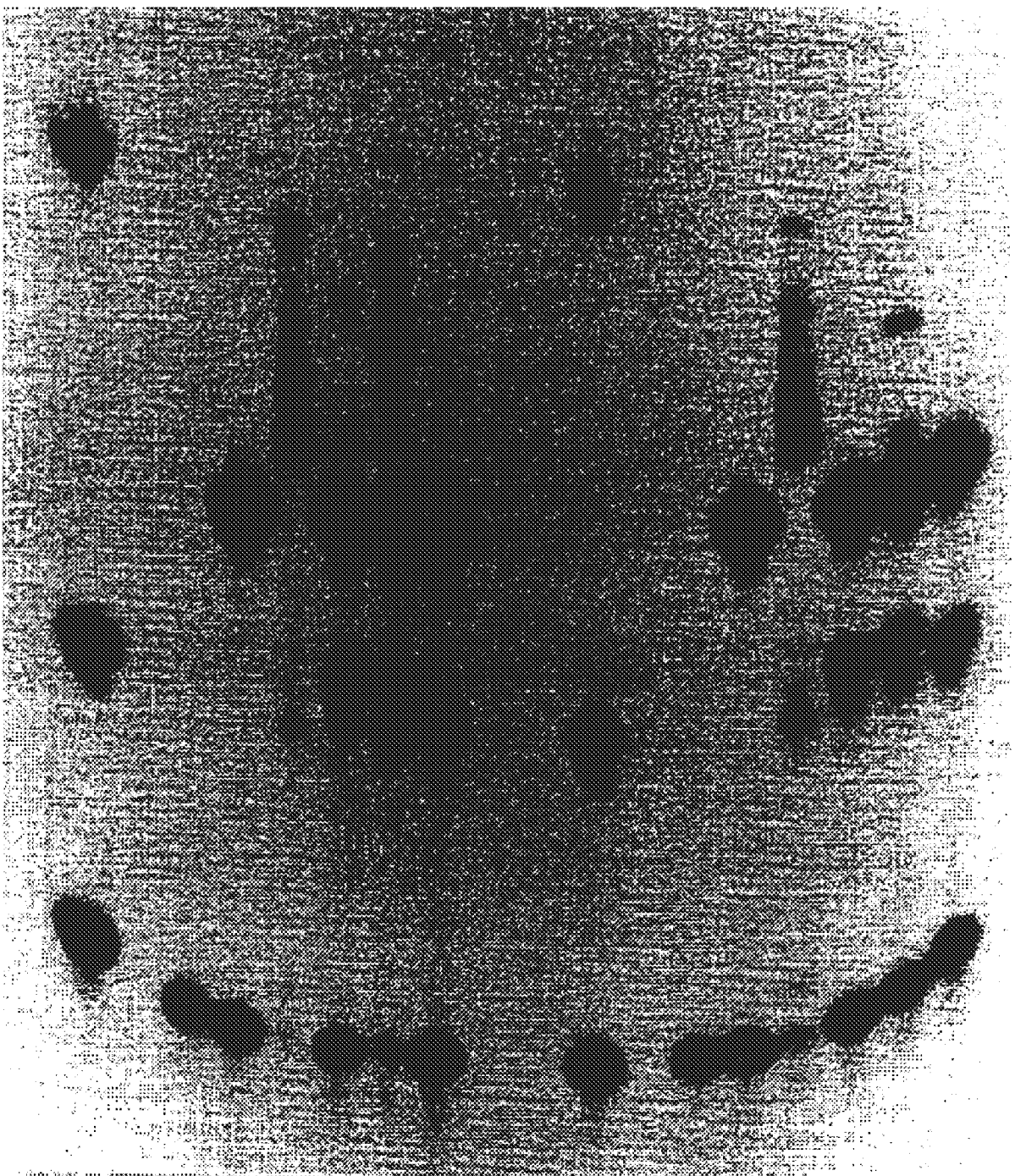
FIG. 12 provides a schematic reproduction of the results of the electrophoresis of amplification reactions conducted as described in Example II using target molecule concentrations of $10^{-12}$ M (FIG. A) or $10^{-15}$ M (FIG. 12B). Lane M illustrates the relative position of the End-Run and Primer Oligonucleotides and the target on the gel. The relative position of the Blocker Oligonucleotide is shown in lane 2. Lane 1 shows the position of primer. Lane 2 shows the results of the ERA reaction in the presence of the Blocker and Primer Oligonucleotides, polymerase and ligase, but in the absence of End-Run Oligonucleotide. Lane 3 shows the results of the ERA reaction in the presence of the Primer and End-Run Oligonucleotide, polymerase and ligase, but in the absence of Blocker Oligonucleotide. Lane 4 shows the results of the ERA reaction in the presence of Blocker, Primer and End-Run Oligonucleotides, and polymerase, but in the absence of ligase. Lane 5 shows the results of the ERA reaction when Blocker, Primer and End-Run Oligonucleotides, polymerase and ligase, are all present. Lane 6 shows the results of the ERA reaction in the presence of Blocker, Primer, End-Run Oligonucleotides, and ligase, but in the absence of polymerase.
Figure 13:
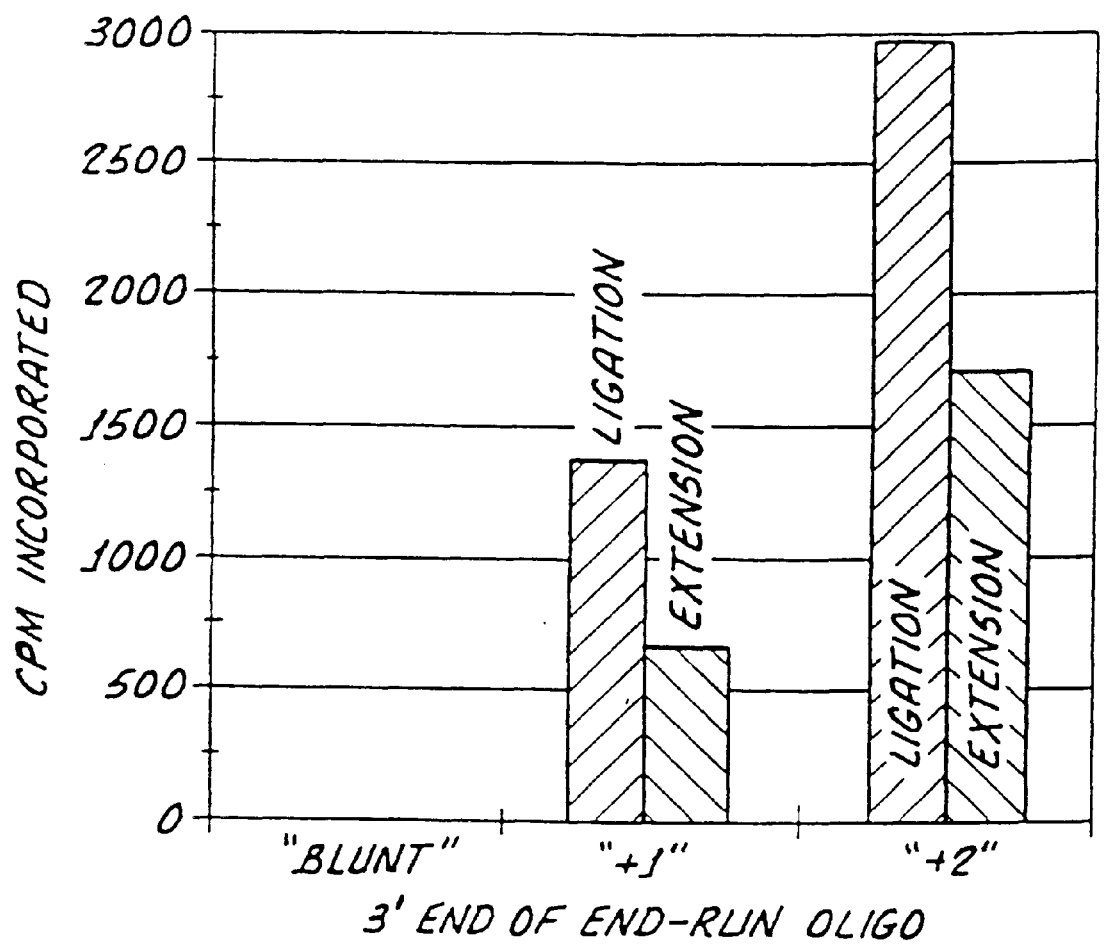
Figure 14:
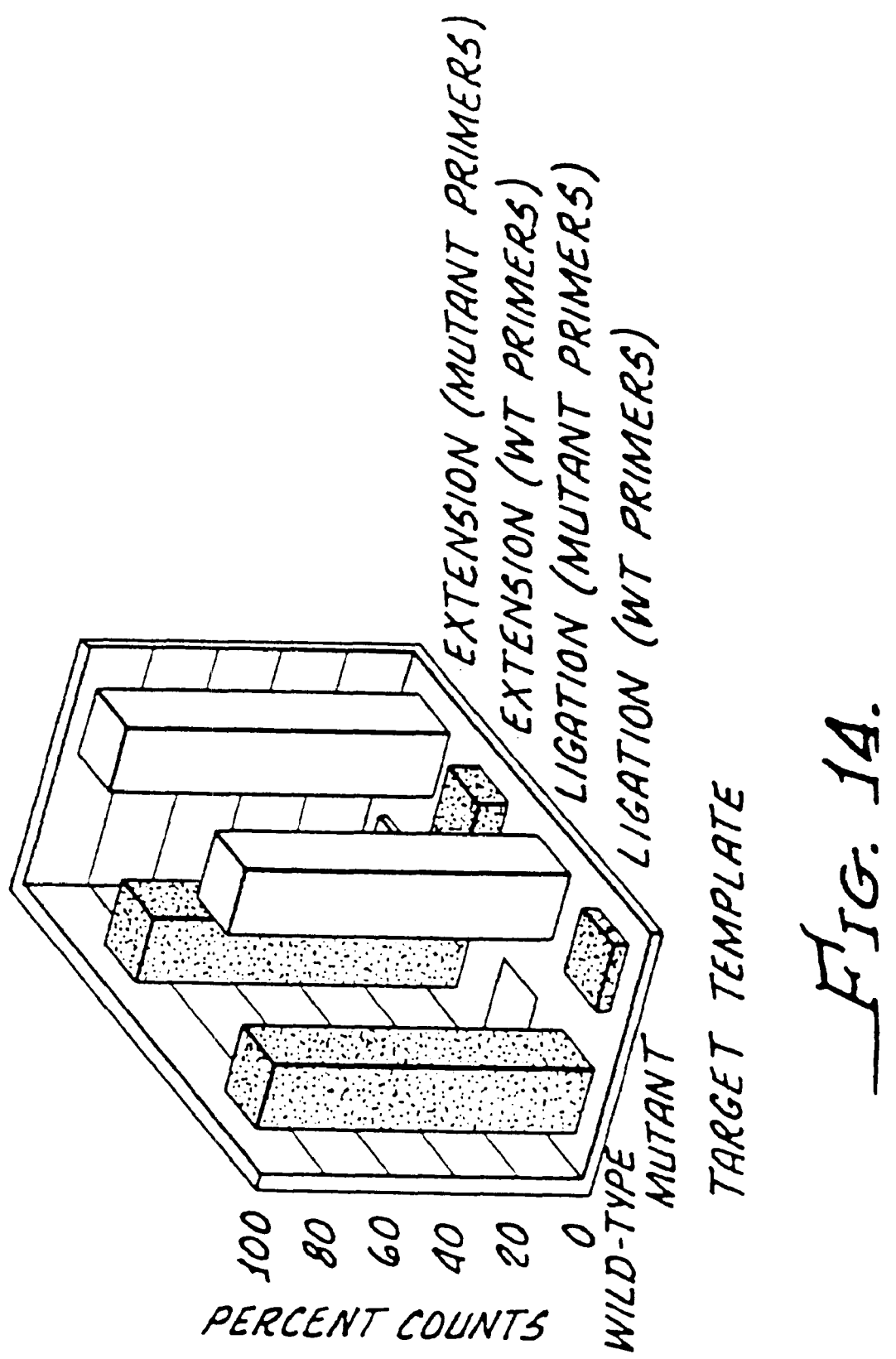
Figure 15:
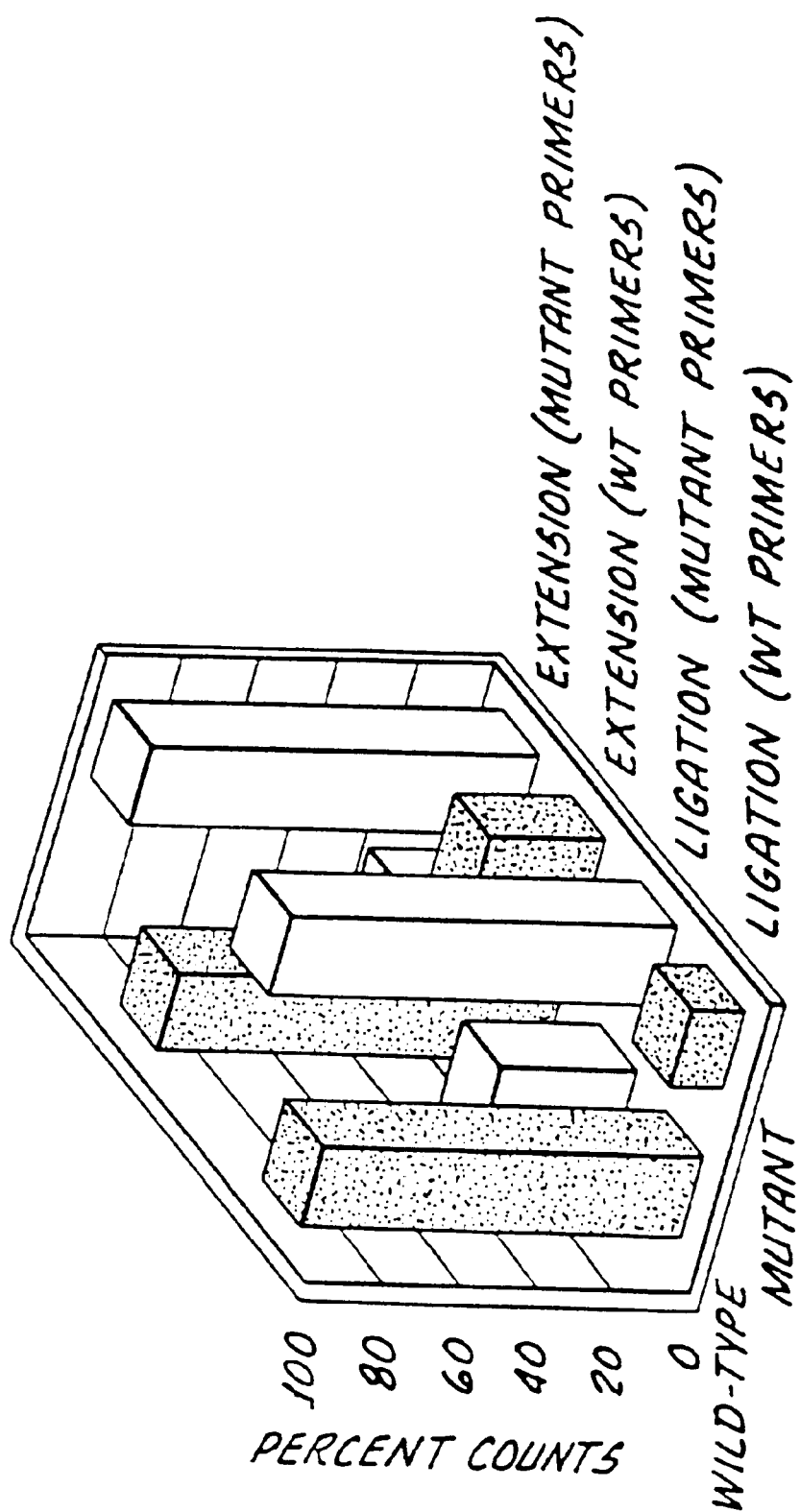
Figure 16:
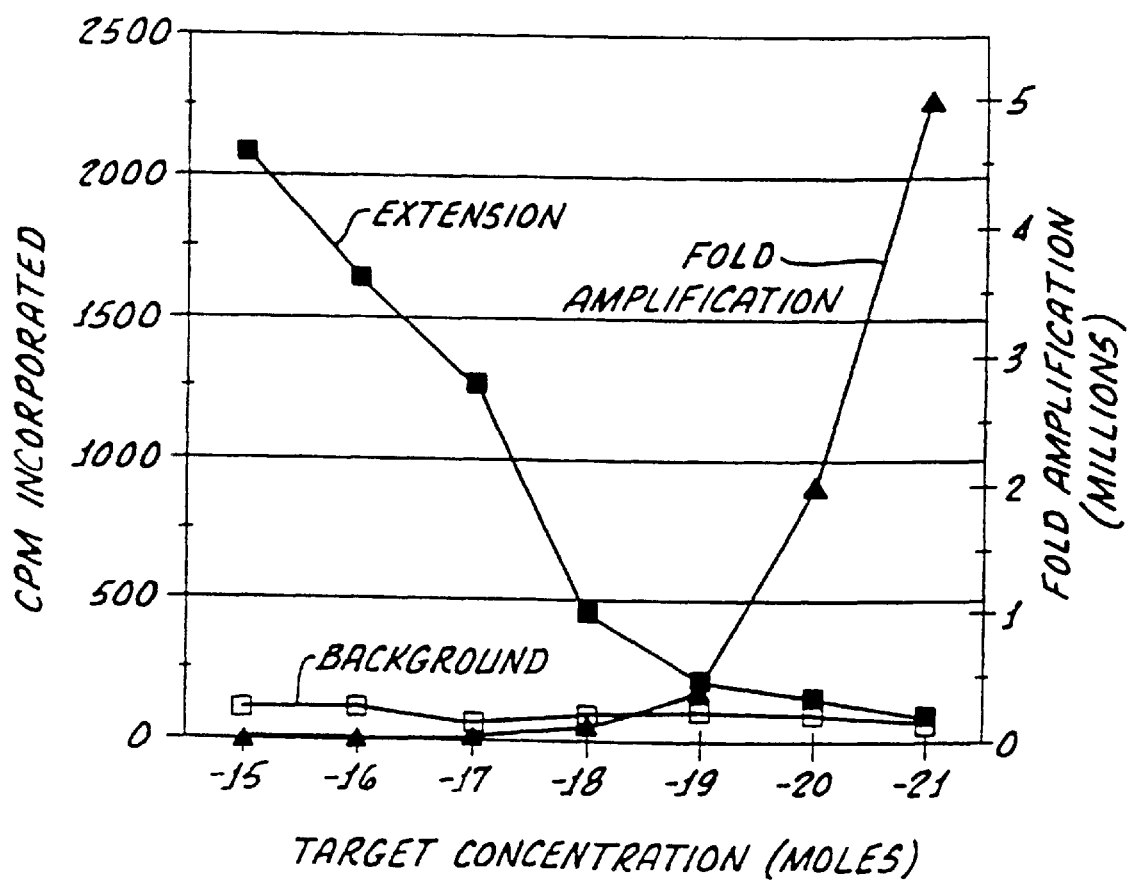
Figure 17:
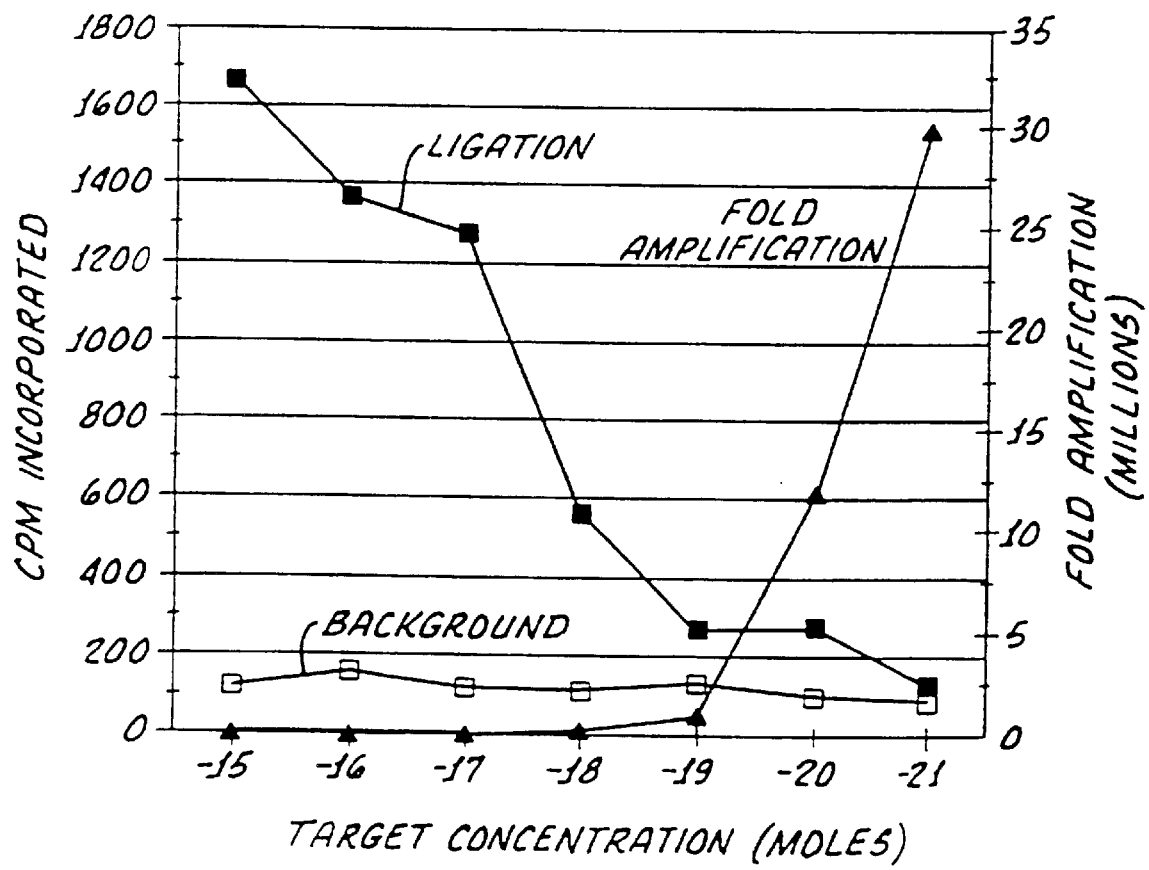

FIG. 12A and FIG. 12B demonstrate the capacity of ERA to detect a target molecule even when present at a concentration of $10^{-12}$ M or $10^{-15}$ M, respectively. Lane 5 of FIGS. 12A and 12B demonstrate that End-Run Amplification of the target sequence was obtained. Most importantly, FIG. 12B evidences that detection and amplification of a target sequence present at a concentration similar to that for a gene of interest can be accomplished using the disclosed ERA protocol.

Various controls were performed in order to ensure that the observed amplification was due to the ERA reactions. In particular, the reactions were performed in the absence of ligase, to determine if a PCR amplification had occurred.

Lane 4 of FIGS. 12A and 12B demonstrate the results of the "ligase-free" ERA control reactions, and show that in the absence of ligation the Blocker and Primer Oligonucleotides were unable to covalently bind to one another, and no amplification of the target sequence occurred.

As with Example I, amplification of the target sequence using a PCR protocol is evident from the results of lane 3 of FIGS. 12A and B; again, because all of the conditions were substantially identical for each protocol, the results of lane 3 indicate that the parameters utilized did not interfere with PCR amplification of the target sequence.

Also consistent with the results shown in Example I, only linear amplification (of one strand) was observed in the absence of polymerase (lane 6, FIGS. 12A and 12B).

Lane M provides the exposure resulting from End-Run Oligonucleotide, Primer Oligonucleotides, and target. Lane 1 shows the position of Primer Oligonucleotide. The position of Blocker Oligonucleotide is shown in lane 2.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method of amplifying the concentration of a target nucleic acid molecule, said method comprising the steps of:
   (A) hybridizing a Blocker Oligonucleotide to said target nucleic acid molecule to thereby form a double-stranded nucleic acid molecule;
   (B) hybridizing a Primer Oligonucleotide to said target nucleic acid molecule of said double-stranded nucleic acid molecule such that the 3' terminus of said Primer Oligonucleotide abuts, or can be extended in a polymerase-mediated, template-dependent primer extension reaction to abut, the 5' terminus of said hybridized Blocker Oligonucleotide;
   (C) (1) where said 3' terminus of said hybridized Primer Oligonucleotide abuts said 5' terminus of said hybridized Blocker Oligonucleotide, conducting step (D); or
   (2) where said 3' terminus of said hybridized Primer Oligonucleotide does not abut said 5' terminus of said hybridized Blocker Oligonucleotide, causing said 3' terminus of said hybridized Primer Oligonucleotide to be extended in a polymerase-mediated, template-dependent primer extension reaction, to thereby form a Primer extension product whose 3' terminus abuts said 5' terminus of said hybridized Blocker Oligonucleotide; then conducting step (D);
   (D) ligating said abutting 3' terminus of said hybridized Primer Oligonucleotide of step (C)(1) or said abutting 3' terminus of said hybridized Primer extension product of step (C)(2) to said 5' terminus of said hybridized Blocker Oligonucleotide to thereby form a ligation product having the sequence of said Primer Oligonucleotide or said Primer extension product, and the sequence of said Blocker Oligonucleotide;
   (E) separating said ligation product from said nucleic acid molecule;
   (F) hybridizing an End-Run Oligonucleotide to said sequence of said Blocker Oligonucleotide of said ligation product; and
   (G) extending the 3' terminus of said hybridized End-Run Oligonucleotide in a polymerase-mediated, template-dependent primer extension reaction to thereby form an End-Run extension product whose sequence comprises the target sequence and thereby amplify the concentration of said target molecule; wherein said step (A), said group of steps (B), (C) and (D), and said group of steps (E) (F) and (G), can be conducted in any order with respect to one another;

wherein said Blocker Oligonucleotide is present whenever polymerase-mediated, template-dependent extension of said Primer Oligonucleotide can occur.

2. The method of claim 1, wherein said steps are conducted in sequence.

3. The method of claim 1, wherein said group of steps (B), (C) and (D), are conducted before said group of steps (E) and (F).

4. The method of claim 1, wherein said group of steps (E) and (F) are conducted before said group of steps (B), (C) and (D).

5. The method of claim 1, wherein said target nucleic acid molecule is a single-stranded DNA or RNA molecule.

6. The method of claim 1, wherein said target nucleic acid molecule is a double-stranded RNA molecule, and wherein a first strand of said double-stranded molecule is amplified by the formation of said ligation product of step (D), and a second strand is amplified by the formation of said End-Run extension product of step (G).

7. The method of claim 1, wherein the 3' terminus of said Blocker Oligonucleotide and the 5' terminus of said Primer Oligonucleotide are tethered together.

8. The method of claim 1, wherein in step (B) said Primer Oligonucleotide has a 3' terminus, which when hybridized to said target nucleic acid molecule of said double-stranded nucleic acid molecule abuts the 5' terminus of said hybridized Blocker Oligonucleotide.

9. The method of claim 1, wherein in step (B) said Primer Oligonucleotide has a 3' terminus, which when hybridized to said target nucleic acid molecule of said double-stranded nucleic acid molecule can be extended in a polymerase-mediated, template-dependent primer extension reaction to abut the 5' terminus of said Blocker Oligonucleotide.

10. The method of claim 1, wherein said method additionally includes the steps of:
   (H) hybridizing a Blocker Oligonucleotide to said End-Run extension product to thereby form a double-stranded nucleic acid molecule;
   (I) hybridizing a Primer Oligonucleotide to said End-Run extension product of said double-stranded nucleic acid molecule of step (H) to thereby form a double-stranded nucleic acid molecule wherein the 3' terminus of said Primer Oligonucleotide abuts, or can be extended in a polymerase-mediated, template-dependent primer extension reaction to abut, the 5' terminus of said hybridized Blocker Oligonucleotide;
   (J) 1. where said 3' terminus of the hybridized Primer Oligonucleotide of step (I) abuts said 5' terminus of said hybridized Blocker Oligonucleotide, conducting step (K); or
   2. where said 3' terminus of said hybridized Primer Oligonucleotide of step (I) does not abut said 5' terminus of said hybridized Blocker Oligonucleotide, causing said 3' terminus of said hybridized Primer Oligonucleotide to be extended in a polymerase-mediated, template-dependent primer extension reaction, to thereby form a Primer extension product whose 3' terminus abuts said 5' terminus of said hybridized Blocker Oligonucleotide; then conducting step (K);
   (K) ligating said abutting 3' terminus of said hybridized Primer Oligonucleotide of step (J)(1) or said abutting 3' terminus of said hybridized Primer extension product of step (J)(2) to said 5' terminus of said hybridized Blocker Oligonucleotide to thereby form and amplify said ligation product;
   (L) hybridizing an End-Run Oligonucleotide to said sequence of said Blocker Oligonucleotide of said ligation product of step (K); and
   (M) extending the 3' terminus of said hybridized End-Run Oligonucleotide in a polymerase-mediated, template-dependent primer extension reaction to thereby form and amplify an End-Run extension product.

11. The method of claim 10, wherein the sequence of steps (H) through (M) is repeated at least once.

12. The method of claim 9, wherein said method additionally includes the steps of:
(H) hybridizing a second Blocker Oligonucleotide to said End-Run extension product to thereby form a double-stranded nucleic acid molecule, wherein said second Blocker Oligonucleotide hybridizes to said End-Run extension product at a site to which said Blocker of step (A) or said Primer Oligonucleotide of step (B) cannot hybridize;
(I) hybridizing a second Primer Oligonucleotide to said End-Run extension product of said double-stranded nucleic acid molecule such that the 3' terminus of said second Primer Oligonucleotide abuts, or can be extended in a polymerase-mediated, template-dependent primer extension reaction to abut, the 5' terminus of said hybridized second Blocker Oligonucleotide;
(J) (1) where said 3' terminus of said hybridized second Primer Oligonucleotide abuts said 5' terminus of said hybridized second Blocker Oligonucleotide, conducting step (K); or
(2) where said 3' terminus of said hybridized second Primer Oligonucleotide does not abut said 5' terminus of said hybridized second Blocker Oligonucleotide, causing said 3' terminus of said hybridized second Primer Oligonucleotide to be extended in a polymerase-mediated, template-dependent primer extension reaction, to thereby form a second Primer extension product whose 3' terminus abuts said 5' terminus of said hybridized second Blocker Oligonucleotide; then conducting step (K);
(K) ligating said abutting 3' terminus of said hybridized second Primer Oligonucleotide of step (J)(1) or said abutting 3' terminus of said hybridized second Primer extension product of step (J) (2) to said 5' terminus of said hybridized Blocker Oligonucleotide to thereby form a second ligation product having the sequence of said second Primer Oligonucleotide or said second Primer extension product, and the sequence of said second Blocker Oligonucleotide; (L) hybridizing a second End-Run Oligonucleotide to said sequence of said second Blocker Oligonucleotide of said second ligation product; (M) extending the 3' terminus of said hybridized second End-Run Oligonucleotide in a polymerase-mediated, template-dependent primer extension reaction to form a second End-Run extension product and thereby amplify the concentration of said sequence of said target molecule.

13. The method of claim 9, wherein said method additionally includes the steps of:
(H) hybridizing a second Blocker Oligonucleotide to said ligation product to thereby form a double-stranded nucleic acid molecule, wherein said second Blocker Oligonucleotide hybridizes to said ligation product at a site to which said Blocker of step (A) or said Primer Oligonucleotide of step (B) cannot hybridize;
(I) hybridizing a second Primer Oligonucleotide to said ligation product of said double-stranded nucleic acid molecule such that the 3' terminus of said second Primer Oligonucleotide abuts, or can be extended in a polymerase-mediated, template-dependent primer extension reaction to abut, the 5' terminus of said hybridized second Blocker Oligonucleotide;
(J) (1) where said 3' terminus of said hybridized second Primer Oligonucleotide abuts said 5' terminus of said hybridized second Blocker Oligonucleotide, conducting step (K); or
(2) where said 3' terminus of said hybridized second Primer Oligonucleotide does not abut said 5' terminus of said hybridized second Blocker Oligonucleotide, causing said 3' terminus of said hybridized second Primer Oligonucleotide to be extended in a polymerase-mediated, template-dependent primer extension reaction, to thereby form a second Primer extension product whose 3' terminus abuts said 5' terminus of said hybridized second Blocker Oligonucleotide; then conducting step (K);
(K) ligating said abutting 3' terminus of said hybridized second Primer Oligonucleotide of step (J)(1) or said abutting 3' terminus of said hybridized second Primer extension product of step (J) (2) to said 5' terminus of said hybridized Blocker Oligonucleotide to thereby form a second ligation product having the sequence of said second Primer Oligonucleotide or said second Primer extension product, and the sequence of said second Blocker Oligonucleotide;
(L) hybridizing a second End-Run Oligonucleotide to said sequence of said second Blocker Oligonucleotide of said second ligation product; and
(M) extending the 3' terminus of said hybridized second End-Run Oligonucleotide in a polymerase-mediated, template-dependent primer extension reaction to form a second End-Run extension product and thereby amplify the concentration of said sequence of said target molecule.

14. The method of claim 12, wherein the sequence of steps (H) through (M) is repeated at least once.

15. A method of determining whether a selected nucleotide is present at a predetermined site of a target nucleic acid molecule, said method comprising the steps of:
(A) providing conditions for hybridizing a Blocker Oligonucleotide to said target nucleic acid molecule to thereby form a double-stranded nucleic acid molecule, wherein the 5' terminus of said hybridized Blocker Oligonucleotide is positioned such that its 5' terminal nucleotide opposes said predetermined site of said target molecule, and is complementary to said selected nucleotide;
(B) providing conditions for hybridizing a Primer Oligonucleotide to said target nucleic acid molecule of said double-stranded nucleic acid molecule such that the 3' terminus of said Primer Oligonucleotide abuts, or can be extended in a polymerase-mediated, template-dependent primer extension reaction to abut, the 5' terminus of said hybridized Blocker Oligonucleotide;
(C) (1) where if said 3' terminus of said Primer Oligonucleotide abuts said 5' terminus of said Blocker Oligonucleotide, conducting step (D); or
(2) where said 3' terminus of said Primer Oligonucleotide does not abut said 5' terminus of said Blocker Oligonucleotide, causing said 3' terminus of said hybridized Primer Oligonucleotide to extend in a polymerase-mediated, template-dependent primer extension reaction, to thereby form a Primer extension product whose 3' terminus abuts said 5' terminus of said Blocker Oligonucleotide; then conducting step (D);
(D) incubating said abutting 3' terminus of said hybridized Primer Oligonucleotide of step (C)(1) or said abutting 3' terminus of said hybridized Primer extension product of step (C)(2) and said 5' terminus of said hybridized Blocker Oligonucleotide in the presence of a ligase, under conditions conducive to nucleic acid ligation;

(E) determining whether said selected nucleotide is present at said predetermined site by detecting whether step (D) results in the formation of a ligation product having the sequence of said Primer Oligonucleotide or said Primer extension product and said Blocker Oligonucleotide, wherein the formation of said ligation product is dependent on the capacity of the 5' terminal nucleotide of said Blocker Oligonucleotide to hybridize to the nucleotide at the predetermined site; said detection being accomplished by the sub-steps:

(1) providing an End-Run Oligonucleotide to said incubation, and maintaining said incubation under conditions sufficient to permit nucleic acid hybridization and polymerase-mediated, template-dependent primer extension to occur; and (2) determining whether said End-Run Oligonucleotide is extended to thereby form an End-Run extension product whose sequence comprises the target sequence and contains a sequence complementary to a sequence of said Primer Oligonucleotide;

wherein said Blocker Oligonucleotide is present whenever polymerase-mediated, template-dependent extension of said Primer Oligonucleotide can occur.

16. The method of claim 15, wherein said target nucleic acid molecule is a single-stranded DNA or RNA molecule.

17. The method of claim 15, wherein in step (B) said Primer Oligonucleotide has a 3' terminus, which when hybridized to said target nucleic acid molecule of said double-stranded nucleic acid molecule abuts the 5' terminus of said hybridized Blocker Oligonucleotide.

18. The method of claim 15, wherein in step (B) said Primer Oligonucleotide has a 3' terminus, which when hybridized to said target nucleic acid molecule of said double-stranded nucleic acid molecule can be extended in a polymerase-mediated, template-dependent primer extension reaction to abut the 5' terminus of said Blocker Oligonucleotide.

19. The method of claim 15, wherein in step (E)(2) said determination of whether said End-Run Oligonucleotide is extended to contain a sequence complementary to a sequence of said Primer Oligonucleotide is conducted by amplifying any End-Run extension product using a method comprising the sub-steps of:

(a) hybridizing said Blocker Oligonucleotide to any of said End-Run extension products present in the incubation to thereby form double-stranded nucleic acid molecules;

(b) hybridizing said Primer Oligonucleotide to the End-Run extension product of any of said double-stranded nucleic acid molecules such that the 3' terminus of said Primer Oligonucleotide abuts, or can be extended in a polymerase-mediated, template-dependent primer extension reaction to abut, the 5' terminus of said hybridized Blocker Oligonucleotide;

(c) (1) where said 3' terminus of said hybridized Primer Oligonucleotide abuts said 5' terminus of said hybridized Blocker Oligonucleotide, conducting step (d); or (2) where said 3' terminus of said hybridized Primer Oligonucleotide does not abut said 5' terminus of said hybridized Blocker Oligonucleotide, causing said 3' terminus of said hybridized Primer Oligonucleotide to be extended in a polymerase-mediated, template-dependent primer extension reaction, to thereby form a Primer extension product whose 3' terminus abuts said 5' terminus of said hybridized Blocker Oligonucleotide; then conducting step (d);

(d) ligating said abutting 3' terminus of any of said hybridized Primer Oligonucleotide of step (c)(1) or said abutting 3' terminus of any of said hybridized Primer extension product of step (c)(2) to said 5' terminus of any of said hybridized Blocker Oligonucleotide to thereby form a ligation product having the sequence of said Primer Oligonucleotide or said Primer extension product, and the sequence of said Blocker Oligonucleotide;

(e) separating said ligation product from said End-Run Extension product;

(f) hybridizing said End-Run Oligonucleotide to said sequence of said Blocker Oligonucleotide of any of said ligation product; and (g) extending the 3' terminus of said hybridized End-Run Oligonucleotide in a polymerase-mediated, template-dependent primer extension reaction to form and amplify said End-Run extension product.

20. The method of claim 19, wherein the sequence of sub-steps (a) through (G) is repeated at least once.

21. The method of claim 15, wherein said predetermined site is a polymorphic locus.

22. The method of claim 15, wherein said 5' terminal nucleotide of said Blocker Oligonucleotide is capable of hybridizing to said predetermined site only if said site contains a genetic mutation.

23. The method of claim 15, wherein prior to performing step (A), the concentration of said target nucleic acid is amplified according to a method comprising the steps of:

(A) hybridizing a Blocker Oligonucleotide to said target nucleic acid molecule to thereby form a double-stranded nucleic acid molecule;

(B) hybridizing a Primer Oligonucleotide to said target nucleic acid molecule of said double-stranded nucleic acid molecule such that the 3' terminus of said Primer Oligonucleotide abuts, or can be extended in a polymerase-mediated, template-dependent primer extension reaction to abut, the 5' terminus of said hybridized Blocker Oligonucleotide;

(C) (1) where said 3' terminus of said hybridized Primer Oligonucleotide abuts said 5' terminus of said hybridized Blocker Oligonucleotide, conducting step (D); or (2) where said 3' terminus of said hybridized Primer Oligonucleotide does not abut said 5' terminus of said hybridized Blocker Oligonucleotide, causing said 3' terminus of said hybridized Primer Oligonucleotide to be extended in a polymerase-mediated, template-dependent primer extension reaction, to thereby form a Primer extension product whose 3' terminus abuts said 5' terminus of said hybridized Blocker Oligonucleotide; then conducting step (D);

(D) ligating said abutting 3' terminus of said hybridized Primer Oligonucleotide of step (C)(1) or said abutting 3' terminus of said hybridized Primer extension product of step (C)(2) to said 5' terminus of said hybridized Blocker Oligonucleotide to thereby form a ligation product having the sequence of said Primer Oligonucleotide or said Primer extension product, and the sequence of said Blocker Oligonucleotide;

(E) separating said ligation product from said nucleic acid molecule;

(F) hybridizing an End-Run Oligonucleotide to said sequence of said Blocker Oligonucleotide of said ligation product; and (G) extending the 3' terminus of said hybridized End-Run Oligonucleotide in a polymerase-mediated, template-dependent primer extension reaction to thereby form an End-Run extension product whose sequence comprises the target sequence and thereby amplify the concentration of said target molecule; wherein said step (A), said group of steps (B), (C) and (D), and said group of steps (E), (F) and (G), can be conducted in any order with respect to one another.

24. A method of determining whether a selected nucleotide is present at a predetermined site of a target nucleic acid molecule, said method comprising the steps of:
   (A) providing conditions for hybridizing a Blocker Oligonucleotide to said target nucleic acid molecule to thereby form a double-stranded nucleic acid molecule, wherein the 5' terminus of said hybridized Blocker Oligonucleotide is positioned such its 5' terminal nucleotide is hybridized to the nucleotide located immediately 3' of the predetermined site of said target molecule;
   (B) providing conditions for hybridizing a Primer Oligonucleotide to said target nucleic acid molecule of said partially double-stranded nucleic acid molecule such that the 3' terminus of said Primer Oligonucleotide abuts the 5' terminus of said hybridized Blocker Oligonucleotide; wherein the 3' terminal nucleotide is complementary to said selected nucleotide;
   (C) incubating said abutting 3' terminus of said hybridized Primer Oligonucleotide and said 5' terminus of said hybridized Blocker Oligonucleotide in the presence of a ligase, under conditions conducive to nucleic acid ligation;
   (D) determining whether said selected nucleotide is present at said predetermined site by detecting whether step (C) results in the formation of a ligation product having the sequence of said Primer Oligonucleotide or said Primer extension product and said Blocker Oligonucleotide, wherein the formation of said ligation product is dependent on the capacity of the 3' terminal nucleotide of said Primer Oligonucleotide to hybridize to the nucleotide at the predetermined site; said detection being accomplished by the sub-steps:
      (1) providing an End-Run Oligonucleotide to said incubation, and maintaining said incubation under conditions sufficient to permit nucleic acid hybridization and polymerase-mediated, template-dependent primer extension to occur; and
      (2) determining whether said End-Run Oligonucleotide is extended to thereby form an End-Run extension product whose sequence comprises the target sequence and contains a sequence complementary to a sequence of said Primer Oligonucleotide;
wherein said Blocker Oligonucleotide is present whenever polymerase-mediated, template-dependent extension of said Primer Oligonucleotide can occur.

25. The method of claim 24, wherein said target nucleic acid molecule is a single-stranded DNA or RNA molecule.

26. The method of claim 24, wherein in step (D)(2) said determination of whether said End-Run Oligonucleotide is extended to contain a sequence complementary to a sequence of said Primer Oligonucleotide is conducted by amplifying any End-Run extension product or ligation product using a method comprising the sub-steps of:
   (a) hybridizing said Blocker Oligonucleotide to any of said End-Run extension products present in the incubation to thereby form double-stranded nucleic acid molecules;
   (b) hybridizing a Primer Oligonucleotide to the End-Run extension product of any of said double-stranded nucleic acid molecules such that the 3' terminus of this Primer Oligonucleotide abuts, or can be extended in a polymerase-mediated, template-dependent primer extension reaction to abut, the 5' terminus of the hybridized Blocker Oligonucleotide;
   (c) (1) where said 3' terminus of said hybridized Primer Oligonucleotide of step (b) abuts said 5' terminus of said hybridized Blocker Oligonucleotide, conducting step (d); or
      (2) where said 3' terminus of said hybridized Primer Oligonucleotide of step (b) does not abut said 5' terminus of said hybridized Blocker Oligonucleotide, causing said 3' terminus of said hybridized Primer Oligonucleotide to be extended in a polymerase-mediated, template-dependent primer extension reaction, to thereby form a Primer extension product whose 3' terminus abuts said 5' terminus of said hybridized Blocker Oligonucleotide; then conducting step (d);
   (d) ligating said abutting 3' terminus of any of said hybridized Primer Oligonucleotide of step (c)(1) or said abutting 3' terminus of any of said hybridized Primer extension product of step (c)(2) to said 5' terminus of any of said hybridized Blocker Oligonucleotide to thereby form a ligation product having the sequence of these Primer Oligonucleotide or said Primer extension product, and the sequence of said Blocker Oligonucleotide;
   (e) separating said ligand product from said End-Run extension product;
   (f) hybridizing said End-Run Oligonucleotide to said sequence of said Blocker Oligonucleotide of any of said ligation product; and
   (g) extending the 3' terminus of said hybridized End-Run Oligonucleotide in a polymerase-mediated, template-dependent primer extension reaction to form and amplify said End-Run extension product.

27. The method of claim 26 wherein the sequence of sub-steps (a) through (G) is repeated at least once.

28. The method of claim 24, wherein said predetermined site is a polymorphic locus.

29. The method of claim 24, wherein said 3' terminal nucleotide of said Primer Oligonucleotide in step (B) is capable of hybridizing to said predetermined site only if said site contains a genetic mutation.

30. The method of claim 24, wherein prior to performing step (A), the concentration of said target nucleic acid is amplified according to a method comprising the steps of:
   (A) hybridizing a Blocker Oligonucleotide to said target nucleic acid molecule to thereby form a double-stranded nucleic acid molecule;
   (B) hybridizing a Primer Oligonucleotide to said target nucleic acid molecule of said double-stranded nucleic acid molecule such that the 3' terminus of said Primer Oligonucleotide abuts, or can be extended in a polymerase-mediated, template-dependent primer extension reaction to abut, the 5' terminus of said hybridized Blocker Oligonucleotide;
   (C) (1) where said 3' terminus of said hybridized Primer Oligonucleotide abuts said 5' terminus of said hybridized Blocker Oligonucleotide, conducting step (D); or
      (2) where said 3' terminus of said hybridized Primer Oligonucleotide does not abut said 5' terminus of hybridized Blocker Oligonucleotide, causing said 3' terminus of said hybridized Primer Oligonucleotide to be extended in a polymerase-mediated, template-dependent primer extension reactions to thereby form a Primer extension product whose 3' terminus abuts said 5' terminus of said hybridized Blocker Oligonucleotide; then conducting step (D);

(D) ligating said abutting 3' terminus of said hybridized Primer Oligonucleotide of step (C)(1) or said abutting 3' terminus of said hybridized Primer extension product of step (C)(2) to said 5' terminus of said hybridized Blocker Oligonucleotide to thereby form a ligation product having the sequence of said Primer Oligonucleotide or said Primer extension product, and the sequence of said Blocker Oligonucleotide;

(E) separating said ligation product from said nucleic acid molecule;

(F) hybridizing an End-Run Oligonucleotide to said sequence of said Blocker Oligonucleotide of said ligation product; and (G) extending the 3' terminus of said hybridized End-Run Oligonucleotide in a polymerase-mediated, template-dependent primer extension reaction to thereby for an End-Run extension product whose sequence comprises the target sequence and thereby amplify the concentration of said target molecule; wherein said step (A), said group of steps (B), (C) and (D), and said group of steps (E), (F) and (G), can be conducted in any order with respect to one another.

31. A method of determining whether a selected nucleotide is present at a predetermined site of a target nucleic acid molecule, said method comprising the steps of:

(A) hybridizing a Blocker Oligonucleotide to a nucleic acid sequence complementary to said target nucleic acid molecule to thereby form a double-stranded nucleic acid molecule;

(B) hybridizing a Primer Oligonucleotide to said nucleic acid sequence complementary to said target nucleic acid molecule of said double-stranded nucleic acid molecule such that the 3' terminus of said Primer Oligonucleotide abuts, or can be extended in a polymerase-mediated, template-dependent primer extension reaction to abut, the 5' terminus of said hybridized Blocker Oligonucleotide;

(C) (1) where said 3' terminus of said hybridized Primer Oligonucleotide abuts said 5' terminus of said hybridized Blocker Oligonucleotide, conducting step (D); or (2) where said 3' terminus of said hybridized Primer Oligonucleotide does not abut said 5' terminus of said hybridized Blocker Oligonucleotide, then causing said 3' terminus of said hybridized Primer Oligonucleotide to be extended in a polymerase-mediated, template-dependent primer extension reaction, to thereby form a Primer extension product whose 3' terminus abuts said 5' terminus of said hybridized Blocker Oligonucleotide; then conducting step (D);

(D) ligating said abutting 3' terminus of said hybridized Primer Oligonucleotide of step (C)(1) or said abutting 3' terminus of said hybridized Primer extension product of step (C)(2) to said 5' terminus of said hybridized Blocker Oligonucleotide to thereby form a ligation product having the sequence of said Primer Oligonucleotide or said Primer extension product, and the sequence of said Blocker Oligonucleotide;

(E) separating said ligation product from said nucleic acid sequence;

(F) hybridizing an End-Run Oligonucleotide to said sequence of said Blocker Oligonucleotide of said ligation product, wherein the 3' terminus of said End-Run Oligonucleotide is complementary to said selected nucleotide and said 3' terminal nucleotide of said End-Run Oligonucleotide is capable of opposing said predetermined site of said target molecule;

(G) providing conditions for extending the 3' terminus of said hybridized End-Run Oligonucleotide in a polymerase-mediated, template-dependent primer extension reaction to thereby form an End-Run extension product whose sequence comprises the target sequence;

(H) determining whether said selected nucleotide is present at said predetermined site by detecting whether step (G) results in the formation of said End-Run extension product;

wherein said Blocker Oligonucleotide is present whenever polymerase-mediated, template-dependent extension of said Primer Oligonucleotide can occur.

32. The method of claim 31, wherein in step (H) determining whether step (G) results in the formation of an End-Run extension product containing a sequence complementary to a sequence of said Primer Oligonucleotide is conducted by amplifying any End-Run extension product using a method comprising the sub-steps of:

(a) hybridizing said Blocker Oligonucleotide to any of said End-Run extension products present in the incubation to thereby form double-stranded nucleic acid molecules;

(b) hybridizing a Primer Oligonucleotide to the End-Run extension product of any of said double-stranded nucleic acid molecules such that the 3' terminus of this Primer Oligonucleotide abuts, or can be extended in a polymerase-mediated, template-dependent primer extension reaction to abut, the 5' terminus of the hybridized Blocker Oligonucleotide;

(c) 1. where said 3' terminus of said hybridized Primer Oligonucleotide of step (b) abuts said 5' terminus of said hybridized Blocker Oligonucleotide, conducting step (d); or 2. where said 3' terminus of said hybridized Primer Oligonucleotide of step (b) does not abut said 5' terminus of said hybridized Blocker Oligonucleotide, causing said 3' terminus of said hybridized Primer Oligonucleotide to be extended in a polymerase-mediated, template-dependent primer extension reaction, to thereby form a Primer extension product whose 3' terminus abuts said 5' terminus of said hybridized Blocker Oligonucleotide; then conducting step (d);

(d) ligating said abutting 3' terminus of any of said hybridized Primer Oligonucleotide of step (c)(1) or said abutting 3' terminus of any of said hybridized Primer extension product of step (c)(2) to said 5' terminus of any of said hybridized Blocker Oligonucleotide to thereby form a ligation product having the sequence of these Primer Oligonucleotide or said Primer extension product, and the sequence of said Blocker Oligonucleotide;

(e) separating said ligation product from said End-Run extension product;

(f) hybridizing said End-Run Oligonucleotide to said sequence of said Blocker Oligonucleotide of any of said ligation product; and (g) extending the 3' terminus of said hybridized End-Run Oligonucleotide in a polymerase-mediated, template-dependent primer extension reaction to form and amplify said End-Run extension product.

33. The method of claim 31, wherein prior to performing step (A), the concentration of said target nucleic acid is amplified according to a method comprising the steps of:
- (A) hybridizing a Blocker Oligonucleotide to said target nucleic acid molecule to thereby form a double-stranded nucleic acid molecule;
- (B) hybridizing a Primer Oligonucleotide to said target nucleic acid molecule of said double-stranded nucleic acid molecule such that the 3' terminus of said Primer Oligonucleotide abuts, or can be extended in a polymerase-mediated, template-dependent primer extension reaction to abut the 5' terminus of said hybridized Blocker Oligonucleotide;
- (C) (1) where said 3' terminus of said hybridized Primer Oligonucleotide abuts said 5' terminus of said hybridized Blocker Oligonucleotide, conducting step (D); or
  - (2) where said 3' terminus of said hybridized Primer Oligonucleotide does not abut said 5' terminus of said hybridized Blocker Oligonucleotide, causing said 3' terminus of said hybridized Primer Oligonucleotide to be extended in a polymerase-mediated, template-dependent primer extension reaction, to thereby form a Primer extension product whose 3' terminus abuts said 5' terminus of said hybridized Blocker Oligonucleotide; then conducting step (D);
- (D) ligating said abutting 3' terminus of said hybridized Primer Oligonucleotide of step (C)(1) or said abutting 3' terminus of said hybridized Primer extension product of step (C)(2) to said 5' terminus of said hybridized Blocker Oligonucleotide to thereby form a ligation product having the sequence of said Primer Oligonucleotide or said Primer extension product, and the sequence of said Blocker Oligonucleotide;
- (E) separating said ligation product from said nucleic acid molecule;
- (F) hybridizing an End-Run Oligonucleotide to said sequence of said Blocker Oligonucleotide of said ligation product; and
- (G) extending the 3' terminus of said hybridized End-Run Oligonucleotide in a polymerase-mediated, template-dependent primer extension reaction to thereby form an End-Run extension product whose sequence comprises the target sequence and thereby amplify the concentration of said target molecule; wherein said step (A), said group of steps (B), (C) and (D), and said group of steps (E), (F) and (G), can be conducted in any order with respect to one another.

34. A method of determining whether a selected nucleotide is present at a predetermined site of a target nucleic acid molecule, said method comprising the steps of:
- (A) providing conditions for hybridizing a Blocker Oligonucleotide to said target nucleic acid molecule to thereby form a partially double-stranded nucleic acid molecule;
- (B) providing conditions for hybridizing a Primer Oligonucleotide to said target nucleic acid molecule of said partially double-stranded nucleic acid molecule, wherein the 3' terminus of said Primer Oligonucleotide opposes said predetermined site of said target molecule;
- (C) providing conditions for extending said 3' terminus of said hybridized Primer Oligonucleotide in a polymerase-mediated, template-dependent primer extension reaction, to thereby form a Primer extension product;
- (D) determining whether said selected nucleotide is present at said predetermined site by detecting whether step (C) results in the formation of an End-Run extension product, said detection being accomplished by the sub-steps:
  - (1) incubating said Primer extension product and said 5' terminus of said hybridized Blocker Oligonucleotide in the presence of a ligase, under conditions conducive to nucleic acid ligation;
  - (2) detecting whether step (1) results in the formation of a ligation product having the sequence of said Primer extension product and said Blocker Oligonucleotide, said detection being accomplished by the sub-steps:
    - (a) providing an End-Run Oligonucleotide to said incubation, and maintaining said incubation under conditions sufficient to permit nucleic acid hybridization and polymerase-mediated, template-dependent primer extension to occur; and
    - (b) determining whether said End-Run Oligonucleotide is extended to thereby form an End-Run extension product whose sequence comprises the target sequence and contains a sequence complementary to a sequence of said Primer Oligonucleotide;

wherein said Blocker Oligonucleotide is present whenever polymerase-mediated, template-dependent extension of said Primer Oligonucleotide can occur.

35. The method of claim 34, wherein in step (b) said determination of whether said End-Run Oligonucleotide is extended to contain a sequence complementary to a sequence of said Primer Oligonucleotide is conducted by amplifying any End-Run extension product using a method comprising the sub-steps of:
- (a) hybridizing said Blocker Oligonucleotide to any of said End-Run extension products present in the incubation to thereby form double-stranded nucleic acid molecules;
- (b) hybridizing said Primer Oligonucleotide to the End-Run extension product of any of said double-stranded nucleic acid molecules such that the 3' terminus of said Primer Oligonucleotide abuts, or can be extended in a polymerase-mediated, template-dependent primer extension reaction to abut, the 5' terminus of said hybridized Blocker Oligonucleotide;
- (c) (1) where said 3' terminus of said hybridized Primer Oligonucleotide abuts said 5' terminus of said hybridized Blocker Oligonucleotide, conducting step (d); or
  - (2) where said 3' terminus of said hybridized Primer Oligonucleotide does not abut said 5' terminus of said hybridized Blocker Oligonucleotide, causing said 3' terminus of said hybridized Primer Oligonucleotide to be extended in a polymerase-mediated, template-dependent primer extension reaction, to thereby form a Primer extension product whose 3' terminus abuts said 5' terminus of said hybridized Blocker Oligonucleotide; then conducting step (d);
- (d) ligating said abutting 3' terminus of any of said hybridized Primer Oligonucleotide of step (c)(1) or said abutting 3' terminus of any of said hybridized Primer extension product of step (c)(2) to said 5' terminus of any of said hybridized Blocker Oligonucleotide to thereby form a ligation product having the sequence of said Primer Oligonucleotide or said Primer extension product, and the sequence of said Blocker Oligonucleotide;
- (e) separating said ligation product from said End-Run Extension product;

(f) hybridizing said End-Run Oligonucleotide to said sequence of said Blocker Oligonucleotide of any of said ligation product; and (g) extending the 3' terminus of said hybridized End-Run Oligonucleotide in a polymerase-mediated, template-dependent primer extension reaction to form and amplify said End-Run extension product.

36. The method of claim 35, wherein prior to performing step (A), the concentration of said target nucleic acid is amplified according to a method comprising the steps of:

(A) hybridizing a Blocker Oligonucleotide to said target nucleic acid molecule to thereby form a double-stranded nucleic acid molecule;

(B) hybridizing a Primer Oligonucleotide to said target nucleic acid molecule of said double-stranded nucleic acid molecule such that the 3' terminus of said Primer Oligonucleotide abuts, or can be extended in a polymerase-mediated, template-dependent primer extension reaction to abut, the 5' terminus of said hybridized Blocker Oligonucleotide;

(C) (1) where said 3' terminus of said hybridized Primer Oligonucleotide abuts said 5' terminus of said hybridized Blocker Oligonucleotide, conducting step (D); or (2) where said 3' terminus of said hybridized Primer Oligonucleotide does not abut said 5' terminus of said hybridized Blocker Oligonucleotide, causing said 3' terminus of said hybridized Primer Oligonucleotide to be extended in a polymerase-mediated, template-dependent primer extension reaction, to thereby form a Primer extension product whose 3' terminus abuts said 5' terminus of said hybridized Blocker Oligonucleotide; then conducting step (D);

(D) ligating said abutting 3' terminus of said hybridized Primer Oligonucleotide of step (C)(1) of said abutting 3' terminus of said hybridized Primer extension product of step (C)(2) to said 5' terminus of said hybridized Blocker Oligonucleotide to thereby form a ligation product having the sequence of said Primer Oligonucleotide or said Primer extension product, and the sequence of said Blocker Oligonucleotide;

(E) separating said ligation product from said nucleic acid molecule:

(F) hybridizing an End-Run Oligonucleotide to said sequence of said Blocker Oligonucleotide of said ligation products; and (G) extending the 3' terminus of said hybridized End-Run Oligonucleotide in a polymerase-mediated, template-dependent primer extension reaction to thereby form an End-Run extension product whose sequence comprises the target sequence and thereby amplify the concentration of said target molecule; wherein said step (A), said group of steps (B), (C) and (D), and said group of steps (E), (F) and (G), can be conducted in any order with respect to one another.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 50 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: YES (iv) ANTI-SENSE: NO (xi) SEQUENCE DESCRIPTION: SEQ ID NO:1:

GCCCTTCCCA ACAGTTGCGC AGCCTGAATG GCGAATGGCG CTTTGCCTGG           50

(2) INFORMATION FOR SEQ ID NO:2:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: YES (iv) ANTI-SENSE: NO (xi) SEQUENCE DESCRIPTION: SEQ ID NO:2:

CCATTCAGGC TGCGCAACTG TTG                                        23

(2) INFORMATION FOR SEQ ID NO:3:

(i) SEQUENCE CHARACTERISTICS:
       (A) LENGTH: 10 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: YES (iv) ANTI-SENSE: NO (xi) SEQUENCE DESCRIPTION: SEQ ID NO:3:

GCGCCATTCG                                                       10

(2) INFORMATION FOR SEQ ID NO:4:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: YES (iv) ANTI-SENSE: NO

-continued (xi) SEQUENCE DESCRIPTION: SEQ ID NO:4:

GTTGCGCAGC CTGAATGG                                                          18